US011525766B2

(12) United States Patent
Adams et al.

(10) Patent No.: US 11,525,766 B2
(45) Date of Patent: Dec. 13, 2022

(54) DYNAMIC RANGE EXTENSION SYSTEMS AND METHODS FOR PARTICLE ANALYSIS IN BLOOD SAMPLES

(71) Applicant: Iris International, Inc., Chatsworth, CA (US)

(72) Inventors: Thomas H. Adams, Leucadia, CA (US); Bart J. Wanders, Trabuco Canyon, CA (US); John Roche, Scarborough, ME (US); Harvey L. Kasdan, Jerusalem (IL)

(73) Assignee: Iris International, Inc., Chatsworth, CA (US)

( * ) Notice: Subject to any disclaimer, the term of this patent is extended or adjusted under 35 U.S.C. 154(b) by 432 days.

(21) Appl. No.: 16/533,006

(22) Filed: Aug. 6, 2019

(65) Prior Publication Data
US 2020/0033249 A1    Jan. 30, 2020

Related U.S. Application Data

(62) Division of application No. 14/217,034, filed on Mar. 17, 2014, now Pat. No. 10,429,292.
(Continued)

(51) Int. Cl.
*G01N 15/14* (2006.01)
*G01N 33/50* (2006.01)
(Continued)

(52) U.S. Cl.
CPC ........... *G01N 15/1404* (2013.01); *G01N 1/30* (2013.01); *G01N 15/06* (2013.01); *G01N 15/147* (2013.01);
(Continued)

(58) Field of Classification Search
CPC .. G01N 15/06; G01N 15/1463; G01N 15/147; G01N 1/30; G01N 2015/1452;
(Continued)

(56) References Cited

U.S. PATENT DOCUMENTS 3,819,270 A    6/1974   Hirschfeld
3,822,095 A    7/1974   Hirschfeld
(Continued)

FOREIGN PATENT DOCUMENTS

BR    112015020098 A2    7/2017
BR    112015021593       12/2020
(Continued)

OTHER PUBLICATIONS

"U.S. Appl. No. 14/217,034, Advisory Action dated Mar. 10, 2016", 3 pgs.
(Continued)

*Primary Examiner* — Dean Kwak
(74) *Attorney, Agent, or Firm* — Schwegman Lundberg & Woessner, P.A.

(57) ABSTRACT

For analyzing a sample containing particles of at least two categories, such as a sample containing blood cells, a particle counter subject to a detection limit is coupled with an analyzer capable of discerning particle number ratios, such as a visual analyzer, and a processor. A first category of particles can be present beyond detection range limits while a second category of particles is present within respective detection range limits. The concentration of the second category of particles is determined by the particle counter. A ratio of counts of the first category to the second category is determined on the analyzer. The concentration of particles in the first category is calculated on the processor based on the ratio and the count or concentration of particles in the second category.

15 Claims, 19 Drawing Sheets

Related U.S. Application Data

(60) Provisional application No. 61/799,152, filed on Mar. 15, 2013.

(51) Int. Cl.

| | | |
|---|---|---|
| *G01N 15/06* | (2006.01) | |
| *G01N 21/53* | (2006.01) | |
| *G02B 7/36* | (2021.01) | |
| *G01N 33/80* | (2006.01) | |
| *G01N 33/49* | (2006.01) | |
| *G01N 15/00* | (2006.01) | |
| *G01N 15/10* | (2006.01) | |
| *G01N 21/05* | (2006.01) | |
| *G02B 21/24* | (2006.01) | |
| *G06T 7/00* | (2017.01) | |
| *G02B 7/28* | (2021.01) | |
| *G01N 1/30* | (2006.01) | |

(52) U.S. Cl.
CPC ..... *G01N 15/1429* (2013.01); *G01N 15/1434* (2013.01); *G01N 15/1436* (2013.01); *G01N 15/1459* (2013.01); *G01N 15/1463* (2013.01); *G01N 15/1468* (2013.01); *G01N 15/1475* (2013.01); *G01N 21/53* (2013.01); *G01N 33/49* (2013.01); *G01N 33/4915* (2013.01); *G01N 33/5091* (2013.01); *G01N 33/5094* (2013.01); *G01N 33/80* (2013.01); *G02B 7/36* (2013.01); *G01N 2015/0065* (2013.01); *G01N 2015/1037* (2013.01); *G01N 2015/144* (2013.01); *G01N 2015/1411* (2013.01); *G01N 2015/1413* (2013.01); *G01N 2015/1452* (2013.01); *G01N 2015/1481* (2013.01); *G01N 2015/1486* (2013.01); *G01N 2021/058* (2013.01); *G02B 7/28* (2013.01); *G02B 21/244* (2013.01); *G06T 7/0012* (2013.01); *G06T 2207/10148* (2013.01)

(58) Field of Classification Search
CPC .......... G01N 33/5091; G01N 15/1468; G01N 15/1475; G01N 33/5094; G01N 15/1404; G01N 15/1434; G01N 2015/0065; G01N 2015/1037; G01N 2015/1411; G01N 2015/1413; G01N 2015/1486; G01N 2021/058; G01N 21/53; G01N 33/49; G01N 33/4915; G01N 33/80; G01N 15/1459; G01N 15/1429; G01N 2015/1481; G02B 21/244; G06T 2207/10148; G06T 7/0012; G06K 9/00127
USPC .............. 702/21, 23, 26, 46; 422/73; 436/10
See application file for complete search history.

(56) References Cited

U.S. PATENT DOCUMENTS

| | | | |
|---|---|---|---|
| 3,888,782 A | 6/1975 | Boghosian et al. | |
| 4,338,024 A | 7/1982 | Bolz et al. | |
| 4,393,466 A | 7/1983 | Deindoerfer et al. | |
| 4,421,559 A | 12/1983 | Owatari | |
| 4,428,669 A | 1/1984 | Bessis | |
| 4,606,631 A | 8/1986 | Anno et al. | |
| 4,647,531 A | 3/1987 | Kamentsky | |
| 4,732,479 A | 3/1988 | Tanaka et al. | |
| 5,007,732 A | 4/1991 | Ohki et al. | |
| 5,023,257 A | 6/1991 | Pollinger et al. | |
| 5,083,014 A | 1/1992 | Kosaka | |
| 5,159,403 A | 10/1992 | Kosaka | |
| 5,308,526 A | 5/1994 | Dias et al. | |
| 5,412,466 A | 5/1995 | Ogino | |
| 5,436,978 A * | 7/1995 | Kasdan | G01N 15/1468 356/39 |
| 5,457,526 A | 10/1995 | Kosaka | |
| 5,585,246 A | 12/1996 | Dubrow et al. | |
| 5,619,032 A | 4/1997 | Kasdan | |
| 5,633,503 A | 5/1997 | Kosaka | |
| 5,690,895 A | 11/1997 | Matsumoto et al. | |
| 5,808,737 A | 9/1998 | Edens et al. | |
| 5,812,419 A * | 9/1998 | Chupp | G01N 35/1004 702/20 |
| 5,822,447 A | 10/1998 | Kasdan | |
| 5,872,627 A | 2/1999 | Miers | |
| 5,880,835 A * | 3/1999 | Yamazaki | G01N 15/147 356/336 |
| 5,889,881 A | 3/1999 | Macaulay et al. | |
| 6,130,745 A | 10/2000 | Manian et al. | |
| 6,184,976 B1 | 2/2001 | Park et al. | |
| 6,184,978 B1 | 2/2001 | Kasdan et al. | |
| 6,365,106 B1 | 4/2002 | Nagai | |
| 6,424,415 B1 | 7/2002 | Kasdan et al. | |
| 6,441,894 B1 | 8/2002 | Manian et al. | |
| 6,590,646 B2 | 7/2003 | Kasdan et al. | |
| 6,632,676 B1 | 10/2003 | Crews et al. | |
| 6,825,926 B2 | 11/2004 | Turner et al. | |
| 6,947,586 B2 | 9/2005 | Kasdan et al. | |
| 7,041,952 B2 | 5/2006 | Iffland et al. | |
| 7,071,451 B2 | 7/2006 | Ishikawa et al. | |
| 7,236,623 B2 | 6/2007 | Chapoulaud et al. | |
| 7,319,907 B2 | 1/2008 | Kasdan et al. | |
| 7,324,694 B2 | 1/2008 | Chapoulaud et al. | |
| 7,351,221 B2 | 4/2008 | Trombley, III et al. | |
| 7,362,409 B2 | 4/2008 | Tamatani et al. | |
| 7,439,269 B2 | 10/2008 | Clarot et al. | |
| 7,486,329 B2 | 2/2009 | Endo | |
| 7,799,575 B2 | 9/2010 | Jiang | |
| 7,822,276 B2 | 10/2010 | Turner et al. | |
| 7,824,916 B2 | 11/2010 | Fujimoto | |
| 7,825,360 B2 | 11/2010 | Karasawa et al. | |
| 7,855,831 B2 | 12/2010 | Wolleschensky et al. | |
| 8,174,686 B2 | 5/2012 | Namba et al. | |
| 8,343,978 B2 | 1/2013 | Dong | |
| 8,362,409 B2 | 1/2013 | Cooper et al. | |
| 8,445,284 B2 | 5/2013 | Lapen et al. | |
| 8,564,776 B2 | 10/2013 | Graves et al. | |
| 9,276,349 B2 | 3/2016 | Yoshida et al. | |
| 9,279,750 B2 | 3/2016 | Cremins et al. | |
| 9,316,635 B2 | 4/2016 | Farrell et al. | |
| 9,316,653 B2 | 4/2016 | Donovan et al. | |
| 9,322,752 B2 | 4/2016 | Wanders et al. | |
| 9,470,618 B2 | 10/2016 | Farrell et al. | |
| 9,702,806 B2 | 7/2017 | Wanders et al. | |
| 9,857,361 B2 | 1/2018 | Wanders et al. | |
| 9,909,973 B2 | 3/2018 | Wanders et al. | |
| 10,060,846 B2 | 8/2018 | Wanders et al. | |
| 10,345,217 B2 | 7/2019 | Wanders et al. | |
| 10,429,292 B2 | 10/2019 | Adams et al. | |
| 10,451,612 B2 | 10/2019 | Farrell et al. | |
| 10,705,008 B2 | 7/2020 | Wanders et al. | |
| 2002/0002847 A1 | 1/2002 | Son et al. | |
| 2002/0028471 A1 | 3/2002 | Oberhardt | |
| 2003/0113925 A1 | 6/2003 | Gordon et al. | |
| 2004/0070757 A1 | 4/2004 | Moore et al. | |
| 2004/0169867 A1 | 9/2004 | Sharpe | |
| 2004/0180444 A1 | 9/2004 | Rannikko et al. | |
| 2004/0241677 A1 | 12/2004 | Lin et al. | |
| 2005/0106739 A1 | 5/2005 | Cabuz et al. | |
| 2005/0127271 A1 | 6/2005 | Ortyn et al. | |
| 2005/0180885 A1 | 8/2005 | Tateishi et al. | |
| 2006/0050946 A1 | 3/2006 | Mitchison et al. | |
| 2006/0148028 A1 | 7/2006 | Noda et al. | |
| 2007/0020721 A1 | 1/2007 | Yoshida et al. | |
| 2007/0111276 A1 | 5/2007 | Lefevre et al. | |
| 2007/0209938 A1 | 9/2007 | Zhang et al. | |
| 2008/0019584 A1 | 1/2008 | Lindberg et al. | |
| 2008/0038738 A1 | 2/2008 | Weigum et al. | |
| 2008/0138852 A1 | 6/2008 | Winkelman et al. | |
| 2008/0283722 A1 | 11/2008 | Uchiyama et al. | |
| 2009/0011430 A1 | 1/2009 | Ateya et al. | |
| 2009/0158823 A1 | 6/2009 | Kaduchak et al. | |

(56) References Cited

U.S. PATENT DOCUMENTS

| | | |
|---|---|---|
| 2009/0178716 A1 | 7/2009 | Kaduchak et al. |
| 2009/0269799 A1 | 10/2009 | Winkelman et al. |
| 2009/0325217 A1 | 12/2009 | Luscher |
| 2010/0000325 A1 | 1/2010 | Kaduchak et al. |
| 2010/0054575 A1 | 3/2010 | Zhou et al. |
| 2010/0111768 A1 | 5/2010 | Banerjee et al. |
| 2010/0178666 A1 | 7/2010 | Natanel et al. |
| 2010/0284602 A1 | 11/2010 | Winkelman et al. |
| 2011/0014645 A1 | 1/2011 | Winkelman et al. |
| 2011/0022205 A1 | 1/2011 | Nakayama |
| 2011/0070606 A1 | 3/2011 | Winkelman et al. |
| 2011/0076712 A1 | 3/2011 | Gilligan et al. |
| 2011/0128545 A1 | 6/2011 | Cox et al. |
| 2011/0222051 A1 | 9/2011 | Heng |
| 2012/0035061 A1 | 2/2012 | Bransky et al. |
| 2012/0092667 A1 | 4/2012 | Tsukii et al. |
| 2012/0103112 A1 | 5/2012 | Vrane et al. |
| 2012/0134559 A1 | 5/2012 | Suzuki et al. |
| 2012/0196314 A1 | 8/2012 | Nawaz et al. |
| 2012/0301883 A1 | 11/2012 | Pagano et al. |
| 2012/0315690 A1 | 12/2012 | Di Carlo et al. |
| 2012/0322099 A1 | 12/2012 | Lapen et al. |
| 2013/0070249 A1 | 3/2013 | Choi et al. |
| 2014/0113324 A1 | 4/2014 | Di Carlo et al. |
| 2014/0193892 A1 | 7/2014 | Mohan et al. |
| 2014/0273067 A1 | 9/2014 | Wanders et al. |
| 2014/0273068 A1 | 9/2014 | Wanders et al. |
| 2014/0273076 A1 | 9/2014 | Adams et al. |
| 2014/0273081 A1 | 9/2014 | Cremins et al. |
| 2014/0273082 A1 | 9/2014 | Cremins |
| 2014/0296089 A1 | 10/2014 | Holmes et al. |
| 2014/0315238 A1 | 10/2014 | Farrell et al. |
| 2014/0329265 A1 | 11/2014 | Wanders et al. |
| 2016/0041083 A1 | 2/2016 | Wanders et al. |
| 2016/0169785 A1 | 6/2016 | Wanders et al. |
| 2016/0187246 A1 | 6/2016 | Farrell et al. |
| 2017/0003273 A1 | 1/2017 | Farrell et al. |
| 2017/0370820 A1 | 12/2017 | Wanders et al. |
| 2018/0149576 A1 | 5/2018 | Wanders et al. |
| 2020/0080926 A1 | 3/2020 | Wanders et al. |

FOREIGN PATENT DOCUMENTS

| | | |
|---|---|---|
| CA | 2349995 A1 | 12/2001 |
| CN | 1265195 A | 8/2000 |
| CN | 1265196 A | 8/2000 |
| CN | 1521497 A | 8/2004 |
| CN | 1739018 A | 2/2006 |
| CN | 1834612 | 9/2006 |
| CN | 101013080 A | 8/2007 |
| CN | 101065656 A | 10/2007 |
| CN | 101252994 A | 8/2008 |
| CN | 101536016 A | 9/2009 |
| CN | 102998437 A | 3/2013 |
| CN | 105164510 A | 12/2015 |
| CN | 109142195 A | 1/2019 |
| CN | 105074422 B | 7/2019 |
| CN | 105074420 | 7/2021 |
| CN | 113484200 | 10/2021 |
| EP | 0286088 A2 | 10/1988 |
| EP | 0468100 A1 | 1/1992 |
| EP | 0486747 A2 | 5/1992 |
| EP | 0556971 A2 | 8/1993 |
| EP | 0656540 A2 | 6/1995 |
| EP | 0708334 A2 | 4/1996 |
| EP | 0949498 A2 | 10/1999 |
| EP | 1264205 A2 | 12/2002 |
| EP | 1761817 A1 | 3/2007 |
| EP | 1942333 | 7/2008 |
| EP | 2028264 A1 | 2/2009 |
| EP | 2030062 A1 | 3/2009 |
| EP | 2083268 A1 | 7/2009 |
| EP | 2568288 | 3/2013 |
| EP | 2972200 A2 | 1/2016 |
| EP | 2972204 A1 | 1/2016 |
| EP | 2972208 A1 | 1/2016 |
| EP | 2972210 A1 | 1/2016 |
| EP | 2972211 A1 | 1/2016 |
| EP | 2972214 A1 | 1/2016 |
| EP | 2972208 B1 | 6/2018 |
| EP | 2972214 B1 | 10/2018 |
| EP | 2972211 B1 | 12/2018 |
| EP | 3467472 A1 | 4/2019 |
| EP | 3489656 A1 | 5/2019 |
| EP | 3467472 | 4/2021 |
| EP | 3489656 B1 | 11/2021 |
| GB | 1471976 A | 4/1977 |
| GB | 1557691 A | 12/1979 |
| GB | 2121976 A | 1/1984 |
| GB | 2167880 A | 6/1986 |
| IN | 7649DELNP2015 A | 1/2016 |
| IN | 8082DELNP2015 A | 7/2016 |
| JP | 4952489 A | 5/1974 |
| JP | H04188042 A | 7/1992 |
| JP | H05296915 A | 11/1993 |
| JP | H06281557 A | 10/1994 |
| JP | H0989753 A | 4/1997 |
| JP | 2874746 B2 | 3/1999 |
| JP | 2001048455 A | 2/2001 |
| JP | 2003005086 A | 1/2003 |
| JP | 2003005088 A | 1/2003 |
| JP | 2004188042 A | 7/2004 |
| JP | 2009089752 A | 4/2009 |
| JP | 2010506175 A | 2/2010 |
| JP | 2016519758 A | 7/2016 |
| JP | 2016520805 A | 7/2016 |
| JP | 2016520806 A | 7/2016 |
| JP | 6523245 B2 | 5/2019 |
| KR | 102044593 B1 | 11/2019 |
| KR | 102053487 B1 | 12/2019 |
| KR | 102055474 B1 | 12/2019 |
| KR | 102067317 | 1/2020 |
| KR | 102095617 | 3/2020 |
| WO | WO-9743620 A1 | 11/1997 |
| WO | WO-9905504 A2 | 2/1999 |
| WO | WO-0011449 A1 | 3/2000 |
| WO | WO-0148455 A2 | 7/2001 |
| WO | WO-2004022774 A1 | 3/2004 |
| WO | WO-2004045488 A2 | 6/2004 |
| WO | WO-2014145983 A1 | 9/2014 |
| WO | WO-2014145984 A1 | 9/2014 |
| WO | WO-2014145989 A1 | 9/2014 |
| WO | WO-2014146030 A1 | 9/2014 |
| WO | WO-2014146051 A1 | 9/2014 |
| WO | WO-2014146061 A1 | 9/2014 |
| WO | WO-2014146062 A2 | 9/2014 |
| WO | WO-2014146063 A2 | 9/2014 |
| WO | WO-2014146063 A9 | 11/2014 |
| WO | WO-2014146063 A3 | 1/2015 |

OTHER PUBLICATIONS

"U.S. Appl. No. 14/217,034, Advisory Action dated Sep. 21, 2017", 4 pgs.

"U.S. Appl. No. 14/217,034, Advisory Action dated Nov. 13, 2018", 5 pgs.

"U.S. Appl. No. 14/217,034, Advisory Action dated Dec. 1, 2016", 3 pgs.

"U.S. Appl. No. 14/217,034, Examiner Interview Summary dated May 11, 2017", 3 pgs.

"U.S. Appl. No. 14/217,034, Examiner Interview Summary dated Jun. 8, 2018", 3 pgs.

"U.S. Appl. No. 14/217,034, Examiner Interview Summary dated Sep. 2, 2016", 3 pgs.

"U.S. Appl. No. 14/217,034, Examiner Interview Summary dated Sep. 19, 2017", 3 pgs.

"U.S. Appl. No. 14/217,034, Examiner Interview Summary dated Oct. 9, 2018", 3 pgs.

"U.S. Appl. No. 14/217,034, Final Office Action dated Jan. 22, 2016", 10 pgs.

"U.S. Appl. No. 14/217,034, Final Office Action dated Jul. 10, 2017", 13 pgs.

(56) References Cited

OTHER PUBLICATIONS

"U.S. Appl. No. 14/217,034, Final Office Action dated Sep. 7, 2018", 17 pgs.
"U.S. Appl. No. 14/217,034, Final Office Action dated Sep. 22, 2016", 11 pgs.
"U.S. Appl. No. 14/217,034, Non Final Office Action dated Mar. 3, 2017", 15 pgs.
"U.S. Appl. No. 14/217,034, Non Final Office Action dated Mar. 30, 2018", 18 pgs.
"U.S. Appl. No. 14/217,034, Non Final Office Action dated Jun. 23, 2016", 10 pgs.
"U.S. Appl. No. 14/217,034, Non Final Office Action dated Aug. 13, 2015", 7 pgs.
"U.S. Appl. No. 14/217,034, Notice of Allowance dated May 8, 2019", 17 pgs.
"U.S. Appl. No. 14/217,034, Preliminary Amendment filed Apr. 18, 2014", 9 pgs.
"U.S. Appl. No. 14/217,034, Response filed Jan. 31, 2017 to Restriction Requirement dated Jan. 26, 2017", 9 pgs.
"U.S. Appl. No. 14/217,034, Response filed Mar. 3, 2016 to Final Office Action dated Jan. 22, 2016", 10 pgs.
"U.S. Appl. No. 14/217,034, Response filed Jun. 5, 2017 to Non Final Office Action dated Mar. 3, 2017", 17 pgs.
"U.S. Appl. No. 14/217,034, Response filed Jun. 25, 2018 to Non Final Office Action dated Mar. 30, 2018", 16 pgs.
"U.S. Appl. No. 14/217,034, Response filed Jul. 20, 2015 to Restriction Requirement dated Apr. 20, 2015", 9 pgs.
"U.S. Appl. No. 14/217,034, Response filed Sep. 1, 2016 to Non Final Office Action dated Jun. 23, 2016", 15 pgs.
"U.S. Appl. No. 14/217,034, Response filed Sep. 11, 2017 to Final Office Action dated Jul. 10, 2017", 12 pgs.
"U.S. Appl. No. 14/217,034, Response filed Oct. 2, 2015 to Non Final Office Action dated Aug. 13, 2015", 9 pgs.
"U.S. Appl. No. 14/217,034, Response filed Oct. 6, 2017 to Advisory Action dated Sep. 21, 2017", 14 pgs.
"U.S. Appl. No. 14/217,034, Response filed Nov. 1, 2018 to Final Office Action dated Sep. 7, 2018", 18 pgs.
"U.S. Appl. No. 14/217,034, Response filed Nov. 16, 2016 to Final Office Action dated Sep. 22, 2016", 10 pgs.
"U.S. Appl. No. 14/217,034, Response filed Nov. 17, 2015 to Restriction Requirement dated Oct. 28, 2015", 9 pgs.
"U.S. Appl. No. 14/217,034, Response filed Dec. 7, 2018 to Advisory Action dated Nov. 13, 2018", 18 pgs.
"U.S. Appl. No. 14/217,034, Restriction Requirement dated Jan. 26, 2017", 6 pgs.
"U.S. Appl. No. 14/217,034, Restriction Requirement dated Apr. 20, 2015", 6 pgs.
"U.S. Appl. No. 14/217,034, Restriction Requirement dated Oct. 28, 2015", 5 pgs.
"Chinese Application Serial No. 201480015280.1, Notice of Decision to Grant dated Oct. 15, 2018", 4 pgs.
"Coulter VCS Reticulocyte Method", Coulter International Corp., [Online] Retrieved from the Internet: <URL: http://www.cyto.purdue.edu-cdroms-cyto2-6-coulter-ss000126.html>, (Oct. 25, 1996), 2 pgs.
"International Application Serial No. PCT/US2014/030939, International Search Report dated Jul. 7, 2014", 5 pgs.
"International Application Serial No. PCT/US2014/030939, Written Opinion dated Jul. 7, 2014", 9 pgs.
"International Application Serial No. PCT/US2014/030942, International Search Report dated Oct. 14, 2014", 8 pgs.
"International Application Serial No. PCT/US2014/030942, Written Opinion dated Oct. 14, 2014", 21 pgs.
"Korean Application Serial No. 10-2015-7024439, Notice of Preliminary Rejection dated Jul. 16, 2019", w/ English Translation, 4 pgs.
"Korean Application Serial No. 10-2015-7024466, Notice of Preliminary Rejection dated Jul. 17, 2019", w/ English Translation, 13 pgs.
Cubaud, T, et al., "High-Viscosity Fluid Threads in Weakly Diffusive Microfluidic Systems", New Journal of Physics, vol. 11, No. 7, (2009), 14 pgs.
Kachel, V, et al., "Uniform Lateral Orientation, Caused by Flow Forces, of Flat Particles in Flow-Through System", Journal of Histochemistry and Cytochemistry, 25(7), (1977), 774-780.
Wietzorrek, Joachim, et al., "A New Multiparameter Flow Cytometer: Optical and Electrical Cell Analysis in Combination With Video Microscopy in Flow", Cytometry, 35(4), (Apr. 1, 1999), 291-301.
Wu, Zhigang, et al., "Rapid Mixing Using Two-Phase Hydraulic Focusing in Microchannels", Biomedical Microdevices, vol. 7, No. 1, (Mar. 1, 2005), 13-20.
"U.S. Appl. No. 14/216,811, Preliminary Amendment filed Apr. 24, 2014", 10 pgs.
"U.S. Appl. No. 14/215,834, Final Office Action dated Nov. 17, 2015", 8 pgs.
"U.S. Appl. No. 14/215,834, Non Final Office Action dated Aug. 20, 2015", 6 pgs.
"U.S. Appl. No. 14/215,834, Notice of Allowance dated Dec. 18, 2015", 8 pgs.
"U.S. Appl. No. 14/215,834, Preliminary Amendment filed Apr. 2, 2014", 10 pgs.
"U.S. Appl. No. 14/215,834, Response filed Jul. 20, 2015 to Restriction Requirement dated Apr. 20, 2015", 8 pgs.
"U.S. Appl. No. 14/215,834, Response filed Oct. 13, 2015 to Non Final Office Action dated Aug. 20, 2015", 9 pgs.
"U.S. Appl. No. 14/215,834, Response filed Dec. 8, 2015 to Final Office Action dated Nov. 17, 2015", 11 pgs.
"U.S. Appl. No. 14/215,834, Restriction Requirement dated Apr. 20, 2015", 7 pgs.
"U.S. Appl. No. 14/216,339, 312 Amendment filed Nov. 9, 2015", 8 pgs.
"U.S. Appl. No. 14/216,339, Non Final Office Action dated Jun. 29, 2015", 6 pgs.
"U.S. Appl. No. 14/216,339, Notice of Allowance dated Nov. 2, 2015", 9 pgs.
"U.S. Appl. No. 14/216,339, PTO Response to Rule 312 Communication dated Jan. 20, 2016", 2 pgs.
"U.S. Appl. No. 14/216,339, Response filed Jun. 9, 2015 to Restriction Requirement dated Apr. 21, 2015", 5 pgs.
"U.S. Appl. No. 14/216,339, Response filed Sep. 29, 2015 to Non Final Office Action dated Jun. 29, 2015", 12 pgs.
"U.S. Appl. No. 14/216,339, Restriction Requirement dated Apr. 21, 2015", 5 pgs.
"U.S. Appl. No. 14/216,533, 312 Amendment filed Mar. 9, 2016", 7 pgs.
"U.S. Appl. No. 14/216,533, Non Final Office Action dated Aug. 21, 2015", 10 pgs.
"U.S. Appl. No. 14/216,533, Notice of Allowance dated Jan. 4, 2016", 15 pgs.
"U.S. Appl. No. 14/216,533, Preliminary Amendment filed May 1, 2014", 12 pgs.
"U.S. Appl. No. 14/216,533, Preliminary Amendment filed Nov. 24, 2014", 7 pgs.
"U.S. Appl. No. 14/216,533, PTO Response to Rule 312 Communication dated Mar. 21, 2016", 2 pgs.
"U.S. Appl. No. 14/216,533, Response filed Jul. 21, 2015 to Restriction Requirement dated Apr. 21, 2015", 9 pgs.
"U.S. Appl. No. 14/216,533, Response filed Nov. 9, 2015 to Non Final Office Action dated Aug. 21, 2015", 10 pgs.
"U.S. Appl. No. 14/216,533, Restriction Requirement dated Apr. 21, 2015", 5 pgs.
"U.S. Appl. No. 14/216,533, Supplemental Amendment filed Nov. 11, 2015", 8 pgs.
"U.S. Appl. No. 14/216,811, Advisory Action dated Jan. 14, 2019", 5 pgs.
"U.S. Appl. No. 14/216,811, Advisory Action dated Mar. 17, 2016", 3 pgs.
"U.S. Appl. No. 14/216,811, Advisory Action dated Nov. 23, 2016", 5 pgs.
"U.S. Appl. No. 14/216,811, Advisory Action dated Nov. 24, 2017", 3 pgs.

(56) References Cited

OTHER PUBLICATIONS

"U.S. Appl. No. 14/216,811, Advisory Action dated Dec. 7, 2017", 4 pgs.
"U.S. Appl. No. 14/216,811, Corrected Notice of Allowability dated Nov. 6, 2019", 3 pgs.
"U.S. Appl. No. 14/216,811, Examiner Interview Summary dated Sep. 9, 2016", 3 pgs.
"U.S. Appl. No. 14/216,811, Examiner Interview Summary dated Sep. 16, 2016", 3 pgs.
"U.S. Appl. No. 14/216,811, Examiner Interview Summary dated Sep. 27, 2018", 3 pgs.
"U.S. Appl. No. 14/216,811, Final Office Action dated Jan. 8, 2016", 9 pgs.
"U.S. Appl. No. 14/216,811, Final Office Action dated Sep. 18, 2017", 16 pgs.
"U.S. Appl. No. 14/216,811, Final Office Action dated Oct. 12, 2016", 10 pgs.
"U.S. Appl. No. 14/216,811, Final Office Action dated Nov. 2, 2018", 21 pgs.
"U.S. Appl. No. 14/216,811, Non Final Office Action dated Feb. 24, 2017", 12 pgs.
"U.S. Appl. No. 14/216,811, Non Final Office Action dated Jun. 18, 2018", 17 pgs.
"U.S. Appl. No. 14/216,811, Non Final Office Action dated Jul. 21, 2016", 11 pgs.
"U.S. Appl. No. 14/216,811, Non Final Office Action dated Aug. 13, 2015", 10 pgs.
"U.S. Appl. No. 14/216,811, Notice of Allowance dated Mar. 3, 2020", 14 pgs.
"U.S. Appl. No. 14/216,811, Notice of Allowance dated Jun. 19, 2019", 16 pgs.
"U.S. Appl. No. 14/216,811, Response filed Feb. 4, 2019 to Advisory Action dated Jan. 14, 2019", 9 pgs.
"U.S. Appl. No. 14/216,811, Response filed Mar. 7, 2016 to Final Office Action dated Jan. 8, 2016", 33 pgs.
"U.S. Appl. No. 14/216,811, Response filed Jul. 21, 2015 to Restriction Requirement dated Apr. 21, 2015", 8 pgs.
"U.S. Appl. No. 14/216,811, Response filed Sep. 17, 2018 to Non Final Office Action dated Jun. 18, 2018", 13 pgs.
"U.S. Appl. No. 14/216,811, Response filed Nov. 9, 2015 to Non Final Office Action dated Aug. 13, 2015", 12 pgs.
"U.S. Appl. No. 14/216,811, Response filed Dec. 4, 2017 to Advisory Action dated Nov. 24, 2017", 10 pgs.
"U.S. Appl. No. 14/216,811, Response filed Dec. 27, 2018 to Final Office Action dated Nov. 2, 2018", 10 pgs.
"U.S. Appl. No. 14/216,811, Restriction Requirement dated Apr. 21, 2015", 6 pgs.
"U.S. Appl. No. 14/216,811, Restriction Requirement dated Jun. 8, 2017", 6 pgs.
"U.S. Appl. No. 14/216,811, Supplemental Amendment filed Sep. 24, 2018", 8 pgs.
"U.S. Appl. No. 14/775,448, 312 Amendment filed Apr. 24, 2017", 8 pgs.
"U.S. Appl. No. 14/775,448, Non Final Office Action dated Jan. 12, 2017", 15 pgs.
"U.S. Appl. No. 14/775,448, Notice of Allowance dated Mar. 8, 2017", 8 pgs.
"U.S. Appl. No. 14/775,448, Preliminary Amendment filed Sep. 11, 2015", 8 pgs.
"U.S. Appl. No. 14/775,448, PTO Response to Rule 312 Communication dated May 8, 2017", 2 pgs.
"U.S. Appl. No. 14/775,448, Response filed Feb. 8, 2017 to Non Final Office Action dated Jan. 12, 2017", 13 pgs.
"U.S. Appl. No. 15/047,971, Examiner Interview Summary dated Mar. 21, 2017", 3 pgs.
"U.S. Appl. No. 15/047,971, Non Final Office Action dated Jan. 30, 2017", 12 pgs.
"U.S. Appl. No. 15/047,971, Notice of Allowance dated Oct. 23, 2017", 15 pgs.
"U.S. Appl. No. 15/047,971, Response filed Jan. 9, 2017 to Restriction Requirement dated Nov. 7, 2016", 7 pgs.
"U.S. Appl. No. 15/047,971, Response filed Jun. 30, 2017 to Non Final Office Action dated Jan. 30, 2017", 14 pgs.
"U.S. Appl. No. 15/047,971, Restriction Requirement dated Jul. 19, 2017", 6 pgs.
"U.S. Appl. No. 15/047,971, Restriction Requirement dated Nov. 7, 2016", 6 pgs.
"U.S. Appl. No. 15/064,129, 312 Amendment filed Sep. 1, 2016", 6 pgs.
"U.S. Appl. No. 15/064,129, Notice of Allowance dated Aug. 29, 2016", 15 pgs.
"U.S. Appl. No. 15/064,129, PTO Response to Rule 312 Communication dated Sep. 12, 2016", 2 pgs.
"U.S. Appl. No. 15/263,001, Advisory Action dated Sep. 13, 2018", 3 pgs.
"U.S. Appl. No. 15/263,001, Corrected Notice of Allowability dated Aug. 29, 2019", 3 pgs.
"U.S. Appl. No. 15/263,001, Examiner Interview Summary dated Mar. 25, 2019", 3 pgs.
"U.S. Appl. No. 15/263,001, Examiner Interview Summary dated Oct. 11, 2018", 3 pgs.
"U.S. Appl. No. 15/263,001, Final Office Action dated Jul. 6, 2018", 8 pgs.
"U.S. Appl. No. 15/263,001, Non Final Office Action dated Jan. 7, 2019", 9 pgs.
"U.S. Appl. No. 15/263,001, Non Final Office Action dated Feb. 14, 2018", 7 pgs.
"U.S. Appl. No. 15/263,001, Notice of Allowance dated Jun. 5, 2019", 8 pgs.
"U.S. Appl. No. 15/263,001, Response filed Jan. 18, 2018 to Restriction Requirement dated Nov. 27, 2017", 6 pgs.
"U.S. Appl. No. 15/263,001, Response filed Mar. 29, 2019 to Non Final Office Action dated Jan. 7, 2019", 9 pgs.
"U.S. Appl. No. 15/263,001, Response filed May 9, 2018 to Non Final Office Action dated Feb. 14, 2018", 8 pgs.
"U.S. Appl. No. 15/263,001, Response filed Sep. 5, 2018 to Final Office Action dated Jul. 6, 2018", 7 pgs.
"U.S. Appl. No. 15/263,001, Response filed Oct. 3, 2018 to Advisory Action dated Sep. 13, 2018", 8 pgs.
"U.S. Appl. No. 15/263,001, Restriction Requirement dated Nov. 27, 2017", 5 pgs.
"U.S. Appl. No. 15/645,710, 312 Amendment filed Jul. 5, 2018", 4 pgs.
"U.S. Appl. No. 15/645,710, Notice of Allowance dated Apr. 12, 2018", 10 pgs.
"U.S. Appl. No. 15/645,710, Preliminary Amendment filed Sep. 18, 2017", 6 pgs.
"U.S. Appl. No. 15/645,710, PTO Response to Rule 312 Communication dated Jul. 18, 2018", 2 pgs.
"U.S. Appl. No. 15/880,328, Notice of Allowance dated Feb. 20, 2019", 12 pgs.
"U.S. Appl. No. 15/880,328, Response filed Dec. 11, 2018 to Restriction Requirement dated Nov. 5, 2018", 7 pgs.
"U.S. Appl. No. 15/880,328, Restriction Requirement dated Nov. 5, 2018", 6 pgs.
"U.S. Appl. No. 16/574,693, Preliminary Amendment filed Mar. 18, 2020", 3 pgs.
"Brazil Application Serial No. 1120150199690, Office Action dated Jan. 10, 2020", w/ English Translation, 5 pgs.
"Brazil Application Serial No. 1120150200982, Office Action dated Dec. 6, 2019", W/O English Translation, 5 pgs.
"Brazil Application Serial No. 1120150215777, Office Action dated Jan. 10, 2020", W/O English Translation, 5 pgs.
"Brazil Application Serial No. 1120150215939, Office Action dated Jan. 10, 2020", w/ English translation, 5 pgs.
"Brazilian Application Serial No. 1120150219020, Office Action dated Jan. 13, 2020", W/English Translation, 5 pgs.
"European Application Serial No. 14718878.3, Communication Pursuant to Article 94(3) EPC dated Oct. 8, 2019", 2 pgs.
"European Application Serial No. 14718878.3, Office Action dated Dec. 2, 2015", 1 pg.

(56) References Cited

OTHER PUBLICATIONS

"European Application Serial No. 14718878.3, Response filed Feb. 13, 2020 to Communication Pursuant to Article 94(3) EPC dated Oct. 8, 2019", 102 pgs.
"European Application Serial No. 14718878.3, Response filed Apr. 29, 2016 to Communication Pursuant to Rules 161(1) and 162 EPC dated Oct. 22, 2015", 25 pgs.
"European Application Serial No. 14721152.8, Intention to Grant dated May 15, 2017", 50 pgs.
"European Application Serial No. 14721152.8, Intention to Grant dated Oct. 17, 2016", 52 pgs.
"European Application Serial No. 14721152.8, Intention to Grant dated Dec. 13, 2017", 50 pgs.
"European Application Serial No. 14721152.8, Response filed Jan. 19, 2017 to Intention to Grant dated Oct. 17, 2016", 65 pgs.
"European Application Serial No. 14721152.8, Response filed Sep. 25, 2017 to Intention to Grant dated May 15, 2017", 41 pgs.
"European Application Serial No. 14721152.8, Response to Communication pursuant to Rules 161 (1) and 162 EPC filed Apr. 28, 2016", 13 pgs.
"European Application Serial No. 14722049.5, Communication Pursuant to Article 94(3) EPC dated Oct. 18, 2019", 8 pgs.
"European Application Serial No. 14722049.5, Response filed Jan. 15, 2020 to Communication Pursuant to Article 94(3) EPC dated Oct. 18, 2019", 12 pgs.
"European Application Serial No. 14722049.5, Response filed Apr. 29, 2016 to Communication pursuant to Rules 161(1) and 162 EPC dated Oct. 22, 2015", 18 pgs.
"European Application Serial No. 14722475.2, Communication Pursuant to Article 94(3) EPC dated Jan. 30, 2018", 3 pgs.
"European Application Serial No. 14722475.2, Communication Pursuant to Article 94(3) EPC dated Sep. 15, 2016", 9 pgs.
"European Application Serial No. 14722475.2, Response filed Jan. 13, 2017 to Communication Pursuant to Article 94(3) EPC dated Sep. 15, 2016", 34 pgs.
"European Application Serial No. 14722475.2, Response filed Mar. 15, 2018 to Communication Pursuant to Article 94(3) EPC dated Jan. 30, 2018", 29 pgs.
"European Application Serial No. 14722475.2, Response filed Apr. 29, 2016 to Communication Pursuant to Rules 161(1) and 162 EPC dated Oct. 22, 2015", 25 pgs.
"European Application Serial No. 14723592.3, Communication Pursuant to Article 94(3) EPC dated Sep. 15, 2016", 9 pgs.
"European Application Serial No. 14723592.3, Response filed Jan. 11, 2017 to Communication Pursuant to Article 94(3) EPC dated Sep. 15, 2016", 7 pgs.
"European Application Serial No. 14723592.3, Response filed Apr. 25, 2016 to Communication pursuant to Rules 161(1) and 162 EPC dated Oct. 22, 2015", 13 pgs.
"European Application Serial No. 14725288.6, Communication under Rule 164(2)(a) EPC dated Nov. 7, 2019", 6 pgs.
"European Application Serial No. 14725288.6, Response filed Apr. 29, 2016 to Communication pursuant to Rules 161(1) and 162 EPC dated Oct. 22, 2015", 62 pgs.
"European Application Serial No. 18202980.1, Examiner Interview Summary dated Oct. 18, 2019", 5 pgs.
"European Application Serial No. 18202980.1, Extended European Search Report dated Feb. 13, 2019", 5 pgs.
"European Application Serial No. 18202980.1, Office Action dated Nov. 15, 2018", 1 page.
"European Application Serial No. 18213038.5, Extended European Search Report dated Apr. 30, 2019", 11 pgs.
"European Application Serial No. 18213038.5, Response filed Nov. 14, 2019 to Extended European Search Report dated Apr. 30, 2019", 37 pgs.
"India Application Serial No. 7592/DELNP/2015, First Examination Report dated Nov. 13, 2019", w/ English Translation, 7 pgs.
"Indian Application Serial No. 7649/DELNP/2015, First Examination Report dated Jan. 29, 2020", 8 pgs.
"Indian Application Serial No. 8298/DELNP/2015, First Examination Report dated Feb. 11, 2020", 7 pgs.
"International Application Serial No. PCT/US2014/030850, International Preliminary Report on Patentability dated Sep. 24, 2015", 15 pgs.
"International Application Serial No. PCT/US2014/030850, International Search Report dated Jun. 27, 2014", 7 pgs.
"International Application Serial No. PCT/US2014/030850, Written Opinion dated Jun. 27, 2014", 13 pgs.
"International Application Serial No. PCT/US2014/030851, International Preliminary Report on Patentability dated Sep. 24, 2015", 9 pgs.
"International Application Serial No. PCT/US2014/030851, International Search Report dated Jul. 16, 2014", 3 pgs.
"International Application Serial No. PCT/US2014/030851, Written Opinion dated Jul. 16, 2014", 7 pgs.
"International Application Serial No. PCT/US2014/030902, International Preliminary Report on Patentability dated Sep. 24, 2015", 13 pgs.
"International Application Serial No. PCT/US2014/030902, International Search Report dated Jun. 18, 2014", 4 pgs.
"International Application Serial No. PCT/US2014/030902, Written Opinion dated Jun. 18, 2014", 11 pgs.
"International Application Serial No. PCT/US2014/030928, International Preliminary Report on Patentability dated Sep. 24, 2015", 11 pgs.
"International Application Serial No. PCT/US2014/030928, International Search Report dated Jun. 18, 2014", 4 pgs.
"International Application Serial No. PCT/US2014/030928, Written Opinion dated Jun. 18, 2014", 9 pgs.
"International Application Serial No. PCT/US2014/030939, International Preliminary Report on Patentability dated Sep. 24, 2015", 11 pgs.
"International Application Serial No. PCT/US2014/030940, International Search Report dated Oct. 23, 2014", 8 pgs.
"International Application Serial No. PCT/US2014/030940, Written Opinion dated Oct. 23, 2014", 16 pgs.
"International Application Serial No. PCT/US2014/030942, International Preliminary Report on Patentability dated Sep. 24, 2015", 23 pgs.
"Japanese Application Serial No. 2016-502584, Office Action dated Jan. 9, 2018", w/ English Translation, 10 pgs.
"Japanese Application Serial No. 2016-502591, Notification of Reasons for Rejection dated Jan. 5, 2018", W/English Translation, 8 pgs.
"Japanese Application Serial No. 2016-502591, Notification of Reasons for Rejection dated Aug. 27, 2018", W/English Translation, 6 pgs.
"Japanese Application Serial No. 2016-502595, Office Action dated Jan. 9, 2018", w/ English Translation, 13 pgs.
"Korean Application Serial No. 10-2015-7024436, Notice of Preliminary Rejection dated May 5, 2019", w/ English translation, 4 pgs.
"Korean Application Serial No. 10-2015-7024436, Response filed Jul. 5, 2019 to Notice of Preliminary Rejection dated May 5, 2019", w/ English claims, 29 pgs.
"Korean Application Serial No. 10-2015-7024439, Response filed Aug. 29, 2019 to Notice of Preliminary Rejection dated Jul. 16, 2019", w/ English claims, 15 pgs.
"Korean Application Serial No. 10-2015-7024441, Notice of Preliminary Rejection dated May 7, 2019", w/ English translation, 5 pgs.
"Korean Application Serial No. 10-2015-7024441, Response filed Jul. 5, 2019 to Notice of Preliminary Rejection dated May 7, 2019", w/ English claims, 38 pgs.
"Korean Application Serial No. 10-2015-7024466, Final Office Action dated Oct. 30, 2019", w/English Translation, 5 pgs.
"Korean Application Serial No. 10-2015-7024466, Request for Reexamination filed Nov. 29, 2019 to Final Office Action dated Oct. 30, 2019", w/ English claims, 14 pgs.
"Korean Application Serial No. 10-2015-7024466, Response filed Sep. 17, 2019 to Notice of Preliminary Rejection dated Jul. 17, 2019", w/ English claims, 20 pgs.

(56) References Cited

OTHER PUBLICATIONS

"Korean Application Serial No. 10-2015-7024469, Notice of Preliminary Rejection dated May 7, 2019", w/ English translation, 6 pgs.

"Korean Application Serial No. 10-2015-7024469, Response filed Jul. 5, 2019 to Notice of Preliminary Rejection dated May 7, 2019", w/ English claims, 35 pgs.

U.S. Appl. No. 14/215,834 U.S. Pat. No. 9,316,635, filed Mar. 17, 2014, Sheath Fluid Systems and Methods for Particle Analysis in Blood Samples.

U.S. Appl. No. 15/064,129 U.S. Pat. No. 9,470,618, filed Mar. 8, 2016, Sheath Fluid Systems and Methods for Particle Analysis in Blood Samples.

U.S. Appl. No. 15/263,001 U.S. Pat. No. 10,451,612, filed Sep. 12, 2016, Sheath Fluid Systems and Methods for Particle Analysis in Blood Samples.

U.S. Appl. No. 16/561,122, filed Sep. 5, 2019, Sheath Fluid Systems and Methods for Particle Analysis in Blood Samples.

U.S. Appl. No. 14/216,533 U.S. Pat. No. 9,322,752, filed Mar. 17, 2014, Flowcell Systems and Methods for Particle Analysis in Blood Samples.

U.S. Appl. No. 15/047,971 U.S. Pat. No. 9,909,973, filed Feb. 19, 2016, Flowcell Systems and Methods for Particle Analysis in Blood Samples.

U.S. Appl. No. 14/216,811, filed Mar. 17, 2014, Autofocus Systems and Methods for Particle Analysis in Blood Samples.

U.S. Appl. No. 15/880,328 U.S. Pat. No. 10,345,217, filed Jan. 25, 2018, Flowcell Systems and Methods for Particle Analysis in Blood Samples.

U.S. Appl. No. 16/574,693, filed Sep. 18, 2019, Autofocus Systems and Methods for Particle Analysis in Blood Samples.

U.S. Appl. No. 14/217,034 U.S. Pat. No. 10,429,292, filed Mar. 17, 2014, Dynamic Range Extension Systems and Methods for Particle Analysis in Blood Samples.

U.S. Appl. No. 14/216,339 U.S. Pat. No. 9,279,750, filed Mar. 17, 2014, Method and Composition for Staining and Sample Processing.

U.S. Appl. No. 14/775,448 U.S. Pat. No. 9,702,806, filed Sep. 11, 2015, Hematology Systems and Methods.

U.S. Appl. No. 15/645,710 U.S. Pat. No. 10,060,846, filed Jul. 10, 2017, Hematology Systems and Methods.

U.S. Appl. No. 16/037,407, filed Jul. 17, 2018, Hematology Systems and Methods.

"U.S. Appl. No. 16/574,693, Response filed Dec. 2, 2021 to Restriction Requirement dated Oct. 15, 2021", 7 pgs.

"Brazilian Application Serial No. 112015021800-8, Office Action dated Mar. 26, 2020", with English translation, 5 pages.

"Chinese Application Serial No. 201480015388.0, Notice of Reexamination dated May 20, 2020", with English translation, 22 pages.

"Indian Application Serial No. 7591 DELNP 2015, First Examination Report dated Dec. 13, 2019", with English translation, 9 pages.

"Brazilian Application Serial No. 1120150219020, Response filed Apr. 14, 2020 to Office Action dated Jan. 13, 2020", with English claims, 151 pages.

"Brazil Application Serial No. 1120150199690, Response filed Apr. 9, 2020 to Office Action dated Jan. 10, 2020", with English claims, 114 pages.

"Brazilian Application Serial No. 112015021800-8, Response filed Jun. 26, 2020 to Office Action dated Mar. 26, 2020", with English claims, 151 pages.

"Chinese Application Serial No. 201810941307.X, Office Action dated Jun. 22, 2020", with English translation, 33 pages.

"Chinese Application Serial No. 201810805317.0, Office Action dated Jul. 3, 2020", with English translation, 13 pages.

"Indian Application Serial No. 8298 DELNP 2015, Response filed Aug. 6, 2020 to First Examination Report dated Feb. 11, 2020", with English translation, 193 pages.

"Indian Application Serial No. 7649 DELNP 2015, Response filed Jul. 23, 2020 to First Examination Report dated Jan. 29, 2020", 94 pages.

"Chinese Application Serial No. 201480015388.0, Response filed Jul. 30, 2020 to Notice of Reexamination dated May 20, 2020", with English claims, 29 pages.

"Indian Application Serial No. 8082 DELNP 2015, First Examination Report dated Sep. 16, 2020", with English translation, 6 pages.

"Brazilian Application Serial No. 1120150219020, Office Action dated Oct. 15, 2020", with machine English translation, 7 pages.

"Brazilian Application Serial No. 1120150215777, Office Action dated Oct. 16, 2020", with machine English translation, 9 pages.

"Chinese Application Serial No. 201810805317.0, Response filed Oct. 28, 2020 to Office Action dated Jul. 3, 2020", with English claims, 94 pages.

"Chinese Application Serial No. 201810941307.X, Response filed Nov. 5, 2020 to Office Action dated Jun. 22, 2020", with English claims, 15 pages.

"Chinese Application Serial No. 201480015388.0, Notice of Decision of Reexamination—Revoking Decision of Rejection dated Nov. 27, 2020", with machine English translation, 47 pages.

"Chinese Application Serial No. 201480015388.0, Office Action dated Feb. 4, 2021", with English translation, 9 pages.

"Chinese Application Serial No. 201810941307.X, Office Action dated Jan. 27, 2021", with English translation, 32 pages.

"Chinese Application Serial No. 201810805317.0, Office Action dated Feb. 1, 2021", with English translation, 10 pages.

"Brazilian Application Serial No. 1120150219020, Response filed Jan. 8, 2021 to Office Action dated Oct. 15, 2020", with English claims, 132 pages.

"Indian Application Serial No. 8082 DELNP 2015, Response filed Mar. 11, 2021 to First Examination Report dated Sep. 16, 2020", 13 pages.

"Chinese Application Serial No. 201480015388.0, Response filed Apr. 2, 2021 to Office Action dated Feb. 4, 2021", with English claims, 29 pages.

"European Application Serial No. 21158285.3, Extended European Search Report dated Jun. 1, 2021", 13 pgs.

"Chinese Application Serial No. 201810941307.X, Response filed Apr. 2, 2021 to Office Action dated Jan. 27, 2021", with English claims, 16 pages.

"European Application Serial No. 14725288.6, Communication pursuant to Rule 164(2)(b) and Article 94(3) EPC dated Feb. 25, 2020", 13 pgs.

"Chinese Application Serial No. 201810941307.X, Decision of Rejection dated Jun. 11, 2021", with English translation, 31 pages.

"U.S. Appl. No. 16/574,693, Restriction Requirement dated Oct. 15, 2021", 6 pgs.

"U.S. Appl. No. 16/574,693, Non Final Office Action dated Jan. 13, 2022", 12 pgs.

"European Application Serial No. 14722049.5, Communication Pursuant to Article 94(3) EPC dated Feb. 21, 2022", 7 pgs.

"European Application Serial No. 21158285.3, Response Filed Dec. 15, 2021 to Extended European Search Report dated Jun. 1, 2021", 13 pgs.

"U.S. Appl. No. 16/574,693, Final Office Action dated May 12, 2022", 12 pgs.

"U.S. Appl. No. 16/574,693, Response filed Mar. 25, 2022 to Non Final Office Action dated Jan. 13, 2022", 12 pgs.

"European Application Serial No. 14722049.5, Response Filed Mar. 11, 2022 to Communication Pursuant to Article 94(3) EPC dated Feb. 21, 2022", 10 pgs.

"European Application Serial No. 14725288.6, Communication Pursuant to Article 94(3) EPC dated May 13, 2022", 16 pgs.

"U.S. Appl. No. 16/574,693, Response filed Jul. 5, 2022 to Final Office Action dated May 12, 2022", 9 pgs.

* cited by examiner

PIOAL results in more in-focus cells contents (PIOAL particle and/or intracellular organelle alignment liquid)

RBCs in sample stream with
Conventional Sheath

RBCs in sample stream at 20x Magnification
with Conventional Sheath

RBCs in sample stream with PIOAL

RBCs in sample stream at 20x
Magnification with PIOAL

DYNAMIC RANGE EXTENSION SYSTEMS AND METHODS FOR PARTICLE ANALYSIS IN BLOOD SAMPLES

CROSS-REFERENCES TO RELATED APPLICATIONS

This application is a division of U.S. patent application Ser. No. 14/217,034, filed Mar. 17, 2017, which is a nonprovisional of, and claims the benefit of priority to, U.S. Pat. No. 6,799,152 filed Mar. 15, 2013, the content of which is incorporated herein by reference. This application is also related to U.S. patent application Ser. Nos. 14/216,811, 14/216,533, 14/215,834, and 14/216,339, and International Patent Application Nos. PCT/US14/30928, PCT/US14/30902, and PCT/US14/30850, all filed Mar. 17, 2014. The content of each of these filings is incorporated herein by reference.

BACKGROUND OF THE INVENTION

This disclosure relates to the field of apparatus, systems, compositions, and methods for analysis of particles, including imaging of particles in fluid samples, using wholly or partly automated devices to discriminate and quantify particles such as blood cells in the sample. The present disclosure also relates to a particle and/or intracellular organelle alignment liquid (PIOAL) useful for analyzing particles in a sample from a subject, methods for producing the liquid, and methods for using the liquid to detect and analyze particles. Compositions, systems, devices and methods useful for conducting image-based biological fluid sample analysis are also disclosed. The compositions, systems, devices, and methods of the present disclosure are also useful for detecting, counting and characterizing particles in biological fluids such as red blood cells, reticulocytes, nucleated red blood cells, platelets, and for image and morphologically-based white blood cell differential counting, categorization, subcategorization, characterization and/or analysis.

Blood cell analysis is one of the most commonly performed medical tests for providing an overview of a patient's health status. A blood sample can be drawn from a patient's body and stored in a test tube containing an anticoagulant to prevent clotting. A whole blood sample normally comprises three major classes of blood cells including red blood cells (erythrocytes), white blood cells (leukocytes) and platelets (thrombocytes). Each class can be further divided into subclasses of members. For example, five major types or subclasses of white blood cells (WBCs) have different shapes and functions. White blood cells may include neutrophils, lymphocytes, monocytes, eosinophils, and basophils. There are also subclasses of the red blood cell types. The appearances of particles in a sample may differ according to pathological conditions, cell maturity and other causes. Red blood cell subclasses may include reticulocytes and nucleated red blood cells.

A blood cell count estimating the concentration of RBCs, WBCs or platelets can be done manually or using an automatic analyzer. When blood cell counts are done manually, a drop of blood is applied to a microscope slide as a thin smear. Traditionally, manual examination of a dried, stained smear of blood on a microscope slide has been used to determine the number or relative amounts of the five types of white blood cells. Histological dyes and stains have been used to stain cells or cellular structures. For example, Wright's stain is a histologic stain that has been used to stain blood smears for examination under a light microscope. A Complete Blood Count (CBC) can be obtained using an automated analyzer, one type of which counts the number of different particles or cells in a blood sample based on impedance or dynamic light scattering as the particles or cells pass through a sensing area along a small tube. The automated CBC can employ instruments or methods to differentiate between different types of cells that include RBCs, WBCs and platelets (PFTs), which can be counted separately. For example, a counting technique requiring a minimum particle size or volume might be used to count only large cells. Certain cells such as abnormal cells in the blood may not be counted or identified correctly. Small cells that adhere to one another may be erroneously counted as a large cell. When erroneous counts are suspected, manual review of the instrument's results may be required to verify and identify cells.

Automated blood cell counting techniques can involve flow cytometry. Flow cytometry involves providing a narrow flow path, and sensing and counting the passage of individual blood cells. Flow cytometry methods have been used to detect particles suspended in a fluid, such as cells in a blood sample, and to analyze the particles as to particle type, dimension, and volume distribution so as to infer the concentration of the respective particle type or particle volume in the blood sample. Examples of suitable methods for analyzing particles suspended in a fluid include sedimentation, microscopic characterization, counting based on impedance, and dynamic light scattering. These tools are subject to testing errors. On the other hand, accurate characterization of types and concentration of particles may be critical in applications such as medical diagnosis.

In counting techniques based on imaging, pixel data images of a prepared sample that may be passing through a viewing area are captured using a microscopy objective lens coupled to a digital camera. The pixel image data can be analyzed using data processing techniques, and also displayed on a monitor.

Aspects of automated diagnosis systems with flowcells are disclosed in U.S. Pat. No. 6,825,926 to Turner et al. and in U.S. Pat. Nos. 6,184,978; 6,424,415; and 6,590,646, all to Kasdan et al., which are hereby incorporated by reference as if set forth fully herein.

Automated systems using dynamic light scattering or impedance have been used to obtain a complete blood count (CBC): total white blood cell count (WBC), total cellular volume of red blood cells (RBC distribution), hemoglobin HGB (the amount of hemoglobin in the blood); mean cell volume (MCV) (mean volume of the red cells); MPV (mean PLT volume); hematocrit (HCT); MCH (HGB/RBC) (the average amount of hemoglobin per red blood cell); and MCHC (HGB/HCT) (the average concentration of hemoglobin in the cells). Automated or partially automated processes have been used to facilitate white blood cell five part differential counting and blood sample analyses.

Although such currently known particle analysis systems and methods, along with related medical diagnostic techniques, can provide real benefits to doctors, clinicians, and patients, still further improvements are desirable. Embodiments of the present invention provide solutions for at least some of these outstanding needs

BRIEF SUMMARY OF THE INVENTION

Embodiments of the present invention encompass systems and methods for quantifying cells or particles present in a blood fluid sample, using exemplary dynamic or detection range extension techniques.

For example, exemplary embodiments encompass techniques for correcting inaccurate particle counts associated with at least one detection range, based on a parameter such as particle volume. By operating the apparatus as described in the present disclosure, the particles outside the detection range for concentration and/or by volume can be detected and measured accurately.

As used herein, the term "detection limit" or "outside of detection range" associated with a particle counter made in this disclosure will be understood to encompass a range, within which the particle count is more accurate and/or outside of which the particle count is less accurate or even inoperable. A detection range may include an upper and/or a lower detection limit, typically expressed as a maximum or minimum concentration, but also possibly expressed as a maximum or minimum frequency at which particles are counted within a given tolerance of accuracy. Hence, embodiments of the present invention encompass systems and methods for parallel flowcell and impedance analysis of blood fluid samples for quantification of sparse and/or copious species counts.

A detection range can be based on the concentration, which may include a local concentration, and/or other specified criterion or criteria. For example, a particle such as a blood cell or fragment smaller than a normal PLT (i.e., having a diameter less than 2 μm) may be difficult to detect and count accurately in a particle counter. An abnormal cell larger than a regular white cell (i.e., having a diameter higher than 15 μm) may be difficult to detect and count accurately in a particle counter. In addition, in high concentrations, RBCs and PLTs may be difficult to count accurately. Even after dilution, RBCs and PLTs may aggregate to form clumps, resulting in false readings of particle counts obtained using a particle counter. Furthermore, it is difficult to provide an accurate count of some immature or abnormal blood cells present in the sample at low concentrations.

As an example, by using the apparatus described herein, the detection range of measurement, the upper detection limit for WBCs can be extended up to 300,000, 400,000, 500,000, 600,000, 700,000, 800,000, 900,000, or 1,000,000 per (unit volume) in some embodiments. The lower detection limit for PLTs can be extended lower than 20,000, 19,000, 18,000,17,000, 16,000, 15,000, 14,000, 13,000, 12,000, 11,000, 10,000, 9,500, 9,000, 8,500, 8,000, 7,500, 7,000, 6,500, 6,000, 5,500, 5,000, 4,500, 4,000, 3,500, 3,000, 2,500, 2,000, 1,500 or 1,000, or 500 per μl in some embodiments.

Relatedly, exemplary embodiments encompass techniques for correcting inaccurate results obtained in a particle counter by differentiating different classes (including members of each class) of particles detected in one channel. As described herein, some particles have similar volume or morphology and may be detected in one channel. For example, "giant" PLTs, PLT aggregates or clumps, and nucleated RBCs may be counted as "WBCs" in one channel designed to detect WBCs. In addition, other species such as unlysed cells, cryoglobulin, heinz bodies, and malaria parasite may be counted as "WBCs" to give a WBC count higher than that actually exists in the sample. Similarly, high concentration of WBCs and giant PLTs may be counted as "RBCs" and result in a RBC count higher than the actual value. Presence of microcytic red cells, red cell inclusions, white cell fragments, dust particles, hemolysis/Schistocytes and even electronic/electric noises may result in a count of PLTs higher than actual. On the other hand, clotting and smudge cells within the same class or confusion of one class of cells with another class may result in inaccurate and lower count of the corresponding class of cells on the particle counter.

In some aspects of the methods of this disclosure a first category and/or subcategory of particles is present in the sample at a concentration above a detection range applicable to the first category and/or subcategory of particles; and a second category and/or subcategory of particles is present in the sample within a detection range applicable to the second category and/or subcategory of particles. In other aspects of the methods of this invention, the first category and/or subcategory of particles is present in the sample at a concentration below a detectable range applicable to the first category and/or subcategory of particles, and the second category and/or subcategory of particles is present in the sample within a detection range applicable to the second category and/or subcategory of particles. In other aspects, the first category and/or subcategory of particles comprises at least one type of abnormal blood cells, immature blood cells, clumped blood cells, blood cells having diameter larger than 15 microns, and blood cells having diameter smaller than 2 microns; and the second category and/or subcategory of particles comprises white blood cells.

By operating the apparatus as described in this disclosure, those particles which are miscounted as another type of particle in one channel of the particle counter can be measured separately and accurately. Exemplary methods can be also used to determine particle count or concentrations of particles which cannot be detected accurately on the particle counter. These particles include but are not limited to the particles outside normal volume ranges and/or particles present at concentrations near or outside the high or low end of concentrations detectable on the particle counter. Relatedly, by operating a system apparatus as described, especially comprising a particle counter and an image analyzer in combination with the exemplary particle contrast agent compositions and PIOAL as described in this disclosure, some particles which may be miscounted as another type of particle in one channel of the particle counter can be measured separately and accurately. The methods of this invention can be also used in some instances to determine particle count or concentrations of particles which cannot be detected accurately on the particle counter. These particles include but are not limited to the particles outside a detection range and/or particles present at concentrations near or beyond the high or low end of concentrations detectable on the particle counter. This is done by applying information obtained from the image analyzer.

Overall, by operating an apparatus as disclosed herein, for example using exemplary particle contrast agent compositions and PIOAL sheath fluids, analysis of a sample containing particles such as blood cells or other fragments can be performed in detection ranges that are outside the nominal detection range for a particle counter. Relatedly, using systems and compositions as described herein, analysis of a blood fluid sample can be performed in extended detection ranges based on a parameter such as concentration or particle volume. The extended detection ranges can outside the detection range for a particle counter.

In some embodiments, a system or apparatus can include a particle counter. In other embodiments this particle counter has at least one detection range. In certain aspects, the analyzer and the processor can be configured to provide additional information to correct testing errors associated with the particle counter, and further determine accurate particle count or concentration of different categories and/or subcategories of particles in the sample. Provided that information is available from the particle counter and the analyzer about the counts, one or more ratios, and/or distribution over at least two of the categories and/or subcategories of particles, then errors in counts, categorization and/or subcategorization from the particle counter can be corrected, and counts, categories and/or subcategories can be derived that were not initially reported by the particle counter.

Embodiments of the present invention encompass systems and methods for quantifying cells or particles present in a blood fluid sample, using exemplary dynamic or detection range extension techniques.

For example, exemplary embodiments encompass techniques for correcting inaccurate particle counts associated with at least one detection range, based on a parameter such as particle volume. By operating the apparatus as described in the present disclosure, the particles outside the detection range for concentration and/or by volume can be detected and measured accurately.

As used herein, the term "detection limit" or "outside of detection range" associated with a particle counter made in this disclosure will be understood to encompass a range, within which the particle count is more accurate and/or outside of which the particle count is less accurate or even inoperable. A detection range may include an upper and/or a lower detection limit, typically expressed as a maximum or minimum concentration, but also possibly expressed as a maximum or minimum frequency at which particles are counted within a given tolerance of accuracy. Hence, embodiments of the present invention emcompass systems and methods for parallel flowcell and impedance analysis of blood fluid samples for quantification of sparse and/or copious species counts.

A detection range can be based on the concentration, which may include a local concentration, and/or other specified criterion or criteria. For example, a particle such as a blood cell or fragment smaller than a normal PLT (i.e., having a diameter less than 2 μm) may be difficult to detect and count accurately in a particle counter. An abnormal cell larger than a regular white cell (i.e., having a diameter higher than 15 μm) may be difficult to detect and count accurately in a particle counter. In addition, in high concentrations, RBCs and PLTs may be difficult to count accurately. Even after dilution, RBCs and PLTs may aggregate to form clumps, resulting in false readings of particle counts obtained using a particle counter. Furthermore, it is difficult to provide an accurate count of some immature or abnormal blood cells present in the sample at low concentrations.

As an example, by using the apparatus described herein, the detection range of measurement, the upper detection limit for WBCs can be extended up to 300,000, 400,000, 500,000, 600,000, 700,000, 800,000, 900,000, or 1,000,000 per (unit volume) in some embodiments. The lower detection limit for PLTs can be extended lower than 20,000, 19,000, 18,000, 17,000, 16,000, 15,000, 14,000, 13,000, 12,000, 11,000, 10,000, 9,500, 9,000, 8,500, 8,000, 7,500, 7,000, 6,500, 6,000, 5,500, 5,000, 4,500, 4,000, 3,500, 3,000, 2,500, 2,000, 1,500 or 1,000, or 500 per μl in some embodiments.

Relatedly, exemplary embodiments encompass techniques for correcting inaccurate results obtained in a particle counter by differentiating different classes (including members of each class) of particles detected in one channel. As described herein, some particles have similar volume or morphology and may be detected in one channel. For example, "giant" PLTs, PLT aggregates or clumps, and nucleated RBCs may be counted as "WBCs" in one channel designed to detect WBCs. In addition, other species such as unlysed cells, cryoglobulin, heinz bodies, and malaria parasite may be counted as "WBCs" to give a WBC count higher than that actually exists in the sample. Similarly, high concentration of WBCs and giant PLTs may be counted as "RBCs" and result in a RBC count higher than the actual value. Presence of microcytic red cells, red cell inclusions, white cell fragments, dust particles, hemolysis/Schistocytes and even electronic/electric noises may result in a count of PLTs higher than actual. On the other hand, clotting and smudge cells within the same class or confusion of one class of cells with another class may result in inaccurate and lower count of the corresponding class of cells on the particle counter.

In some aspects of the methods of this disclosure a first category and/or subcategory of particles is present in the sample at a concentration above a detection range applicable to the first category and/or subcategory of particles; and a second category and/or subcategory of particles is present in the sample within a detection range applicable to the second category and/or subcategory of particles. In other aspects of the methods of this invention, the first category and/or subcategory of particles is present in the sample at a concentration below a detectable range applicable to the first category and/or subcategory of particles, and the second category and/or subcategory of particles is present in the sample within a detection range applicable to the second category and/or subcategory of particles. In other aspects, the first category and/or subcategory of particles comprises at least one type of abnormal blood cells, immature blood cells, clumped blood cells, blood cells having diameter larger than 15 microns, and blood cells having diameter smaller than 2 microns; and the second category and/or subcategory of particles comprises white blood cells.

By operating the apparatus as described in this disclosure, those particles which are miscounted as another type of particle in one channel of the particle counter can be measured separately and accurately. Exemplary methods can be also used to determine particle count or concentrations of particles which cannot be detected accurately on the particle counter. These particles include but are not limited to the particles outside normal volume ranges and/or particles present at concentrations near or outside the high or low end of concentrations detectable on the particle counter. Relatedly, by operating a system apparatus as described, especially comprising a particle counter and an image analyzer in combination with the exemplary particle contrast agent compositions and PIOAL as described in this disclosure, some particles which may be miscounted as another type of particle in one channel of the particle counter can be measured separately and accurately. The methods of this invention can be also used in some instances to determine particle count or concentrations of particles which cannot be detected accurately on the particle counter. These particles include but are not limited to the particles outside a detection range and/or particles present at concentrations near or beyond the high or low end of concentrations detectable on the particle counter. This is done by applying information obtained from the image analyzer.

Overall, by operating an apparatus as disclosed herein, for example using exemplary particle contrast agent compositions and PIOAL sheath fluids, analysis of a sample containing particles such as blood cells or other fragments can be performed in detection ranges that are outside the nominal detection range for a particle counter. Relatedly, using systems and compositions as described herein, analysis of a blood fluid sample can be performed in extended detection ranges based on a parameter such as concentration or particle volume. The extended detection ranges can outside the detection range for a particle counter.

In some embodiments, a system or apparatus can include a particle counter. In other embodiments this particle counter has at least one detection range. In certain aspects, the analyzer and the processor can be configured to provide additional information to correct testing errors associated with the particle counter, and further determine accurate particle count or concentration of different categories and/or subcategories of particles in the sample. Provided that information is available from the particle counter and the analyzer about the counts, one or more ratios, and/or distribution over at least two of the categories and/or subcategories of particles, then errors in counts, categorization and/or subcategorization from the particle counter can be corrected, and counts, categories and/or subcategories can be derived that were not initially reported by the particle counter.

In one aspect, embodiments of the present invention encompass methods for measuring a quantity of a first cell type in a blood fluid sample. The sample can include a second cell type. Exemplary methods include determining a population of the second cell type in a first volume of the sample by flowing the first volume through a hematology cell counter, acquiring images of a first number of the first type cells and a second number of the second cell types by injecting a second volume of the sample into a sheath fluid flowing within a flowcell so as to provide a sample stream having a thickness and a width greater than the thickness, the acquired images being acquired along an image path traversing the thickness of the sample stream, determining a ratio of the first number of the first cell type to the second number of the second cell types using the acquired images, and calculating a cell quantity measure of the first cell type in the sample using the ratio and the population of the second cell type. In some cases, the cell quantity measure includes a cell concentration for the first cell type in the blood fluid sample. In some cases, the cell quantity measure includes a cell count for the first cell type in the blood fluid sample. In some cases, the cell counter has a first accuracy associated with counting of the first cell type and a second accuracy associated with counting the second cell type, the second accuracy being superior to the first accuracy. In some cases, the hematology cell counter has a desired accuracy range, the desired accuracy range extending between a minimum population of cells in the first volume and a maximum population of cells in the first volume, wherein the determined population of the second cell type in the volume is within the desired accuracy range, and wherein the calculated cell quantity measure of the first cell type of the sample is outside the desired accuracy range. In some cases, methods include determining a population of the first cell type in the first volume of the sample as a result of flowing the first volume through the hematology cell counter, wherein the determined population of the first cell type in the first volume is above or below a desired accuracy range for the first cell type, and is different from the calculated cell quantity measure of the first cell type. In some cases, the determined population of the first cell type is zero. In some cases, the determined population of the first cell type is greater than zero. In some cases, the hematology cell counter includes a sensor mechanism that detects a change in electrical impedance in response to a second type cell flowing through the cell counter. In some cases, the hematology cell counter includes a sensor mechanism that detects an obstruction of a light path in response to a second type cell flowing through the cell counter. In some cases, the hematology cell counter has a minimum detectable concentration limit and a maximum detectable concentration limit for the first cell type, and a minimum detectable concentration limit and a maximum detectable concentration limit for the second cell type, the determined population of the second cell type is based on a detected concentration parameter for the second cell type that is above the minimum limit and below the maximum limit for the second cell type, and the first cell type is present at a concentration that is either below the minimum limit or above the maximum limit for the first cell type. In some cases, the hematology cell counter has a minimum detectable volume limit and a maximum detectable volume limit for the first cell type, and a minimum detectable volume limit and a maximum detectable volume limit for the second cell type, the determined population of the second cell type is based on a detected volume parameter for the second cell type that is above the minimum limit and below the maximum limit for the second cell type, and the first cell type is present at a volume parameter that is either below the minimum limit or above the maximum limit for the first cell type. In some cases, the hematology cell counter has a minimum detectable size limit and a maximum detectable size limit for the first cell type, and a minimum detectable size limit and a maximum detectable volume size for the second cell type, the determined population of the second cell type is based on a detected size parameter for the second cell type that is above the minimum limit and below the maximum limit for the second cell type, and the first cell type is present at a size parameter that is either below the minimum limit or above the maximum limit for the first cell type. In some cases, the determination of the population of the second cell type in the first volume of the sample involves grouping together cells of the first cell type and cells of the second cell type. In some cases, methods include calculating a cell quantity measure of the second cell type in the sample using the ratio and the population of the second cell type. In some cases, the determination of the population of the second cell type in the first volume of the sample comprises grouping together cells of the first cell type and cells of the second cell type, wherein the methods further includes determining a population of the first cell type in the first volume of the sample as a result of flowing the first volume through the hematology cell counter, and wherein the calculation of the cell quantity measure of the first cell type in the sample uses the ratio, the population of the second cell type, and the population of the first cell type.

In another aspect, embodiments of the present invention encompass systems for measuring a quantity of a first cell type in a blood fluid sample. The sample can include a second cell type. Exemplary systems include a hematology cell counter having a channel and an output, the output operatively coupled to the channel so as to generate signals indicative of a population of the second cell type in a first volume of the sample flowing through the channel, a flowcell configured to facilitate flow of a sample stream, the sample stream having a second volume of the sample and a sheath fluid, and having a thickness and a width greater than the thickness, an imaging apparatus configured to acquire images of a first number of the first type cells and a second number of the second type cells, the acquired images being acquired along an image path traversing the thickness of the sample stream, a processor, an image analysis module having a tangible medium embodying machine-readable code executed on the processor for determining a ratio of the first number of the first cell type to the second number of the second cell types using the acquired images, and a cell quantity module comprising a tangible medium embodying machine-readable code executed on the processor for calculating a cell quantity measure of the first cell type in the sample using the ratio and the signals indicative of a population of the second cell type. In some cases, the processor is coupled to the hematology cell counter to receive signals indicative of the population of the second cell type. In some cases, the processor is coupled to the imaging apparatus to receive the acquired images. In some cases, the flowcell and the imaging apparatus are components of a hematology analyzer that performs combined viscosity and geometric hydrofocusing for imaging cells in the blood fluid sample. In some cases, a viscosity difference between the sheath fluid and the blood fluid sample, in combination with a decrease in flowpath size of the flowcell, is effective to hydrofocus the sample stream at an image capture site of the flowcell.

The above described and many other features and attendant advantages of embodiments of the present invention will become apparent and further understood by reference to the following detailed description when considered in conjunction with the accompanying drawings.

BRIEF DESCRIPTION OF THE DRAWINGS

FIGS. 4A-1 and 4A-2 depict cross-section views of sheath fluid (e.g. PIOAL) envelope and sample fluidstream dimensions within a flowcell at a cannula exit port and an image capture site, respectively, according to embodiments of the present invention.

DETAILED DESCRIPTION OF THE INVENTION

Figure 1:
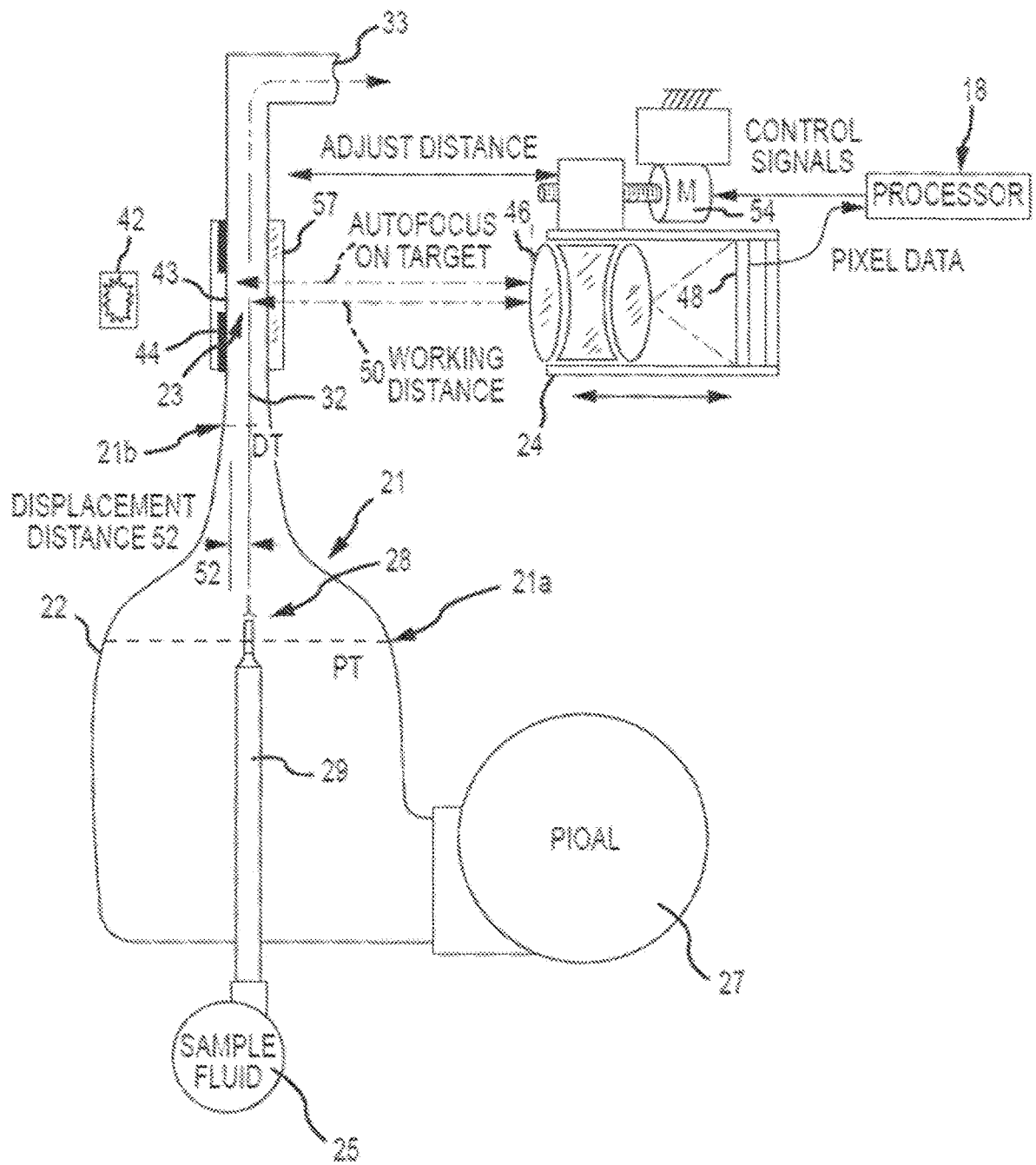
FIG. 1 is a schematic illustration, partly in section and not to scale, showing operational aspects of an exemplary flowcell, autofocus system and high optical resolution imaging device for sample image analysis using digital image processing.

The present disclosure relates to apparatus, systems, compositions, and methods for analyzing a sample containing particles. In one embodiment, the invention relates to an automated particle imaging system which comprises an analyzer which may be, for example, a visual analyzer. In some embodiments, the visual analyzer may further comprise a processor to facilitate automated analysis of the images.

According to this disclosure, a system comprising a visual analyzer is provided for obtaining images of a sample comprising particles suspended in a liquid. The system may be useful, for example, in characterizing particles in biological fluids, such as detecting and quantifying erythrocytes, reticulocytes, nucleated red blood cells, platelets, and white blood cells, including white blood cell differential counting, categorization and subcategorization and analysis. Other similar uses such as characterizing blood cells from other fluids are also contemplated.

The discrimination of blood cells in a blood sample is an exemplary application for which the subject matter is particularly well suited. The sample is prepared by automated techniques and presented to a high optical resolution imaging device as a thin ribbon-shaped sample stream to be imaged periodically while the ribbon-shaped sample stream flows across a field of view. The images of the particles (such as blood cells) can be distinguished from one another, categorized, subcategorized, and counted, using pixel image data programmed processing techniques, either exclusively automatically or with limited human assistance, to identify and count cells or particles. In addition to the cell images, which can be stored and made available in the case of unusual or critical features of particles, the output data includes a count of the occurrences of each particular category and/or subcategory of cell or particle distinguished in the recorded sample images.

The counts of the different particles found in each image can be processed further, for example used to accumulate accurate and statistically significant ratios of cells of each distinguished category and/or subcategory in the sample as a whole. The sample used for visual discrimination can be diluted, but the proportions of cells in each category and/or subcategory are represented in the diluted sample, particularly after a number of images have been processed.

The apparatus and methods disclosed herein are useful in discriminating and quantifying cells in samples based on visual distinctions. The sample can be a biological sample, for example, a body fluid sample comprising white blood cells, including without limitation, blood, serum, bone marrow, lavage fluid, effusions, exudates, cerebrospinal fluid, pleural fluid, peritoneal fluid, and amniotic fluid. In some embodiments, the sample can be a solid tissue sample, e.g., a biopsy sample that has been treated to produce a cell suspension. The sample may also be a suspension obtained from treating a fecal sample. A sample may also be a laboratory or production line sample comprising particles, such as a cell culture sample. The term sample may be used to refer to a sample obtained from a patient or laboratory or any fraction, portion or aliquot thereof. The sample can be diluted, divided into portions, or stained in some processes.

In one aspect, the systems, compositions and methods of this disclosure provide surprisingly high quality images of cells in a flow. In one aspect, the visual analyzer can be used in methods of this disclosure to provide automated image based WBC differential counting. In certain embodiments, the methods of this disclosure relate to automated identification of visual distinctions, including morphological features and/or abnormalities for determining, diagnosing, prognosing, predicting, and/or supporting a diagnosis of whether a subject is healthy or has a disease, condition, abnormality and/or infection and/or is responsive or non-responsive to treatment. The system may further comprise a particle counter in some embodiments. Applications include categorizing and/or subcategorizing, and counting cells in a fluid sample, such as a blood sample. Other similar uses for counting additional types of particles and/or particles in other fluid samples are also contemplated. The system, compositions, and methods of this invention can be used for real-time categorization and subcategorization and viewing of images using any suitable automated particle recognition algorithm. The captured images for each sample can be stored to be viewed at a later date.

In another aspect, the apparatus, compositions, and methods of this invention provide surprisingly more accurate image based cell categorization and subcategorization and flagging which reduces the manual review rate compared to the manual review rate when using current automated analyzers. The systems, compositions, and methods reduce the manual review rate and permit the manual review to be performed on the instrument. In addition, the systems, compositions, and methods of this disclosure also reduce the percentage of samples flagged during automated analysis as requiring manual review.

The present disclosure further relates to systems, methods and compositions for combining a complete blood count (CBC) counter with an analyzer, such as a visual analyzer, in order to obtain a CBC and an image based expanded white blood cell differential count and an image based expanded platelet count, thereby extending the effective detection range for counting platelets.

Accordingly, in some embodiments, the present disclosure provides an apparatus and a method for analyzing a sample containing particles, for example, blood cells. According to this disclosure, a visual analyzer is provided for obtaining images of a sample comprising particles suspended in a liquid. In some embodiments, the visual analyzer comprises a flowcell and an autofocus component, in which a liquid sample containing particles of interest is caused to flow through a flowcell having a viewport through which a camera coupled to an objective lens captures digital images of particles. The flowcell is coupled to a source of sample fluid, such as a diluted and/or treated blood sample or other bodily fluid sample as described herein, and to a source of a clear sheath fluid, or particle and/or intracellular organelle alignment liquid (PIOAL).

In one embodiment, the apparatus also comprises a particle counter having at least one detection range, as well as an analyzer, and a processor. The analyzer and the processor are configured to provide additional information to correct counting, categorization, and subcategorization errors associated with the particle counter, and further determine accurate particle count or concentration of different categories and/or subcategories of particles in the sample.

The instant disclosure provides methods and compositions useful for particle and/or intracellular organelle alignment in conducting image-based sample analysis. In some embodiments, this disclosure relates to methods and compositions for combined counting and imaging system with the ability to perform a complete blood count (CBC) and an image based expanded white blood cell (WBC) differential able to identify and count cell types, such as WBCs, RBCs, and/or platelets, including, for example, neutrophils, lymphocytes, monocytes, eosinophils, basophils, reticulocytes, nucleated RBCs, blasts, promyelocytes, myelocytes, or metamyelocytes, and to provide image based information for WBC counts and morphologies, red blood cell (RBC) counts and morphologies and platelet (PLT) counts and morphologies.

In other embodiments, this disclosure relates to a PIOAL that can be used in image based analysis of particles as described herein. Cell category and/or subcategory count in blood samples is used in this disclosure as nonlimiting examples of the sort of samples that may be analyzed. In some embodiments, cells present in samples may also include bacterial or fungal cells as well as white blood cells, red blood cells and/or platelets. In some embodiments, particle suspensions obtained from tissues or aspirates may be analyzed.

The discrimination of blood cells in a blood sample is an exemplary application for which the subject matter is particularly well suited. The sample is prepared by automated techniques and presented to a high optical resolution imaging device as a ribbon-shaped sample stream to be imaged periodically while the sample flows across a field of view. The images of the particles (such as blood cells) can be distinguished from one another, categorized, subcategorized, and/or counted, using pixel image data programmed processing techniques, either exclusively automatically or with limited human assistance, to identify and count cells or particles. In addition to the cell images, which can be stored and made available in the case of unusual or critical features, the output data includes a count of the occurrences of each particular category and/or subcategory of cell or particle distinguished in the recorded sample images. The counts of the different particles found in each image can be processed further, for example used to accumulate accurate and statistically significant proportionate ratios, or functions thereof of cells of each distinguished category and/or subcategory in the sample as a whole. The sample used for visual discrimination can also be highly diluted, but the proportions of cells in each category and/or subcategory are represented in the distribution for the diluted sample, particularly after a number of images have been processed.

In some aspects, samples are presented, imaged and analyzed in an automated manner. In the case of blood samples, the sample may be substantially diluted with water or saline solution, which reduces the extent to which the view of some cells might be hidden by other cells in an undiluted or less-diluted sample. The cells can be treated with agents that enhance the contrast of some cell aspects, for example using permeabilizing agents to render cell membranes permeable, and histological stains to adhere in and to reveal features, such as granules and the nucleus. In some embodiments it may be desirable to stain an aliquot of the sample for counting and characterizing particles which include reticulocytes, nucleated red blood cells, and platelets, and for white blood cell differential, characterization and analysis. In other embodiments, samples containing red blood cells may be diluted before introduction to the flowcell and imaging.

The particulars of sample preparation apparatus and methods for sample dilution, permeabilizing and histological staining, generally are accomplished using precision pumps and valves operated by one or more programmable controllers, and are not central to this disclosure. Examples can be found in patents assigned to International Remote Imaging Systems, Inc., such as U.S. Pat. No. 7,319,907, concerning programmable controls. Likewise, techniques for distinguishing among certain cell categories and/or subcategories by their attributes such as relative size and color can be found in U.S. Pat. No. 5,436,978 in connection with white blood cells. The disclosures of these patents are hereby incorporated by reference.

To facilitate the capacity, speed and effectiveness by which particles such as cells are categorized and/or subcategorized, it is advantageous to provide clear high quality images of the blood cells for automated analysis by the data processing system. According to the present disclosure, a prepared sample stream is arranged in a thin ribbon having a stable position between opposite walls of a flowcell. The positioning of the sample stream and its flattening into a thin ribbon shape may be achieved by flow between layers of a PIOAL introduced into the flowcell that differs in viscosity from the sample fluid and is flowed through a symmetrical flow channel.

The PIOAL has a suitable viscosity and density, and flow rates at the point of introduction to the flowcell of the sample are such that the sample fluid flattens into a thin ribbon. The ribbon-shaped sample stream is carried along with the PIOAL, to pass in front of a viewing port where an objective lens and a light source are arranged to permit viewing of the ribbon-shaped sample stream. The sample fluid is introduced, for example, injected at a point where the flowpath of the PIOAL narrows symmetrically. As a result, the sample fluid stream is flattened and stretched into a thin ribbon. A PIOAL of this disclosure may be used as the sheath fluid with any visual analyzer of this disclosure. In one embodiment, the PIOAL can be introduced into an end of the flowcell to carry along the sample fluid toward the discharge.

The dimension of the ribbon-shaped sample stream in the viewing zone is affected by geometric thinning of the PIOAL flowpath and differential linear velocity of the sample fluid and PIOAL resulting in thinning and stretching of the ribbon-shaped sample stream. The initial differential linear velocity of the sample to PIOAL may range from 0.5:1 to 5:1. The PIOAL flowpath cross section may be thinned by reducing the depth by a factor of about 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 125:1, 130:1, 140:1, 150:1, 160:1, 170:1, 180:1, 190:1, or 200:1. In one embodiment, the geometric thinning is 40:1. In one embodiment, the geometric thinning is 30:1. Factors taken into account are transit time through the flowcell, desired rate of sample throughput, achieving a ribbon-shaped sample stream thickness comparable to particle size, obtaining alignment of particles and organelles, achieving in focus content of particles, balancing pressure, flow, and viscosity within operational limits, optimizing ribbon-shaped sample stream thickness, obtaining a desired linear velocity, manufacturability considerations, and volumes of sample and PIOAL required.

The length and volume of the cannula and the cross-section flattening may be selected to reduce the period of sample flow instability, thereby increasing throughput. In some embodiments the period of flow instability may be less than about 3, 2.75, 2.5, 2.25, 2, 1.75, 1.5 1.25, or less than about 1 second. A smaller cannula volume may also reduce the time and volume of diluent needed to clean the cannula between sample runs. In some embodiments the transit time through the flowcell is 1, 2, 3, or 4 seconds, or any range in between any two of those times. In some embodiments the transit time may be less than 4, 3 or 2 seconds.

The viscosities and the flow rates of the sample fluid and the PIOAL and the contour of the flowcell are arranged such that the PIOAL flow flattens and stretches the sample flow into a flat ribbon consistently through the viewing zone at a dependable location. The sample fluid stream may be compressed to approximately 2 to 3 µm in fluid flow thickness. Several blood cell types have diameters larger than the stream thickness. Sheer forces in the direction parallel to the direction of the flow cause an increase of an image projection of the particles under imaging conditions in the focal plane of the high optical resolution imaging device and/or causing the intraparticle structures, for example, intracellular structures, organelles or lobes, to be positioned, repositioned, and/or better-positioned to be substantially parallel to the direction of flow. The high optical resolution imaging device depth of field is up to 7 µm, for example, 1-4 µm.

The flow cross section of the PIOAL, with the ribbon-shaped sample stream carried along, is constant through a viewing zone in front of a viewing port through which the objective lens is directed. The objective lens may be the objective component of a high optical resolution imaging device or the digital image capture device. The ribbon-shaped sample stream follows a path across the viewing zone at a known and repeatable position within the flowcell, for example, at a known and repeatable distance from two walls of the flowcell, being discharged downstream.

Optical information from the particles in the sample are detected by a detecting section in the analyzer, when the ribbon-shaped sample stream is carried through the viewing zone in front of the viewing port, thereby generating data from the particles/cells contained in the sample. The use of this analyzer allows capture, processing, categorization and subcategorization and counting of cells and/or particles contained in samples. The PIOAL liquid can be prepared by the addition of viscosity modifying agent, buffer agent, pH adjusting agent, antimicrobial agent, ionic strength modifier, surfactant, and/or a chelating agent. Exemplary functional components and/or features of the analyzer in the present disclosure can include, for example, the ability to acquire and/or process data from image analysis, sample staining processing, image processing, and/or particle image identification, counting, and/or categorization and subcategorization.

In one embodiment this disclosure is based on the surprising and unexpected discovery that the addition of a suitable amount of a viscosity agent in the PIOAL significantly improves particle/cell alignment in a flowcell, leading to a higher percentage of in-focus cells, or cellular components, and higher quality images of cells and/or particles in flow. The addition of the viscosity agent increases the shear forces on cells like RBCs, which improves the alignment of the cells in a plane substantially parallel to the flow direction, which results in image optimization. This also results in positioning, repositioning, and/or better-positioning of intraparticle structures such as intracellular structures, organelles or lobes substantially parallel to the direction of flow, which results in image optimization. The viscosity agent also reduces misalignment of cells, generally, but not limited to cells that are smaller in diameter than the flow stream.

Alignment of cells that are smaller in diameter than the flow stream, for example, red blood cells may be obtained by for example, increasing the viscosity of the PIOAL, or by increasing the flow speed ratio. This results in alignment of the RBCs parallel to the direction of the flow. In some embodiments, a reduction in RBC misalignment and/or increase in RBC alignment is achieved by increasing the viscosity of the PIOAL.

The ribbon-shaped sample stream thickness can be affected by the relative viscosities and flow rates of the sample fluid and the PIOAL. The source of the sample and/or the source of the PIOAL, for example comprising precision displacement pumps, can be configured to provide the sample and/or the PIOAL at controllable flow rates for optimizing the dimensions of the ribbon-shaped sample stream, namely as a thin ribbon at least as wide as the field of view of the high optical resolution imaging device or the digital image capture device.

The flow cross section of the PIOAL, with the ribbon-shaped sample stream carried along, is constant through a viewing zone in front of a viewing port through which the high optical resolution imaging device is directed. The ribbon-shaped sample stream follows a path across the viewing zone at a known and repeatable distance from either of the front and rear walls of the flowcell, being discharged downstream of that.

The term high optical resolution imaging device can include devices that are capable of obtaining particles images with sufficient visual distinctions to differentiate morphological features and/or changes. Exemplary high optical resolution imaging devices can include devices with an optical resolution of 1 um or lower, including for example, 0.4 to 0.5 um, such as for example, 0.46 um.

In some embodiments, the images obtained in any of the compositions and/or methods of this invention may be digitized images. In some embodiments, the images obtained are microscopy images. In certain embodiments, the images may be obtained manually. In other embodiments, at least part of the procedure for obtaining the images is automated. In some embodiments, the images may be obtained using a visual analyzer comprising a flowcell, a high optical resolution imaging device or the digital image capture device, optionally with an autofocus feature.

In one embodiment, the images provide information relating to the cytosolic, cell nucleus and/or nuclear components of the cell. In one embodiment, the images provide information relating to the granular component and/or other morphological features of the cell. In one embodiment, the images provide information relating to cytosolic, nuclear and/or granular components of the cell. The granular and/or nuclear images and/or features are determinative for cell categorization and subcategorization both independently or in combination with each other.

In one aspect of the methods of this invention, the cells contacted with particle contrast agent composition and/or imaged are nucleated red blood cells. In yet another aspect, the methods of this invention relate to a method for performing image-based red blood cell categorization and subcategorization comprising: a) imaging a portion of the red blood cells; and b) determining the morphology of the imaged red blood cells. As used herein, red blood cells (RBC) can include, for example, normal or abnormal red blood cells, reticulocytes, nucleated red blood cells, and/or malaria-infected cells. In some embodiments, the imaging is performed using the apparatus of this disclosure such as an apparatus comprising a particle counter, a visual analyzer and a processor.

As used herein, an exemplary complete blood count (CBC) can include a test panel typically requested by a doctor or other medical professional that provides information about the particles and/or cells in a patient's blood sample. Exemplary cells that circulate in the bloodstream can be generally divided into three types: including but not limited to, for example, white blood cells (e.g., leukocytes), red blood cells (e.g., erythrocytes), and platelets (e.g., thrombocytes).

As used herein, abnormally high or low counts may indicate the presence of disease, disorder, and/or condition. Thus, a CBC is one of the commonly performed blood tests in medicine, as it can provide an overview of a patient's general health status. Accordingly, a CBC is routinely performed during annual physical examinations.

As used herein, typically a phlebotomist collects the blood sample from the subject, the blood is generally drawn into a test tube typically containing an anticoagulant (e.g., EDTA, sometimes citrate) to stop it from clotting. The sample is then transported to a laboratory. Sometimes the sample is drawn off a finger prick using a Pasteur pipette for immediate processing by an automated counter. In one embodiment, the particle image is acquired while the particle is enveloped in a sheath fluid or PIOAL. In certain embodiments, the blood sample may be viewed on a slide prepared with a sample of the patient's blood under a microscope (a blood film, or peripheral smear). In certain embodiments, the complete blood count is performed by an automated analyzer.

As used herein, in general, blood analyzers can aspirate a very small amount of the specimen through narrow tubing. Sensors can detect the count and/or the number of cells passing through the tubing, and can identify the type of cell. Exemplary sensors may include detectors of light (e.g., visible, UV or IR) and/or electrical impedance. Exemplary detection parameters may include size, volume, and/or cellular features. In certain embodiments, the sensors can detect visible and non-visible light in a wavelength spectrum ranging from about 200 nm to about 10000 nm. In certain embodiments, the sensors can detect a wavelength of between about between 380 nm and about 760 nm, As used herein, data/parameters of a blood count can include, for example, total red blood cells; hemoglobin—the amount of hemoglobin in the blood; hematocrit or packed cell volume (PCV); mean corpuscular volume (MCV)—the average volume of the red cells (anemia is classified as microcytic or macrocytic based on whether this value is above or below the expected normal range. Other conditions that can affect MCV include thalassemia, reticulocytosis and alcoholism); mean corpuscular hemoglobin (MCH)—the average amount of hemoglobin per red blood cell, in picograms; mean corpuscular hemoglobin concentration (MCHC)—the average concentration of hemoglobin in the cells; red blood cell distribution width (RDW)—the variation in cellular volume of the RBC population; total white blood cells; neutrophil granulocytes (may indicate bacterial infection, typically increased in acute viral infections). Due to the segmented appearance of the nucleus, neutrophils are sometimes referred to as "segs"" The nucleus of less mature neutrophils is not segmented, but has a band or elongated shape. Less mature neutrophils—those that have recently been released from the bone marrow into the bloodstream—are known as "bands". Other data/parameters for a blood count can also include, for example, lymphocytes (e.g., increased with some viral infections such as glandular fever, and in chronic lymphocytic leukemia (CLL), or decreased by HIV infection); monocytes (may be increased in bacterial infection, tuberculosis, malaria, Rocky Mountain spotted fever, monocytic leukemia, chronic ulcerative colitis and regional enteritis; eosinophil granulocytes (e.g., increased in parasitic infections, asthma, or allergic reaction); basophil granulocytes (e.g., increased in bone marrow related conditions such as leukemia or lymphoma.

As used herein, data/parameters of a blood count can also include, for example, data associated with platelets, including platelet numbers, information about their size and the range of sizes in the blood; mean platelet volume (MPV)—a measurement of the average size of platelets.

In another aspect of the methods of this invention, the cells contacted with particle contrast agent composition and/or imaged are abnormal cells, such as malaria-infected cells, atypical lymphocytes. In some aspects of this invention, the cells are abnormal cells which can be used to identify, predict, diagnose, prognose, or support a diagnosis of a condition, disease, infection and/or syndrome.

In another aspect of the methods of this invention, the cells are platelets.

Unless expressly indicated otherwise, references to "particle" or "particles" made in this disclosure will be understood to encompass any discrete or formed object dispersed in a fluid. As used herein, "particle" can include all measurable and detectable (e.g., by image and/or other measurable parameters) components in biological fluids. The particles are of any material, any shape and any size. In certain embodiments, particles can comprise cells. Examples of particles include but are not limited to cells, including blood cells, fetal cells, epithelials, stem cells, tumor cells, or bacteria, parasites, or fragments of any of the foregoing or other fragments in a biological fluid. Blood cells may be any blood cell, including any normal or abnormal, mature or immature cells which potentially exist in a biological fluid, for example, red blood cells (RBCs), white blood cells (WBCs), platelets (PLTs) and other cells. The members also include immature or abnormal cells. Immature WBCs may include metamyelocytes, myelocytes, pro-myelocytes and blasts. In addition to mature RBCs, members of RBCs may include nucleated RBCs (NRBCs) and reticulocytes. PLTs may include "giant" PLTs and PLT clumps. Blood cells and formed elements are further described elsewhere in this disclosure.

Exemplary particles can include formed elements in biological fluid samples, including for example, spherical and non-spherical particles. In certain embodiments, the particles can comprise non-spherical components. The image projection of non-spherical components can be maximized in the focal plane of the high optical resolution imaging device. In certain embodiments, the non-spherical particles are aligned in the focal plane of the high optical resolution imaging device (aligned in a plane substantially parallel to the direction of the flow). In some embodiments, platelets, reticulocytes, nucleated RBCs, and WBCs, including neutrophils, lymphocytes, monocytes, eosinophils, basophils, and immature WBCs including blasts, promyelocytes, myelocytes, or metamyelocytes are counted and analyzed as particles.

As used herein, detectable and measurable particle parameters can include, for example, visual and/or non-image based indices of size, shape, symmetry, contour and/or other characteristics.

The sample can be an isolated and/or prepared biological sample, including for example, a body fluid sample, a blood, serum, cerebrospinal fluid, pleural fluid, peritoneal fluid, saliva, seminal fluid, tears, sweat, milk, amniotic fluid, lavage fluid, bone marrow asirate, effusions, exudates, or other sample obtained from a subject (e.g., biopsy sample that has been treated to produce a cell suspension, or a laboratory or production line sample comprising particles). In some embodiments, the sample can be a solid tissue sample, e.g., a biopsy sample that has been treated to produce a cell suspension. The sample may also be a suspension obtained from treating a fecal sample. A sample may also be a laboratory, chemical, industrial or production line sample comprising particles, such as a cell culture sample. The term sample may be used to refer to a sample obtained from a patient or laboratory or any fraction, portion or aliquot thereof. The sample can be diluted, divided into portions, or treated with a contrast agent in some processes.

The methods disclosed herein are applicable to samples from a wide range of organisms, including mammals, e.g., humans, non-human primates (e.g., monkeys), horses, cows or other livestock, dogs, cats or other mammals kept as pets, rats, mice, or other laboratory animals; birds, e.g., chickens; reptiles, e.g., alligators; fish, e.g., salmon and other farmed species; and amphibians.

The samples can be obtained by any conventional method, e.g., excretion, draw, harvesting, aspirate, or a biopsy. The sample can be from a subject considered to be healthy, for example, a sample collected as part of a routine physical examination. The sample can also be from a subject who has, who is at risk for, or who is suspected of having a disorder. The disorder can be the result of a disease, a genetic abnormality, an infection, an injury or unknown causes. Alternatively or in addition, the methods can be useful for monitoring a subject during the course of treatment for a disorder. Where there are signs of non-responsiveness to treatment and/or therapy, a clinician can choose an alternative or adjunctive agent. Depending upon the condition of the subject and the particular disorder, if any, samples can be collected once (or twice, three times, etc.) daily, weekly, monthly, or yearly.

The particles can vary depending upon the sample. The particles can be biological cells, for example, blood cells, fetal cells, stem cells, tumor cells or fragments thereof. In some embodiments the particles can be an infectious agent, for example, a virus or bacterium.

Reference to "blood cells" made in this disclosure will be understood to encompass any normal or abnormal, mature or immature cells which potentially exist in a biological fluid, for example, red blood cells (RBCs), white blood cells (WBCs), platelets (PLTs) and other cells. In general, normal RBCs, PLTs, and WBCs have a particle diameter in the range of 6-8 µm, 2-3 µm, and 8-15 µm, respectively. Normal RBCs, PLTs and WBCs are present in whole blood samples from normal patients in an approximate concentration range of 3.9-5.7×1012 cells/L, 1.4-4.5×1011 cells/L, 3.5-11×109 cells/L, respectively. See, Barbara J. Bain, Blood Cells, A Practical Guide, 4th ed., Blackwell Publishing, 2007, 34-36.

Reference to a "formed element" will be understood to encompass non-fluid elements present in biological fluid samples. Formed elements include, for example, classes of blood cells based on scientific classification or physiological function including erythrocytes (RBCs), leukocytes (WBCs) and platelets (PLTs), WBC clumps, subclasses of leukocytes, which include mature lymphocytes, and immature leukocytes such as monocytes, neutrophils, eosinophils, basophils. "Formed elements" for use herein will also include particles such as microorganisms, bacteria, fungi, parasites, or fragments thereof or other cell fragments.

Major members of WBCs include but are not limited to neutrophils, lymphocytes, monocytes, eosinophils, and basophils. The members also include immature or abnormal cells. For example, immature WBCs may include metamyelocytes, myelocytes, pro-myelocytes. In addition to mature RBCs, members of RBCs may include nucleated RBCs (NRBCs) and reticulocytes. PLTs may include regular PLTs, and "giant" PLTs whose size is close to that of regular WBCs. Reference to a "member" or "members" of a category and/or subcategory of particles made in this disclosure will be understood to encompass individual particles within a category or sub-category of particles.

Unless expressly indicated otherwise, reference to a "category" of particles made in this disclosure will be understood to encompass a group of particles detected using at least one detection criterion measured, detected or derived such as size, shape, texture, or color. In some embodiments the members of at least one category and/or subcategory of particles counted by the apparatus of this disclosure will be the same type of formed element.

Such particles may be detected in a "channel." Reference to "channel" made in this disclosure will be understood to encompass a portion of the particle counter comprising a detector coupled to a signal source, providing an output that varies with greater or lesser detection of particles that meet at least one channel detection criterion. For example, a channel detection criterion can be based on size or volume of the particles. In some embodiments, the number of channels in a particle counter is one. In some other embodiments, the number of the channels in a particle counter is two or more.

One category and/or subcategory of particles detected in one channel of particle counter may comprise different classes and subclasses of particles, and grouped members of particles in two or more subclasses. Reference to a "category" of particles made in this disclosure will be understood to encompass a grouping of particles corresponding to criteria measured, detected or derived such as size, shape, texture, or color. In some embodiments the members of at least one category and/or subcategory of particles counted by the apparatus of this disclosure will be the same type of formed element.

As used herein, the term high optical resolution imaging device can include devices that are capable of obtaining particles images with sufficient visual distinctions to differentiate morphological features and/or changes. Exemplary high optical resolution imaging devices can include devices with an optical resolution of 1 um or lower, including for example, 0.4 to 0.5 um, such as for example, 0.46 um.

As used herein, the particle contrast agent compositions can be adapted for use in combination with a particle and/or intracellular organelle alignment liquid (PIOAL) in a visual analyzer for analyzing particles in a sample from a subject. The exemplary PIOAL is useful, as an example, in methods for automated recognition of different types of particles in a sample from a subject.

In another aspect, the cells may be enveloped in PIOAL when images are obtained. Suitable exemplary intracellular organelle alignment liquids are described herein.

As used herein, "alignment" can be characterized in part by the alignment of spherical and/or non-spherical particles. For example, particles such as non-spherical particles may be aligned in a plane substantially parallel to the direction of the flow. In certain embodiments, alignment of the non-spherical particles is characterized by the orientation of the particles increase an image projection of the non-spherical particles under imaging conditions in the focal plane of the high optical resolution imaging device. Particles such as spherical particles may have an increase in the amount of the in focus intraparticle contents of the particles and cells which is effective to generate visual distinctions for particle categorization and subcategorization. The intraparticle structures of particles such as spherical particles may be positioned, repositioned and/or better-positioned to be substantially parallel to the direction of flow. For example, intracellular structures, organelles or lobes may also be positioned, repositioned, and/or better-positioned to be substantially parallel to the direction of flow.

Reference to a "class" of particles made in this disclosure will be understood to encompass a group of particles based on scientific classification. For example, three major classes of blood cells exist in a whole blood sample, including RBCS, WBCs and PLTs.

Reference to a "member" or "members" of particles made in this disclosure will be understood to encompass particles in one category or subcategory of particles. For example, each category of blood cells can be further divided into subcategories or members. Major members of WBCs include but are not limited to neutrophils, lymphocytes, monocytes, eosinophils, and basophils. The members also include immature or abnormal cells. For example, immature WBCs may include metamyelocytes, myelocytes, and pro-myelocytes. In addition to mature RBCs, members of RBCs may include nucleated RBCS (NRBCs) and reticulocytes. PLTs may include regular PLTs, and "giant" PLTs whose size is close to that of regular WBCs.

Reference to "immature cells" will be understood to encompass cells in a certain developmental stage, for example, inside the bone marrow or shortly after release from bone marrow but before full development into a mature cell.

Reference to "abnormal cells" will be understood to encompass cells with irregular morphological characteristics or cells associated with a certain disease or condition, or irregularities associated which may in some instances be associated with certain diseases or conditions. Examples of certain disease include but are not limited to erythrocytosis, polycythemia, anemia, erythroblastopenia, leukocytosis, leukopenia, lymphocytosis, lymphocytopenia, granulocytosis, granulocytopenia or agranulocytosis, neutrophilia, neutropenia, eosinophilia, eosinopenia, basophilia, basopenia, thrombocytosis, thrombocytopenia, and pancytopenia. A class of cells may increase or decrease in the bloodstream. In some conditions, abnormal cells much larger than regular white cells exist at a small concentration in a blood sample. Variations in size, shape, color, and/or intracellular structures may be associated with certain diseases or conditions.

Reference to "count" of particles or "particle count" made in this disclosure will be understood to encompass the numbers of particles obtained from one channel of a particle counter. Reference to "concentration" of a class or a member of particles made in this disclosure will be understood to mean the numbers of the particles per unit volume (e.g., per liter) or per sample of a known volume. For example, a particle counter may provide counts or concentrations or other count based function for categories of particles, while a visual analyzer may provide counts, concentrations, ratios or other concentration based parameters for each category or subcategory of particles.

Reference to "ratio" made in this disclosure will be understood to encompass any quantitative and/or proportionate ratio of two categories/subcategories, classes or members of particles. Examples of such a ratio include but are not limited to a ratio by concentration, weight, and/or by numbers of particles. Typically the ratio concerns the numerical fraction of the count of one category, class or member over the count of another such category, class or member. In some embodiments, determinations using weighted counts or weighted and/or proportionate ratios may also be made.

Hematology—Particle Analysis System

Turning now to the drawings, FIG. 1 schematically shows an exemplary flowcell 22 for conveying a sample fluid through a viewing zone 23 of a high optical resolution imaging device 24 in a configuration for imaging microscopic particles in a sample flow stream 32 using digital image processing. Flowcell 22 is coupled to a source 25 of sample fluid which may have been subjected to processing, such as contact with a particle contrast agent composition and heating. Flowcell 22 is also coupled to one or more sources 27 of a particle and/or intracellular organelle alignment liquid (PIOAL), such as a clear glycerol solution having a viscosity that is greater than the viscosity of the sample fluid.

The sample fluid is injected through a flattened opening at a distal end 28 of a sample feed tube 29, and into the interior of the flowcell 22 at a point where the PIOAL flow has been substantially established resulting in a stable and symmetric laminar flow of the PIOAL above and below (or on opposing sides of) the ribbon-shaped sample stream. The sample and PIOAL streams may be supplied by precision metering pumps that move the PIOAL with the injected sample fluid along a flowpath that narrows substantially. The PIOAL envelopes and compresses the sample fluid in the zone 21 where the flowpath narrows. Hence, the decrease in flowpath thickness at zone 21 can contribute to a geometric focusing of the sample stream 32. The sample fluid ribbon 32 is enveloped and carried along with the PIOAL downstream of the narrowing zone 21, passing in front of, or otherwise through the viewing zone 23 of, the high optical resolution imaging device 24 where images are collected, for example, using a CCD 48. Processor 18 can receive, as input, pixel data from CCD 48. The sample fluid ribbon flows together with the PIOAF to a discharge 33.

As shown here, the narrowing zone 21 can have a proximal flowpath portion 21a having a proximal thickness PT and a distal flowpath portion 21b having a distal thickness DT, such that distal thickness DT is less than proximal thickness PT. The sample fluid can therefore be injected through the distal end 28 of sample tube 29 at a location that is distal to the proximal portion 21a and proximal to the distal portion 21b. Hence, the sample fluid can enter the PIOAL envelope as the PIOAL stream is compressed by the zone 21. wherein the sample fluid injection tube has a distal exit port through which sample fluid is injected into flowing sheath fluid, the distal exit port bounded by the decrease in flowpath size of the flowcell.

The digital high optical resolution imaging device 24 with objective lens 46 is directed along an optical axis that intersects the ribbon-shaped sample stream 32. The relative distance between the objective 46 and the flowcell 33 is variable by operation of a motor drive 54, for resolving and collecting a focused digitized image on a photosensor array.

Flowcell

Figure 2:
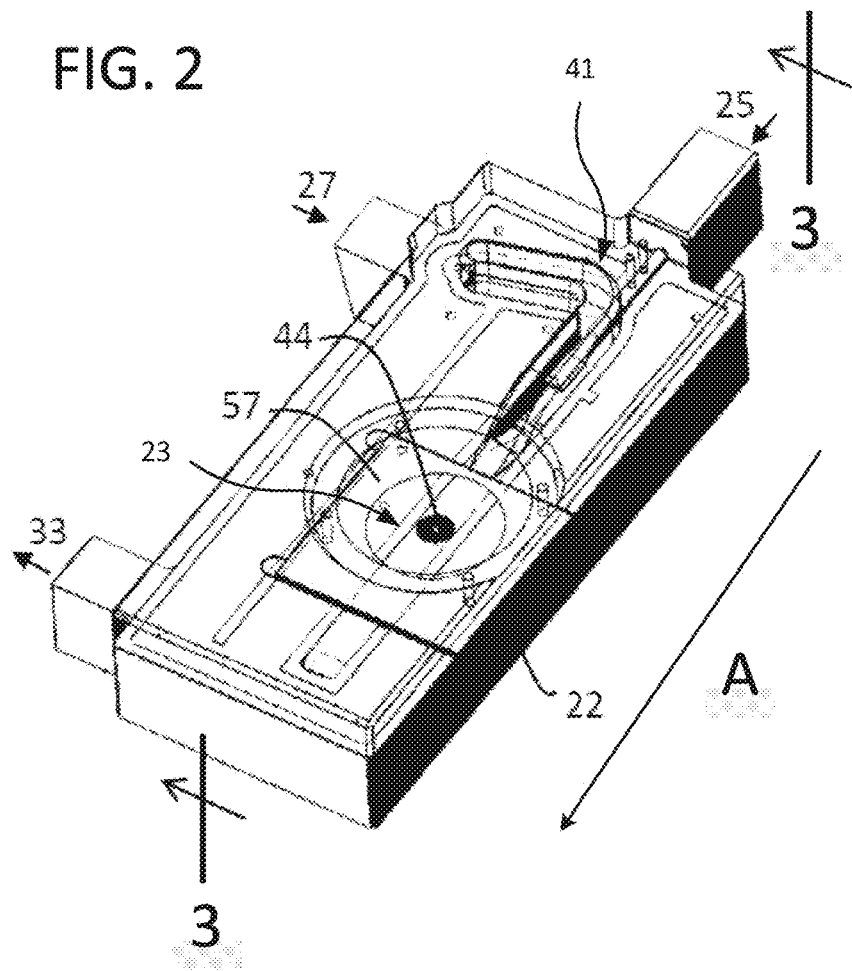
FIG. 2 is a perspective illustration of a flowcell according to an exemplary embodiment.
Figure 3:
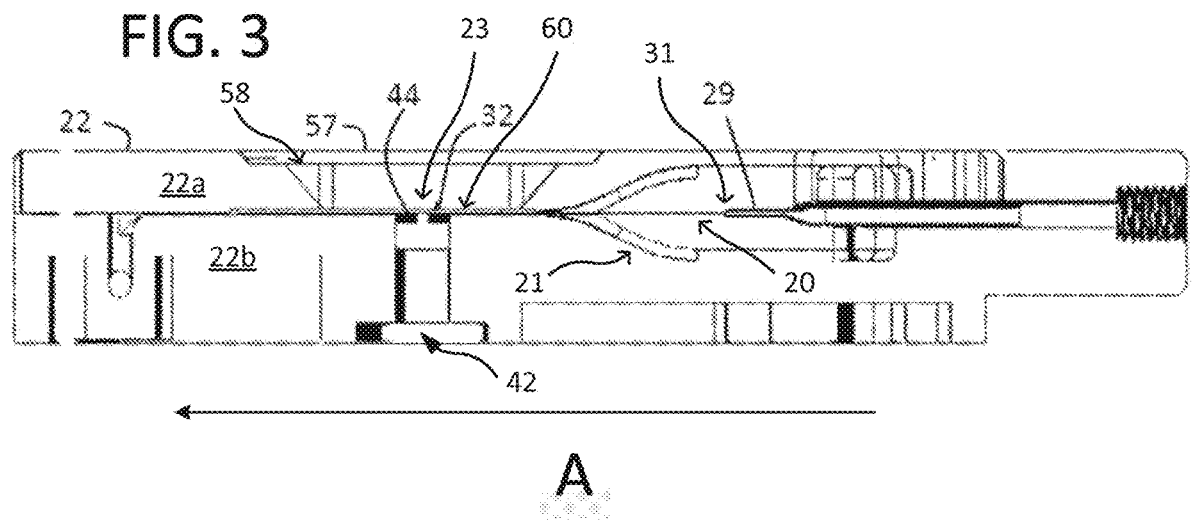
FIG. 3 is a longitudinal median section view along lines 3-3 of the flowcell shown in FIG. 2.

A practical embodiment of flowcell 22 is further depicted in FIGS. 2 and 3. As shown here, flowcell 22 can be coupled with a sample source 25 and also to a source 27 of PIOAL material. The sample fluid is injected into the flowcell 22 via the cannula 29, for example through a distal exit port 31 of the cannula 29. Typically, the PIOAL sheath fluid is not in a laminar flow state as it travels through a curved channel section 41 in the flowcell from the source 27 toward the viewing zone 23. However, the flowcell 22 can be configured so that the PIOAL sheath fluid is or becomes laminar, or presents a flat velocity profile, as it flows past the distal exit port 31 where sample fluid is introduced into the flowing sheath fluid. The sample fluid and the PIOAL can flow along the flowcell 22 in a direction generally indicated by arrow A, and then out of the flowcell 22 via discharge 33. The flowcell 22 defines an internal flowpath 20 that narrows symmetrically (e.g. at transition zone 21) in the flow direction A. The symmetry of the flowpath contributes to a robust and centered flow of the sample stream. The flowcell 22 is configured to direct a flow 32 of the sample enveloped with the PIOAL through a viewing zone 23 in the flowcell, namely behind viewing port 57. Associated with the viewport 57 is an auto focus pattern 44. Flowcell 22 also has a rounded or recessed seat 58 which is configured to accept or receive a microscope objective (not shown).

According to some embodiments, the auto focus pattern 44 can have a position that is fixed relative to the flowcell 22, and that is located at a displacement distance from the plane of the ribbon-shaped sample stream 32. In the embodiment shown here, the autofocus pattern (target 44) is applied directly to the flowcell 22 at a location that is visible in an image collected through viewport 57 by a high optical resolution imaging device (not shown). Flowcell 22 can be constructed of a first or upper section or layer 22a and a second or lower section or layer 22b. As shown here, a glass or transparent window pane 60 is attached to or integral with the first section 22a. The pane 60 can define at least a portion of the sample flowpath within the flowcell. Light from light source 42 can travel through an aperture or passage of the autofocus pattern 44 so as to illuminate sample particles flowing within the flow stream 32.

In some cases, the thickness of pane 60 can have a value within a range from about 150 pm to about 170 pm. As noted above, the pane 60 can define or form part of the flowpath or sheath (e.g. PIAOL) channel. By using a thin pane 60, it is possible to place the microscope objective very close to the sample fluid ribbon, and hence obtain highly magnified images of particles flowing along the flowpath.

Figure 3A:
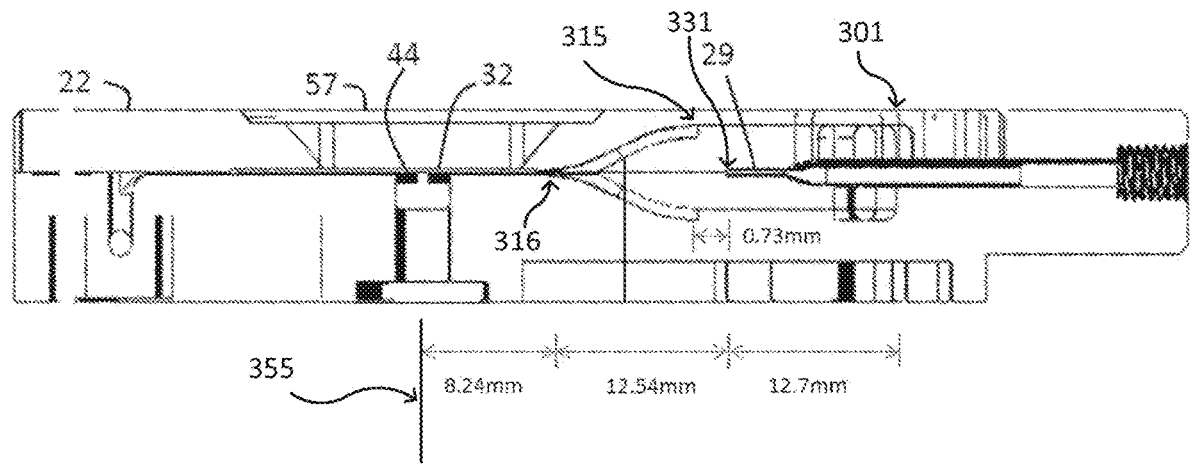
FIGS. 3A and 3B provide additional section views of flowcells according to embodiments of the present invention.
Figure 3B:
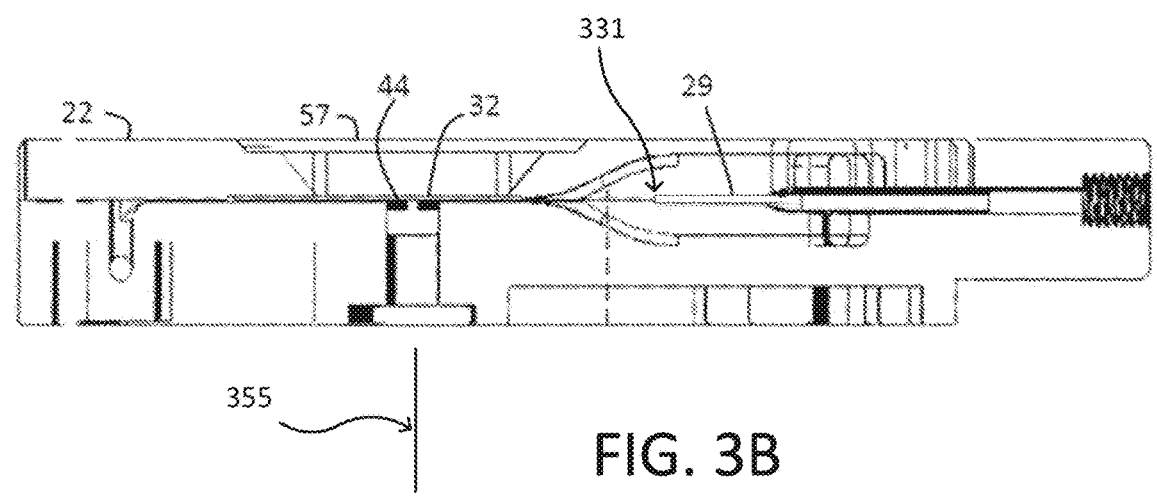

FIG. 3A depicts aspects of a flowcell embodiment, where a distance between the imaging axis 355 and the distal transition zone portion 316 is about 8.24 mm. A distance between the distal transition zone portion 316 and the cannula exit port 331 is about 12.54 mm. A distance between the cannula exit port 331 and the sheath fluid entrance 301 is about 12.7 mm. A distance between the cannula exit port 331 and a proximal transition zone portion 318 is about 0.73 mm. FIG. 3B depicts aspects of a flowcell embodiment where the cannula exit port has been moved to a more distal location relative transition zone, as compared to the FIG. 3A embodiment. As shown here, the cannula distal end is advanced into the narrowing transition zone of the flowcell, and a distance between the imaging axis 355 and the distal transition zone portion 316 is within a range from about 16 mm to about 26 mm. In some case, the distance between the imaging axis 355 and the distal transition zone portion 316 is about 21 mm.

With returning reference to FIG. 1, the flowcell internal contour (e.g. at transition zone 21) and the PIOAL and sample flow rates can be adjusted such that the sample is formed into a ribbon shaped stream 32. The stream can be approximately as thin as or even thinner than the particles that are enveloped in the ribbon-shaped sample stream. White blood cells may have a diameter around 10 μm, for example. By providing a ribbon-shaped sample stream with a thickness less than 10 μm, the cells may be oriented when the ribbon-shaped sample stream is stretched by the sheath fluid, or PIOAL. Surprisingly stretching of the ribbon-shaped sample stream along a narrowing flowpath within PIOAL layers of different viscosity than the ribbon-shaped sample stream, such as higher viscosity, advantageously tends to align non-spherical particles in a plane substantially parallel to the flow direction, and apply forces on the cells, improving the in-focus contents of intracellular structures of cells. The optical axis of the high optical resolution imaging device 24 is substantially normal (perpendicular) to the plane of the ribbon-shaped sample stream. The linear velocity of the ribbon-shaped sample stream at the point of imaging may be, for example, 20-200 mm/second. In some embodiments, the linear velocity of the ribbon-shaped sample stream may be, for example, 50-150 mm/second.

The ribbon-shaped sample stream thickness can be affected by the relative viscosities and flow rates of the sample fluid and the PIOAL. The source 25 of the sample and/or the source 27 of the PIOAL, for example comprising precision displacement pumps, can be configured to provide the sample and/or the PIOAL at controllable flow rates for optimizing the dimensions of the ribbon-shaped sample stream 32, namely as a thin ribbon at least as wide as the field of view of the high optical resolution imaging device 24.

In one embodiment, the source 27 of the PIOAL is configured to provide the PIOAL at a predetermined viscosity. That viscosity may be different than the viscosity of the sample, and can be higher than the viscosity of the sample. The viscosity and density of the PIOAL, the viscosity of the sample material, the flow rate of the PIOAL and the flow rate of the sample material are coordinated to maintain the ribbon-shaped sample stream at the displacement distance from the autofocus pattern, and with predetermined dimensional characteristics, such as an advantageous ribbon-shaped sample stream thickness.

In a practical embodiment, the PIOAL has a higher linear velocity than the sample and a higher viscosity than the sample, thereby stretching the sample into the flat ribbon. The PIOAL viscosity can be up to 10 centipoise.

Referring also to FIGS. 2 and 3, the internal flowpath of the flowcell narrows downstream of the point of injection of the ribbon-shaped sample stream into the PIOAL, to produce a ribbon-shaped sample stream thickness, for example, up to 7 μm, and/or the internal flowpath produces a ribbon-shaped sample stream width of 500-3,000 μm. In exemplary embodiments, as depicted in FIG. 1, the internal flowpath of the flowcell begins a narrowing transition zone upstream of the point of injection of the sample stream into the PIOAL.

In another embodiment the internal flowpath narrows to produce a ribbon-shaped sample stream thickness of 2-4 μm in thickness, and/or the internal flowpath results in the ribbon-shaped sample stream of 2000 μm in width. These dimensions are particularly useful for hematology. The thickness of the stream in this case is less than the diameter of some particles, such as red blood cells in their relaxed state. Accordingly, those particles can become reoriented to face their wider a dimension to the imaging axis, which is helpful in revealing distinguishing characteristics.

The linear velocity of the ribbon-shaped sample stream can be limited sufficiently to prevent motion blurring of the digitized image at the image exposure time of the photosensor array. The light source can optionally be a strobe light that is flashed to apply high incident amplitude for a brief time. In as much as the autofocus pattern 44 and the image are in the same field of view, the light source is configured to illuminate the ribbon-shaped sample stream and the autofocus pattern simultaneously. However in other embodiments, the field of view for imaging and for auto focus can be different, e.g., illuminated and/or imaged separately.

The subject developments have method as well as apparatus aspects. A method of focusing a visual analyzer comprises focusing a high optical resolution imaging device 24, which may be a digital high optical resolution imaging device or the digital image capture device, on an autofocus pattern 44 fixed relative to a flowcell 22, wherein the autofocus pattern 44 is located at a displacement distance 52 from a ribbon-shaped sample stream 32. The digital high optical resolution imaging device 24 has an objective with an optical axis that intersects the ribbon-shaped sample stream 32. A relative distance between the objective and the flowcell 22 is varied by operation of a motor drive 54, whereas the distance along the optical axis between the high optical resolution imaging device and the point of optimal focus is known. The digital high optical resolution imaging device is configured to resolve and collect a digitized image on a photosensor array. The motor drive is operated to focus on the autofocus pattern in an autofocus process. The motor drive then is operated over the displacement distance, thereby focusing the high optical resolution imaging device on the ribbon-shaped sample stream.

The method further can further include forming the ribbon-shaped sample stream into a ribbon-shape. The ribbon shape is presented such that the optical axis of the high optical resolution imaging device is substantially perpendicular to the ribbon-shaped sample stream, namely normal to the plane of the ribbon-shaped stream.

Figure 4:
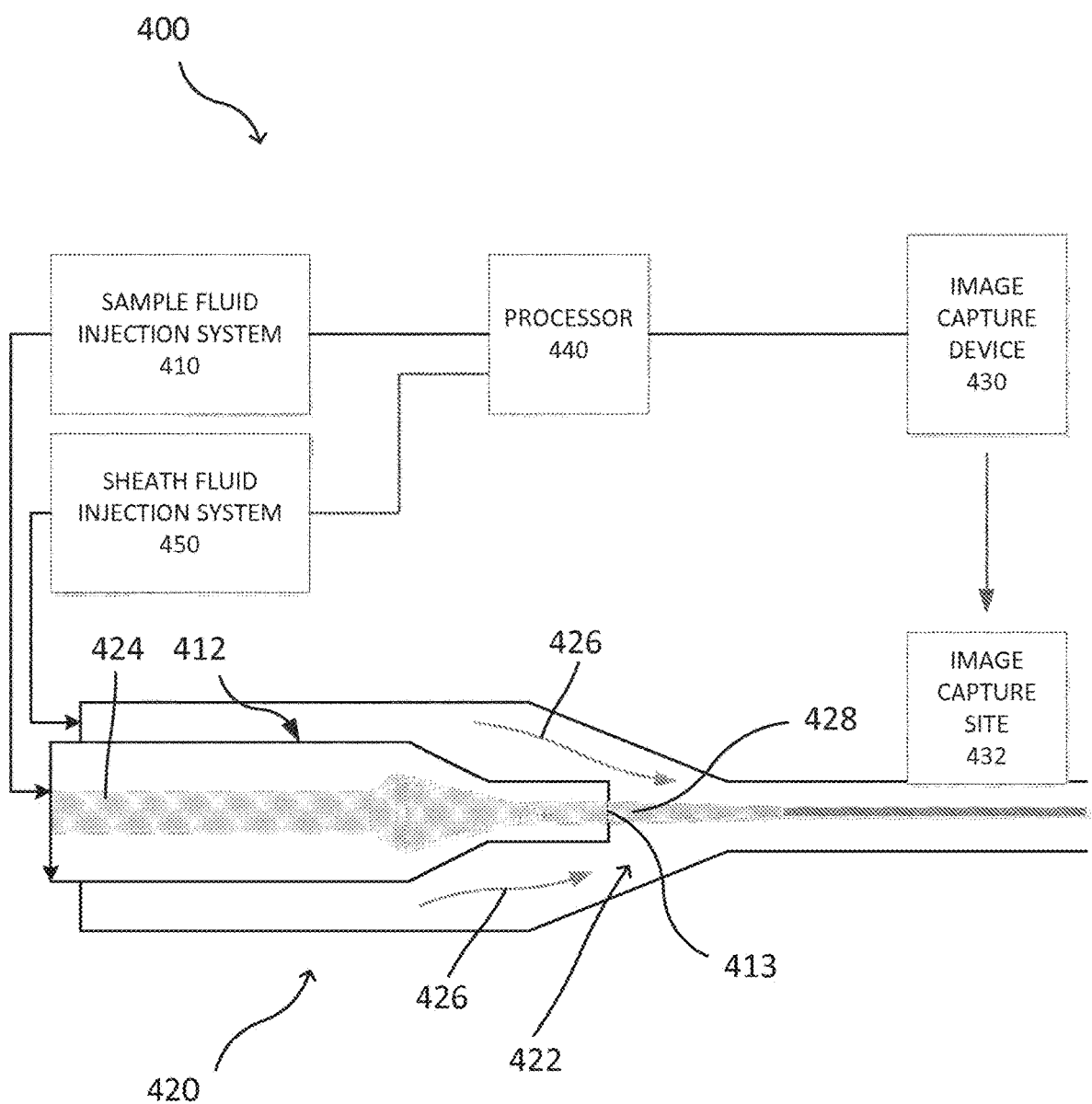
FIG. 4 illustrates aspects of an imaging system according to embodiments of the present invention.

FIG. 4 depicts aspects of a system 400 for imaging particles in a blood fluid sample. As shown here, system 400 includes a sample fluid injection system 410, a flowcell 420, and image capture device 430, and a processor 440. The flowcell 420 provides a flowpath 422 that transmits a flow of the sheath fluid, optionally in combination with the sample fluid. According to some embodiments, the sample fluid injection system 410 can include or be coupled with a cannula or tube 412. The sample fluid injection system 410 can be in fluid communication with the flowpath 422, and can operate to inject sample fluid 424 through a distal exit port 413 of the cannula 412 and into a flowing sheath fluid 426 within the flowcell 420 so as to provide a sample fluid stream 428. For example, the processor 440 may include or be in operative association with a storage medium having a computer application that, when executed by the processor, is configured to cause the sample fluid injection system 410 to inject sample fluid 424 into the flowing sheath fluid 426. As shown here, sheath fluid 426 can be introduced into the flowcell 420 by a sheath fluid injection system 450. For example, the processor 440 may include or be in operative association with a storage medium having a computer application that, when executed by the processor, is configured to cause the sheath fluid injection system 450 to inject sheath fluid 426 into the flowcell 420.

The sample fluid stream 428 has a first thickness T1 adjacent the injection tube 412. The flowpath 422 of the flowcell having a decrease in flowpath size such that the thickness of the sample fluid stream 428 decreases from the initial thickness T1 to a second thickness T2 adjacent an image capture site 432. The image capture device 430 is aligned with the image capture site 432 so as to image a first plurality of the particles from the first sample fluid at the image capture site 432 of the flowcell 420.

The processor 440 is coupled with the sample fluid injector system 410, the image capture device 430, and optionally the sheath fluid injection system 450. The processor 440 is configured to terminate injection of the first sample fluid into the flowing sheath fluid 426 and begin injection of the second sample fluid into the flowing sheath fluid 426 such that sample fluid transients are initiated. For example, the processor 440 may include or be in operative association with a storage medium having a computer application that, when executed by the processor, is configured to cause the sample fluid injection system 410 to inject the second sample fluid into the flowing sheath fluid 426 such that sample fluid transients are initiated.

Further, the processor 440 is configured to initiate capture of an image a second plurality of the particles from the second sample fluid at the image capture site 432 of the flowcell 420 after the sample fluid transients and within 4 seconds of the imaging of the first plurality the particles. For example, the processor 440 may include or be in operative association with a storage medium having a computer application that, when executed by the processor, is configured to cause the image capture device 430 to initiate capture of an image a second plurality of the particles from the second sample fluid at the image capture site 432 of the flowcell 420 after the sample fluid transients and within four seconds of the imaging of the first plurality the particles.

Figure 4A:
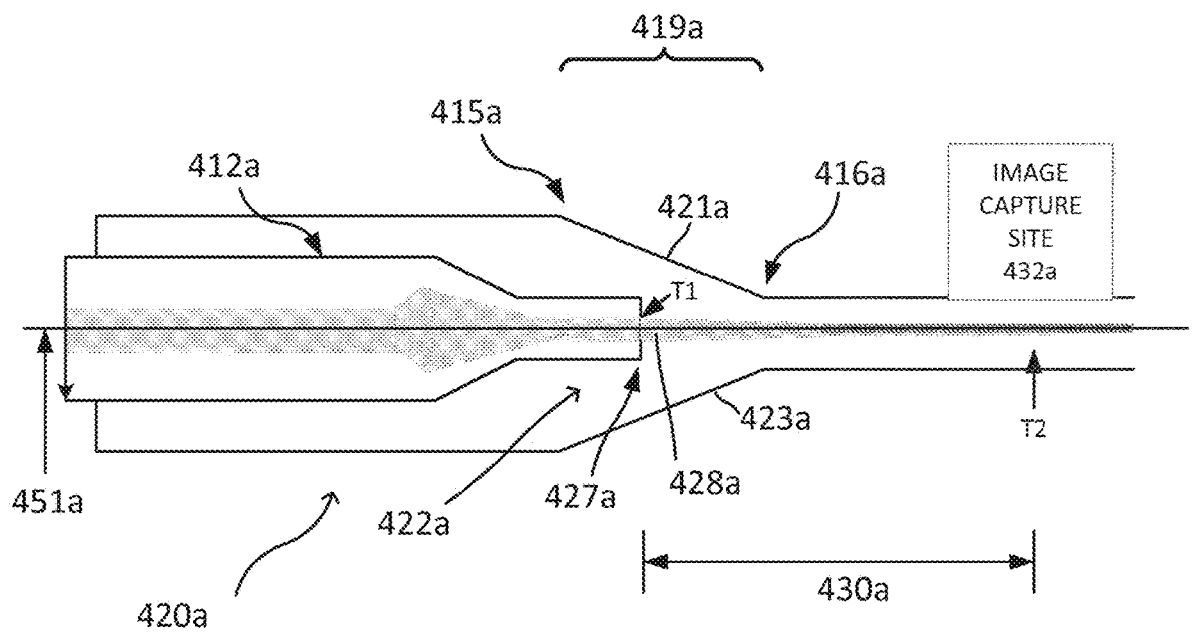
FIGS. 4A and 4B depict aspects of flowcells according to embodiments of the present invention.

As shown in the flowcell embodiment depicted in FIG. 4A, a decrease in flowpath size (e.g. at transition zone 419*a*) can be defined by opposed walls 421*a*, 423*a* of the flowpath 422*a*. The opposed walls 421*a*, 423*a* can angle radially inward along the flowpath 422*a*, generally symmetric about a transverse plane 451*a* that bisects the sample fluid stream 428*a*. The plane 451*a* can bisect the sample stream 428*a* where the sample stream has a first thickness T1, at a location where the sample stream 428*a* exits a distal portion 427*a* of the cannula or sample injection tube 412*a*. Similarly, the plane 451*a* can bisect the sample stream 428*a* where the sample stream has a second thickness T2, at a location where the sample stream 428*a* passes the image capture site 432*a*. According to some embodiments, the first thickness T1 has a value of about 150 μm and the second thickness T2 has a value of about 2 μm. In such cases, the compression ratio of the sample ribbon stream is 75:1. According to some embodiments, the first thickness T1 has a value within a range from about 50 μm to about 250 μm and the second thickness T2 has a value within a range from about 2 μm to about 10 μm. As the sample stream fluid flows through the flowcell, the ribbon thins out as it accelerates and is stretched. Two features of the flowcell can contribute to thinning of the sample fluid ribbon. First, a velocity difference between the sheath fluid envelope and the sample fluid ribbon can operate to reduce the thickness of the ribbon. Second, the tapered geometry of the transition zone can operate to reduce the thickness of the ribbon.

Typically, the first thickness T1 is much larger than the size of the sample particles, and hence the particles are contained entirely within the sample ribbon stream. However, the second thickness T2 may be smaller than the size of certain sample particles, and hence those particles may extend out of the sample fluid and into surrounding sheath fluid. As shown in FIG. 4A, the sample ribbon stream can flow generally along the same plane as it exits the cannula and travels toward the image capture site.

The flowcell can also provide a separation distance 430*a* between the distal cannula portion 427*a* and the image capture site 432*a*. According to some embodiments, the distal portion 427*a* of the sample fluid injection tube 412*a* can be positioned at an axial separation distance 430*a* from the image capture site 432*a*, where the axial separation distance 432*a* has a value of about 21 mm. In some cases, the axial separation distance 430*a* has a value within a range from about 16 mm to about 26 mm.

The axial separation distance 430*a* between the cannula exit port and image capture site can impact the transition time for the sample fluid as the fluid travels from the exit port to the image capture site. For instance, a relatively shorter axial separation distance 430*a* can contribute to a shorter transition time, and a relatively longer axial separation distance 430*a* can contribute to a longer transition time.

The position of the exit port at the cannula distal portion 427*a* relative to the flowpath transition zone 419*a*, or relative to the proximal portion 415*a* of the flowpath transition zone 419*a*, can also inference the transition time for the sample fluid as the fluid travels from the exit port to the image capture site. For example, the sheath fluid may have a relatively slower speed at the proximal portion 415*a*, and a relatively faster speed at a location between the proximal portion 415*a* and the distal portion 416*a*. Hence, if the cannula exit port at distal portion 427*a* is positioned at the proximal portion 415*a*, it will take a longer amount of time for the sample fluid to reach the image capture site, not only because the travel distance is longer, but also because the initial speed of the sample fluid after it exits the cannula distal port is slower (due to the slower sheath fluid speed). Put another way, the longer the sample fluid is present in the thicker portion (e.g. near proximal portion 415*a*) of the flowcell, the longer it takes the sample to reach the image capture site. Conversely, if the cannula exit port at distal portion 427*a* is positioned distal to the proximal portion 415*a* (e.g. at a central location between proximal portion 415*a* and distal portion 416*a*, as depicted in FIG. 4A), it will take a shorter amount of time for the sample fluid to reach the image capture site, not only because the travel distance is shorter, but also because the initial speed of the sample fluid after it exits the cannula distal port is faster (due to the faster sheath fluid speed). As discussed elsewhere herein, the sheath fluid is accelerated as it flows through the transition zone 419*a*, due to the narrowing cross-sectional area of the zone 419*a*.

According to some embodiments, with a shorter transition time, more time is available for image collection at the image capture site. For example, as the duration of the transition time from the cannula distal tip to the imaging area decreases, it is possible to process more samples in a specific amount of time, and relatedly it is possible to obtain more images in a specific amount of time (e.g. images per minute).

Although there are advantages associated with positioning the exit port of the cannula distal portion 427*a* more closely to the image capture site 432*a*, it is also desirable to maintain a certain distance between the port and the capture site. For example, as depicted in FIG. 3, an optical objective or front lens of an imaging device can be positioned in the seat 58 of the flowcell 22. If the exit port 31 of the cannula is too close to the seat 58, then the sample fluid may not be sufficient stabilized after it is injected into the sheath fluid so as to provide desired imaging properties at the image capture site. Similarly, it may be desirable to maintain the tapered transition region 21 at a distance from the viewing zone 23, so that the tapered region does not interfere with the positioning of the seat 58 which receives the image capture device objective.

With continuing reference to FIG. 4A, the downstream end 427a of the sample fluid injection tube 412a can be positioned distal to a proximal portion 415a of the flowpath transition zone 419a. Relatedly, the downstream end 427a of the sample fluid injection tube 412a can be positioned proximal to a distal portion 416a of the flowpath transition zone 419a. Hence, according to some embodiments, the sample fluid can be injected from the injection cannula 412a and into the flowcell at a location within the transition zone 419a.

According to some embodiments, symmetry in the decrease in flowpath size (e.g. at flowpath transition zone 419a) operates to limit particle misalignment in the blood fluid sample. For example, such symmetry can be effective to limit red blood cells imaging orientation misalignment in the blood fluid sample to less than about 20%.

According to some embodiments, methods disclosed herein are operable to the flagging rate during blood count analysis to below 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6% or 5% of samples.

According to some embodiments, the image capture site 432a has a field of view 433a of between about 150 μm×150 μm and 400 μm×400 μm. In some cases, the image capture site 432a has a field of view 433a of about 275 μm×275 μm. In some cases, the field of view can be defined in terms of length times width. If expressed as surface area, a 275 μm×275 μm field of view has an area of 75,625 μm$^2$. According to some embodiments, the field of view can be determined by the imaging device objective and its magnification. In some cases, the field of view can correspond to the extent of the field (area) that is imaged by the collection optics (e.g. objective, tube lens, and camera). In some cases, the field of view is much smaller than the viewing port of transparent area at the image capture site.

FIGS. 4A-1 and 4A-2 illustrate the effects of hydro focusing on the sample stream as it travels from the cannula exit port to the image capture site. As shown in FIG. 4A-1, the sample stream can have a height H(S) of about 150 μm and a width W(S) of about 1350 μm. Further, the PIOAL sheath stream can have a height H(P) of about 6000 μm and a width W(P) of about 4000 μm. Subsequent to the hydro-focusing, as shown in FIG. 4A-2, the sample stream can have a height H(S) of 2 μm and a width W(S) of about 1350 μm. Further, the PIOAL sheath stream can have a height H(P) of about 150 μm and a width W(P) of about 4000 μm. In one embodiment, the cross sectional area of the PIOAL sheath stream at the cannula exit is 40 times larger than the cross sectional area near the image capture site.

According to some embodiments, it can be useful to determine the cross-section of the flowcell channel at the image capture site. This can correspond to the PIOAL sheath stream height H(P) of about 150 μm and a width W(P) of about 4000 μm as depicted in FIG. 4A-2. It can also be useful to determine the volumetric flow rate of the combined sample and sheath fluid streaming through the flowcell at the image capture site. When the cross-section area and the flow rate are known, it is possible to determine the velocity of the combined sample and sheath fluid at the image capture site.

According to some embodiments, the flow of the sample and sheath fluids through the flowcell can be approximated with a parallel plate profile model. Relatedly, the flow rate in the center of the sample fluid stream (e.g. as depicted in FIG. 4A-2), can be about 1.5 times the average flow rate of the combined sample and sheath fluid stream.

According to some embodiments, the cross-sectional area of the sample flow at the cannula exit (e.g. W(S)×H(S) in FIG. 4A-1) is 40 times larger than the cross-sectional area of the sample flow at the imaging site (e.g. W(S)×H(S) in FIG. 4A-2). The volumetric flow rate of sheath fluid at the imaging area can be about 45 μL/second. The volumetric flow rate of sample fluid at the imaging area can be about 0.232 μL/second. In some cases, the cross-sectional area of the combined sheath and sample streams at the imaging site is 600,000 μm$^2$. In some cases, the average flowstream velocity at the imaging site is 75 mm/second.

The flow rate or velocity can be determined as the rate that results in clear and focused cellular images. Exemplary flow rates and velocities were discovered based on flow rates of the two samples that were observed to achieve certain sample flowstream ribbon shapes or characteristics at the imaging site. For example, at flow rate of about 75 mm/sec (or within a range from 20-200 mm/sec), the cells do not flow too slow such that there are overlaps of cells in consecutive images, and the cells do not flow too fast such that ghosting effects are created (blurred image). Relatedly, by avoiding excessively high flow rates, it is possible to conserve more reagent and sample. According to some embodiments, an optimal or desired linear velocity can be achieved by either changing the volumetric flow (pump rate) or the shape of cannula.

The flow velocity of the sample stream through the image capture zone can also be related to the performance of the image capture device relative to the flowcell function. For example, if the sample stream if flowing too quickly, it may be difficult to obtain clear images of particles contained in the sample (e.g. the shutter speed of the image capture device may be too low, thus producing a blurred image). Similarly, if the sample stream is flowing too slowly, the image capture device may obtain consecutive images of the same particle (e.g. the same particle remains in the capture frame during two image captures). In some embodiments, the velocity of the sample ribbon can be modulated (e.g. by adjusting any of a variety of the flowcell operational parameters) relative to the image capture rate, so that there is minimal flow between frame captures, and hence a high percentage of the sample is imaged.

According to some embodiments, the particle analysis system and associated components can be configured so that as the sheath fluid and fluid sample flow through the flowcell, the sheath fluid can flow at a sheath fluid volumetric rate of 45 μL/s and the fluid sample can flow at a fluid sample volumetric flow rate of 0.232 μL/s (or within a range from 0.2 to 0.35 μL/s). In some cases, the ratio of the sheath fluid flow rate to the sample fluid flow rate is about 200. In some cases, the ratio of the sheath fluid flow rate to the sample fluid flow rate has a value within a range from about 70 to 200. In some cases, the ratio of the sheath fluid flow rate to the sample fluid flow rate is about 193. In some cases, the ratio of the sheath fluid flow rate to the sample fluid flow rate is about 70. In some instances, a ratio of sheath fluid volume to fluid sample volume flowing within the flowcell can be within a range from 25:1 to 250:1.

According to some embodiments, the system and associated components can be configured so that as sheath fluid and fluid sample flow through the flowcell 420, the sheath fluid can flow at a sheath fluid velocity of 75 mm/sec before the imaging area and the fluid sample can flow at a fluid sample velocity of 130 mm/sec before the imaging area. In some instances, a ratio of sheath fluid volume to fluid sample volume flowing within the flowcell can be within a range from 100:1 to 200:1.

In some instances, a flowcell can have a minimum compression ratio of about 50:1 and a maximum compression ratio of about 125:1. In some cases, the minimum compression ratio can be about 30:1 or 20:1. This compression ratio refers to the ratio of flow stream thicknesses H(S):H(S) when comparing FIG. 4A-1 to FIG. 4A-2. This compression ratio can be influenced by a combination of geometric compression (e.g. the ratio of the sheath fluid thicknesses H(P):H(P) when comparing FIG. 4A-1 to FIG. 4A-2, which can also correspond generally to the dimensions of the flowcell narrowing tapered transition zone 419a shown in FIG. 4A) and a hydrodynamic compression (e.g. also corresponding to a difference in velocity). According to some embodiments, the geometric compression ratio is about 40:1.

Figure 4B:
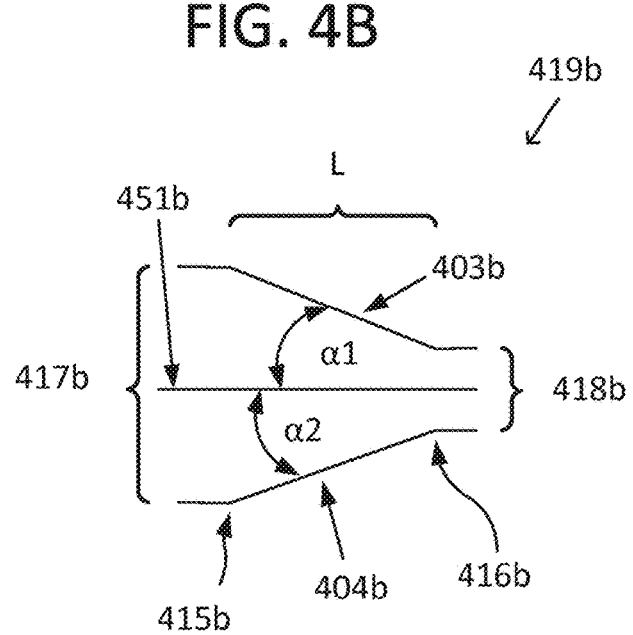
Figures 1, 4A:
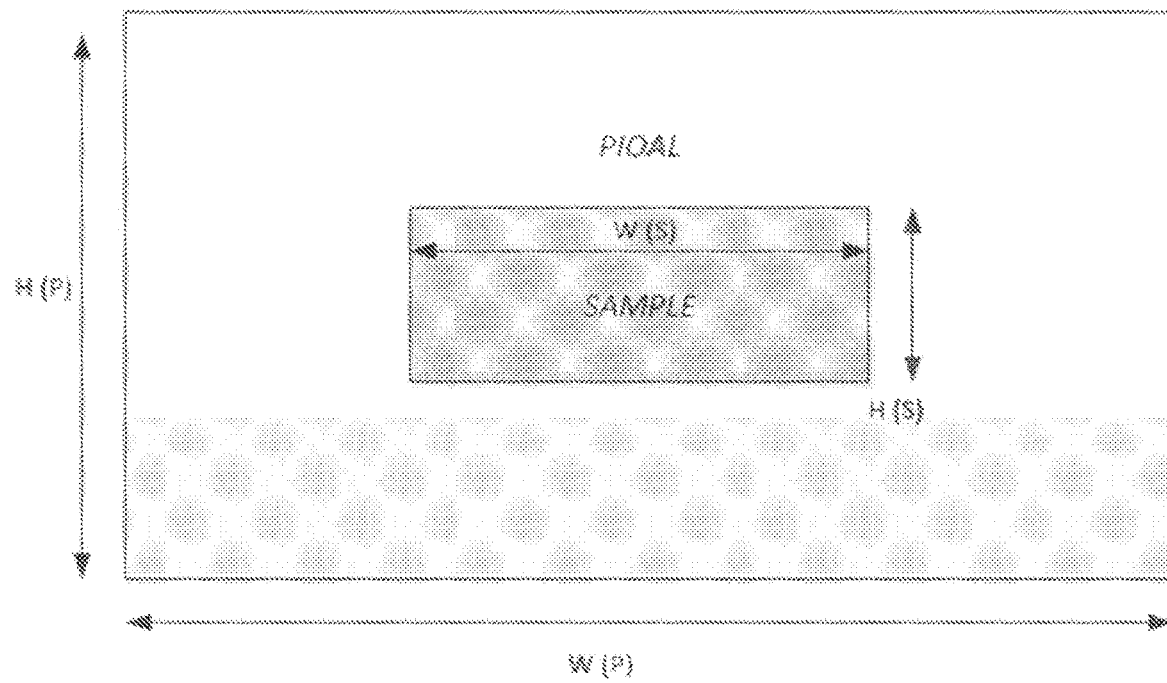
Figures 2, 4A:
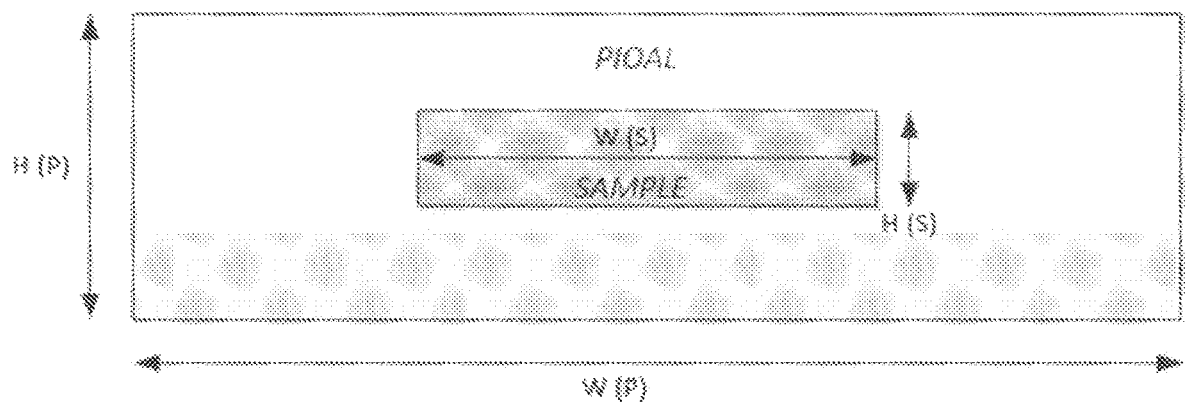

The decrease in flowpath size, corresponding to the transition zone, can be defined by a proximal flowpath portion having a proximal thickness or height, and a distal flowpath portion having a distal thickness or height that is less than the proximal thickness or height. For example, as shown in the partial view of FIG. 4B, the transition zone 419b of the flowpath can have a length L between a proximal portion 415b and a distal portion 416b, where the proximal portion 415b has a proximal height 417b, and the distal portion 416b has a distal height 418b. As noted elsewhere herein, the shape or contour of the transition zone can be curved or smooth, and for example can be provided in the shape of an S-curve or a tangent curve. According to some embodiments, the proximal height 417b has a value of about 6000 μm. In some cases, the proximal height 417b has a value within a range from about 3000 μm to about 8000 μm. According to some embodiments, the distal height 418b has a value of about 150 μm. In some cases, the distal height 418b has a value within a range from about 50 μm to about 400 μm.

The geometry of the transition zone 419a can provide a first angle α1 between the first flowpath boundary 403b and the bisecting transverse plane 451b, and a second angle α2 between the second flowpath boundary 404b and the bisecting transverse plane 451b. In some cases, angle α1 is about 45 degrees and angle α2 is about 45 degrees. In some cases, angle α1 has a value within a range from about 10 degrees to about 60 degrees. In some cases, angle α2 has a value within a range from about 10 degrees to about 60 degrees. According to some embodiments, angles α1 and α2 have the same value. The angles α1 and α2 can be selected so as to maintain laminar flow or minimize turbulence of the sample fluid as it travels from proximal portion 415b to distal portion 416b, which in turn can enhance alignment of particles within the sample along the transverse plane 451b. As noted above with reference to FIG. 4A, the distal and proximal boundaries or portions of the transition zone may be curved or smooth, instead of angled.

Figure 4K:
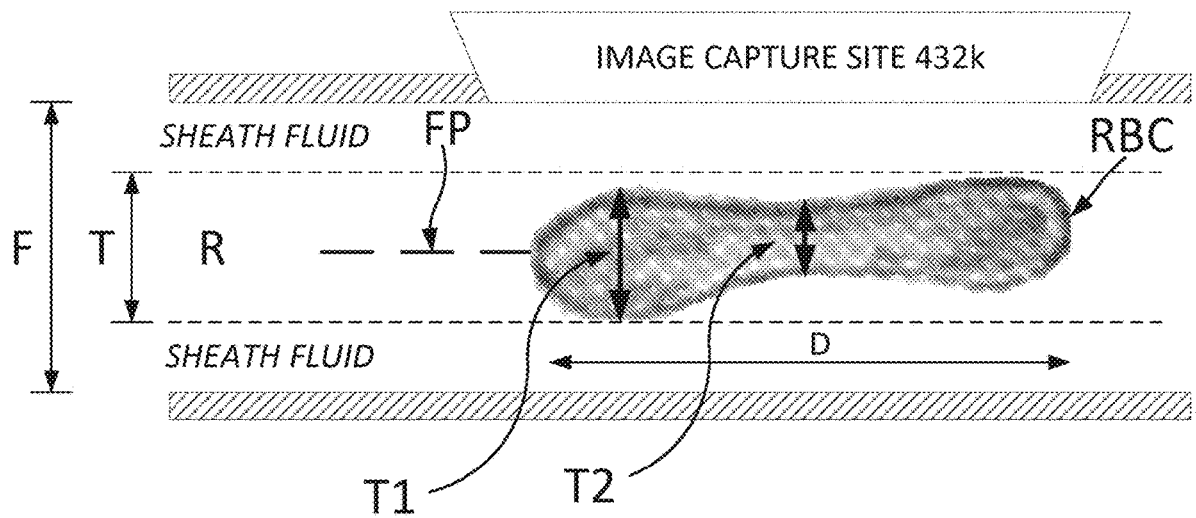
FIGS. 4K and 4L show a sample stream flowing through an image capture site of a flowcell according to embodiments of the present invention.

As shown in FIG. 4K, a sample stream ribbon R flowing through an image capture site 432k of a flowcell 420k can have a thickness T of about 2 μm. In some cases, thickness T of the sample stream ribbon can be up to about 3 μm. Typically, cells or particles that are smaller than the sample stream thickness will be contained within the ribbon. An exemplary red blood cell (RBC) can be present as a biconcave disk and can have a diameter D of between about 6.2 μm and about 8.2 μm. Further, an exemplary red blood cell can have a maximum thickness T1 of between about 2 μm and about 2.5 μm and a minimum thickness T2 of between about 0.8 μm and about 1 μm. In some cases, red blood cells can have a thickness of up to about 3 μm. Exemplary human platelets can vary in size, and can also have a thickness or diameter of about 2 μm. Although not shown to scale here, the flowcell can define a flow path thickness H having a value of about 150 μm, at the image capture site. In some cases, the flowpath thickness F has a value between 50 μm and 400 μm. This flowpath thickness F can also correspond to the distal height 418b of distal portion 461b depicted in FIG. 4B.

As shown in FIG. 4K, the ratio of the thickness T of the sample fluid stream to the thickness of the particle (red blood cell) is about 1:1. According so some embodiments, a ratio of the thickness T of the sample fluid stream at the image capture site to a size of one of the particles is within a range from 0.25 to 25. In some cases, the thickness T can have a value within a range from 0.5 μm to 5 μm. A viscosity differential between the sheath fluid and the sample fluid can be selected so as to achieve a desired positioning of the ribbon sample stream within the flowcell.

As discussed elsewhere herein, as well as in co-pending U.S. patent application Ser. No. 14/215,834 filed Mar. 17, 2014, viscosity differences between fluid of the sample ribbon R and the sheath fluid can operate to align or orient particles in the sample stream, for example red blood cells, along the direction of the flow. When so aligned, as shown in FIG. 4K, the imaging device or camera can obtain images of the red blood cells such they appear round, because the major surface of the blood cell is facing toward the camera. In this way, the red blood cell assumes an alignment that presents a low resistance relative to the flow. Hence, the relative viscosity characteristics of the sheath fluid and the sample fluid can contribute to a high percentage or number of red blood cells facing toward the camera, thus enhancing the evaluation capability of the particle analysis system.

According to some embodiments, the viscosity characteristics of the sheath fluid operate to limit particle misalignment in the blood fluid sample. For example, viscosity differentials can be effective to limit red blood cells imaging orientation misalignment in the blood fluid sample to less than about 10%. That is, 90 or more red blood cells out of 100 red blood cells in a sample can be aligned so that their major surfaces face toward the imaging device. A symmetrical narrowing transition zone can provide a value of 20%. According to some embodiments, the sheath fluid has an index of refraction similar to that of water (i.e. n=1.3330). In some cases, the sheath fluid has a water content of about 89%. In addition to alignment effects observed as a result of the viscosity differential, alignment effects are also observed as a result of a bilateral tapered transition zone. In some cases, it is observed that a bilateral (i.e. symmetrical) tapered transition zone is twice as effective at aligning particles as compared to an asymmetric tapered transition zone design.

Efficient alignment of the red blood cells can contribute to improved diagnosis. In some cases, the shape of the imaged red blood cells can be used to determine whether a patient from whom the sample is obtained has a particular physiological condition or disease. For example, patients with sickle cell disease present with blood cells having an abnormal shape (i.e. in the shape of a sickle). Hence, by obtaining high quality images of aligned red blood cells, it is possible to ensure an accurate diagnosis. Other shape variations in red blood cells, for example red blood cells having thin peripheral area and a large flat central area, whereby the red blood cell appears to have the profile of a bicycle tire, can effectively be imaged using the instant alignment techniques. Similarly, red blood cells having a small central portion, and a thick peripheral area, whereby the red blood cell appears to have the profile of a truck tire, can be imaged for diagnostic purposes. The improved imaging techniques disclosed herein are also useful for evaluating other red blood cell characteristics, such as hemoglobin content, iron content, and the like.

Without being bound by any particular theory, it is believed that a viscosity differential between the viscosity of the sheath fluid and the viscosity of the sample fluid produces a modified parabolic profile, wherein the profile is generally parabolic and has a central bump corresponding to a center area of the flow where the acceleration is increased, and the central bump contributes to alignment of sample particles or intraparticle organelles. According to some embodiments, the velocity difference between the sheath and sample ribbon and the viscosity difference generate shear forces to increase alignment of the organelles or intracellular particles. Exemplary aspects of the sheath fluid parabolic profile are discussed in co-pending U.S. patent application Ser. No. 14/216,533 filed Mar. 17, 2014, the content of which is incorporated herein by reference.

Figure 4L:
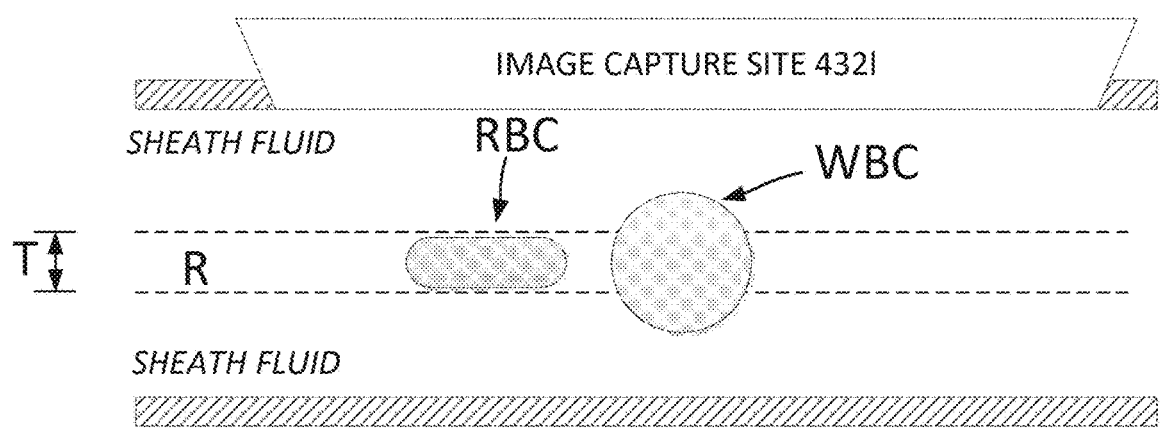

White blood cells are typically larger than red blood cells and platelets. For example, exemplary neutrophils and eosinophils can have a diameter of between about 10 μm and about 12 μm. Exemplary basophils can have a diameter of between about 12 μm and about 15 μm. Exemplary lymphocytes (small) can have a diameter of between about 7 μm and about 8 μm, and exemplary lymphocytes (large) can have a diameter of between about 12 μm and about 15 μm. Exemplary monocytes can have a diameter of between about 12 μm and about 20 μm. The configuration of the particle analysis system, including interaction between the sheath fluid and the fluid sample ribbon as they pass through the flowcell, can operate to compress white blood cells as they travel through the image capture site 432l, as indicated in FIG. 4L. Hence, for example, a central portion of the white blood cell (WBC) can be positioned within the sample fluid ribbon R, and peripheral portions of the white blood cell can be positioned within the sheath fluid. Hence, as the white blood cell is transported through the flowcell by the ribbon, the sides of the white blood cell can extend into the sheath fluid.

According to some embodiments, viscosity differences between the sheath fluid and the sample fluid can operate to align organelles or other intracellular features which are present within cells such as white blood cells. Without being bound by any particular theory, it is believed that shear forces associated with the viscosity differential between the sheath fluid and the sample fluid may act upon the white blood cells so as to align the intracellular features. In some cases, shear forces associated with velocity differentials between the sheath fluid and sample fluid may contribute to such alignment. These alignment effects may be impacted by a size differential between the particles and the sample fluid ribbon as well. For example, where portions of the particles extend out of the sample fluid ribbon and into the surrounding sheath fluid, shear forces associated with the difference in viscosity may have a pronounced effect on the intracellular feature alignment.

As depicted in FIG. 4L, portions of a cell such as a white blood cell can extend into the sheath fluid. Embodiments of the present invention encompass sheath fluid compositions that do not lyse or shred the cell, or otherwise compromise the integrity of the outer cell membrane, when the cell is exposed to the sheath fluid. A viscosity agent in the sheath fluid can operate to retain viability of cells in the sample fluid stream, so as to leave the structure (e.g. shape) and the content (e.g. nucleus) of the cells intact when the cell membrane or wall traverses an interface between the sample fluid ribbon and the sheath fluid envelope or otherwise extends from the sample fluid stream into the flowing sheath fluid.

Often, there are compressive forces acting upon the cells or particles as they flow within the sample fluid ribbon along the flowcell. Hence, the cells may come into contact with the sheath fluid while the cells are in a compressed state or are otherwise subject to compressive forces as a result of a narrowing transition zone. The viscosity agent of the sheath fluid can operate to protect the compressed cells from being shredded or destroyed when they emerge from the thin sample fluid ribbon and become exposed to the viscous sheath fluid, at least until the cells reach the image capture site. Hence, the viscosity agent composition of the sheath fluid can operate as a cellular protectorant, while also enhancing alignment of the particles or intraparticle content.

With reference to FIGS. 4K and 4L, in some instances portions of the cell or particle may extend out of the thin sample fluid ribbon R and into the surrounding sheath fluid. As discussed in co-pending U.S. patent application Ser. No. 14/215,834 filed Mar. 17, 2014, the sheath fluid may contain cellular protectants that inhibit or prevent the sheath fluid from disrupting or lysing the cells or particles. For example, the sheath fluid may contain cellular protectants that preserve the structural integrity of the cells walls as the cells are exposed to the chemical environment of the sheath fluid. Similarly, the cellular protectants may also operate to preserve the structural integrity of the cells walls as the cells experience any shear forces induced by flowcell geometry, and a difference in velocity and/or viscosity between the sample fluid and the sheath fluid. Relatedly, the protectorants can protect the cells or particles from forces resulting from the difference in velocity between the sample fluid and sheath fluid. In this way, the cells retain their viability as they reach the image capture site.

The shear forces can be significant at the interface between the sample fluid ribbon and the sheath fluid envelope. According to some embodiments, flow within the flowcell flowpath can be characterized by a parabolic flow profile. According to some embodiments, particles that are sufficiently large in size will be subjected to some amount of shear force, even where such particles are fully contained within a single fluid phase (i.e. either within the sheath fluid envelope, or alternatively within the sample fluid ribbon).

In some instances, the velocity of the sheath fluid may be different from the velocity of the sample fluid. For example, the sheath fluid may be traveling at 80 mm/second and the sample fluid may be traveling at 60 mm/second. Hence, in some instances, the sample fluid exits the distal cannula port at a sample fluid speed that is slower than the sheath fluid speed of the surrounding envelope. Hence, the sheath fluid can operate to drag the sample fluid along the flowpath of the cannula, thus accelerating the sample fluid and reducing the thickness of the sample fluid ribbon. The sample fluid ribbon maintains the overall volume and mass, so as it travels faster it becomes thinner. According to some embodiments, both the sheath fluid and the sample fluid have a velocity of between about 20 and 200 mm/second at the image capture site.

Typically, the velocity of the sample fluid increases as the sample fluid travels from the cannula exit port to the image capture site. In some instances, the velocity of the sample fluid at the image capture site is 40 times the velocity of the sample fluid as it exits the cannula port at the cannula distal portion. According to some embodiments, the decrease in cross sectional area of the sample ribbon is linear to the increase in velocity. According to some embodiments, if the sheath velocity at the cannula exit is higher than the sample ribbon velocity this will also increase the final sample ribbon velocity at the imaging area.

The sheath fluid can operate to apply significant shear forces on the sample fluid ribbon and on particles within the sample fluid ribbon. Some forces are parallel to the direction of flow, and particles may also encounter forces which are perpendicular to the direction of flow. Often, as the sheath fluid and sample fluid approach the image capture site or zone, the sheath and sample fluids are traveling at or near the same velocity. Hence, the boundary or interface between the sheath and sample fluids as they pass the image capture site may present lower shear forces, as compared to the boundary or interface at the distal cannula exit port or at the tapered transition zone. For example, at the tapered transition zone, the boundary or interface between the sheath fluid envelope and sample fluid ribbon can be in transition, such that the sample ribbon which is initially slower and thicker becomes faster and thinner, and particles in the sampel fluid become more aligned. Put another way, the shear forces may be prominent at the tapered transition zone, and can dissipate toward the image capture site. The shear forces at the image capture site can be represented by a parabolic profile, and can be much lower than the shear forces at the tapered transition zone. Hence, cells or particles can experience higher shear forces as they pass through the transition zone, and lower shear forces as they pass through the image capture site. According to some embodiments, the viscosity difference between the sheath and sample fluids can bring the red blood cells into alignment and thereby into focus. According to some embodiments, the viscosity difference between the sheath and sample fluids can bring white blood cell organelles into alignment and thereby into focus. Relatedly, enhanced imaging results can be obtained for cellular and organelle components that are aligned and brought into focus, resulting from the geometric narrowing of the stream and the velocity difference between the sheath and sample fluids.

As noted elsewhere herein, and with reference to FIGS. 4K and 4L, as the sheath fluid and the sample fluid R flow through a reduction in flowpath size or transition zone of a flowcell, and toward an imaging site 432k or 432l, a viscosity hydrofocusing effect induced by an interaction between the sheath fluid and the sample fluid R associated with a viscosity difference between the sheath fluid viscosity and the sample fluid viscosity, in combination with a geometric hydrofocusing effect induced by an interaction between the sheath fluid and the sample fluid R associated with the reduction in flowpath size or transition zone, provides a target imaging state in at least some of the plurality of particles at the imaging site 432k or 432l.

In some cases, embodiments of the present invention include compositions for use with a hematology system as described herein, such as a sheath fluid or particle and intracellular organelle alignment liquid (PIOAL). Such sheath fluids or PIOALs are suitable for use in a combined viscosity and geometric hydrofocusing visual analyzer. The PIOAL can operate to direct or facilitate flow of a blood sample fluid of a given viscosity through a narrowing flowcell transition zone of the visual analyzer. The PIOAL can include a fluid having a higher viscosity than the viscosity of the sample. A viscosity hydrofocusing effect induced by an interaction between the PIOAL fluid and the sample fluid associated with the viscosity difference, in combination with a geometric hydrofocusing effect induced by an interaction between the PIOAL fluid and the sample fluid associated with the narrowing flowcell transition zone, can be effective to provide a target imaging state in at least some of the plurality of particles at an imaging site of the visual analyzer while retaining viability of cells in the blood sample fluid.

Figure 4M:
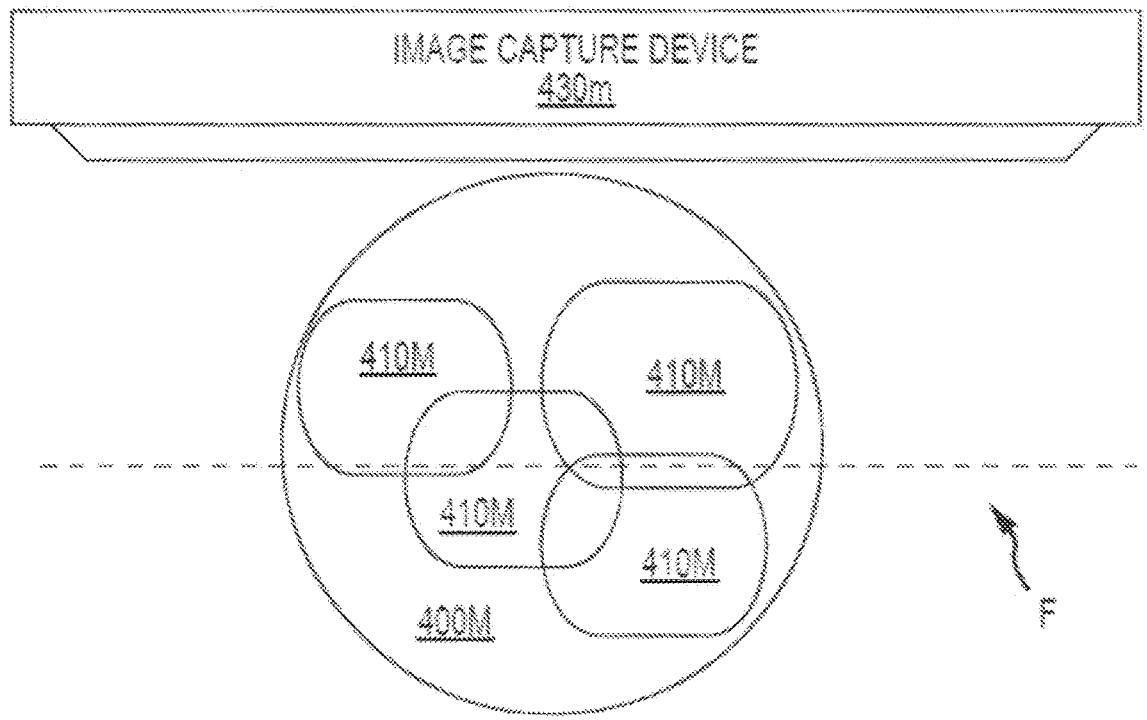
FIGS. 4M and 4N depict exemplary aspects of particles according to embodiments of the present invention.
Figure 4N:
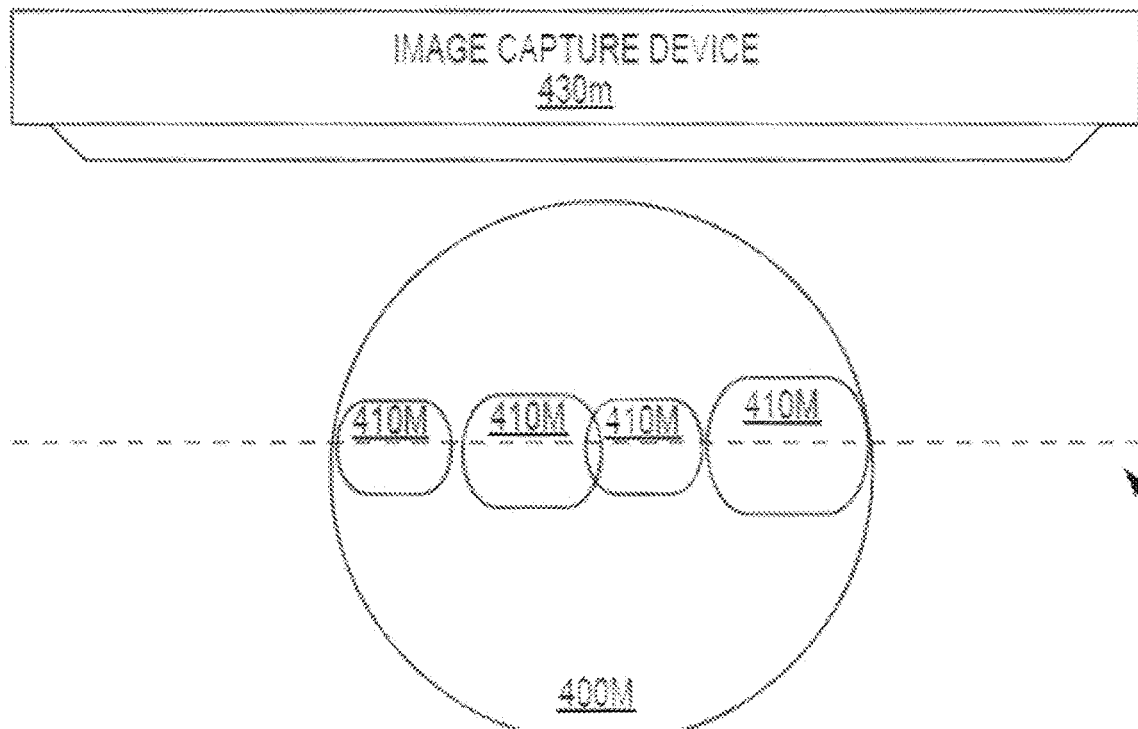

FIG. 4M depicts an exemplary neutrophil 400m (a type of white blood cell) having internal organelles such as lobes 410m. As a result of the viscosity differential between the sample fluid and the sheath fluid, the internal organelles can align within the cell, as indicated by FIG. 4N. Hence, the intracellular organelles can be effectively imaged with an image capture device 430m, without the organelles overlapping one another. That is, instead of the lobes being stacked upon one another as depicted in FIG. 4M, when viewed from the imaging or optical axis of the image capture device the lobes are aligned and sitting side by side as depicted in FIG. 4N. Hence, the lobes can be visualized in the captured imaged more effectively. The internal organelle alignment is a surprising and unexpected result of the viscosity differential between the sample and sheath fluids. Accordingly, enhanced imaging results corresponding to cell alignment and in-focus are achieved using the viscosity differential, hydrodynamic flow, and geometric compression features.

As noted elsewhere herein, and with reference to FIGS. 4M and 4N, as the sheath fluid and the sample fluid R flow through a reduction in flowpath size or transition zone of a flowcell, and toward an imaging site of an image capture device 430m or 430n, a viscosity hydrofocusing effect induced by an interaction between the sheath fluid and the sample fluid R associated with a viscosity difference between the sheath fluid viscosity and the sample fluid viscosity, in combination with a geometric hydrofocusing effect induced by an interaction between the sheath fluid and the sample fluid R associated with the reduction in flowpath size or transition zone, provides a target imaging state in at least some of the plurality of particles at the imaging site. According to some embodiments, the target imaging state may correspond to a distribution of imaging states.

In some cases, the target imaging state can involve a target intraparticle structure orientation (e.g. alignment and/or position) relative to a focal plane at the imaging site. For example, as depicted in FIG. 4N, the internal structures 410m (e.g. intracellular structure, organelle, lobe, or the like) can be oriented relative to the focal plane F. In some cases, the target alignment involves a target intraparticle structure alignment relative to a focal plane F at the imaging site, similar to the particle alignment relationship depicted in FIG. 4K-3. In some cases, the target position involves a target intraparticle structure position relative to a focal plane at the imaging site, similar to the particle position relationship depicted in FIG. 4K-1. In some cases, the target orientation of the intraparticle structure can include both a target alignment relative to the focal plane and also a target position relative to the focal plane. In some cases, the target imaging state can involve a target deformation at the imaging site. For example, as depicted in FIG. 4N, the particle 400m has a compressed shape as compared to the particle shape depicted in FIG. 4M. Hence, it can be seen that operation of the flowcell can produce a lateral compression effect on the particle shapes. Relatedly, the intraparticle features can be positionally or directionally oriented (e.g. aligned with respect to the focal plane F and/or ribbon flow plane) as the particle itself is compressed in shape. According to some embodiments, a velocity difference between the sheath and and sample fluids can produce friction within the flowstream, and a viscosity difference between the sheath and sample fluids can amplify that hydrodynamic friction.

Any of a variety of hematology or blood particle analysis techniques can be performed using images of sample fluid flowing through the flowcell. Often, image analysis can involve determining certain cell or particle parameters, or measuring, detecting, or evaluating certain cell or particle features. For example, image analysis can involve evaluating cell or particle size, cell nucleus features, cell cytoplasm features, intracellular organelle features, and the like. Relatedly, analysis techniques can encompass certain counting or classification methods or diagnostic tests, including white blood cell (WBC) differentials. In some cases, images obtained using the flowcell can support a 5-part WBC differential test. In some cases, images obtained using the flowcell can support a 9-part WBC differential test. Relatedly, with reference to FIG. 4, the processor 440 can include or be in operative association with a storage medium having a computer application that, when executed by the processor, is configured to cause the system 400 to differentiate different types of cells based on images obtained from the image capture device. Similarly, with reference to FIG. 6B the processor 604b can include or be in operative association with a storage medium having a computer application that, when executed by the processor, is configured to cause system 600b or system 642b to differentiate different types of cells based on images obtained from the image capture device. For example, diagnostic or testing techiques can be used to differentiate various cells (e.g. neutrophils, lymphocytes, monocytes, eosinophils, basophils, metamyelocytes, myelocytes, promyelocytes, and blasts).

Figure 4O:
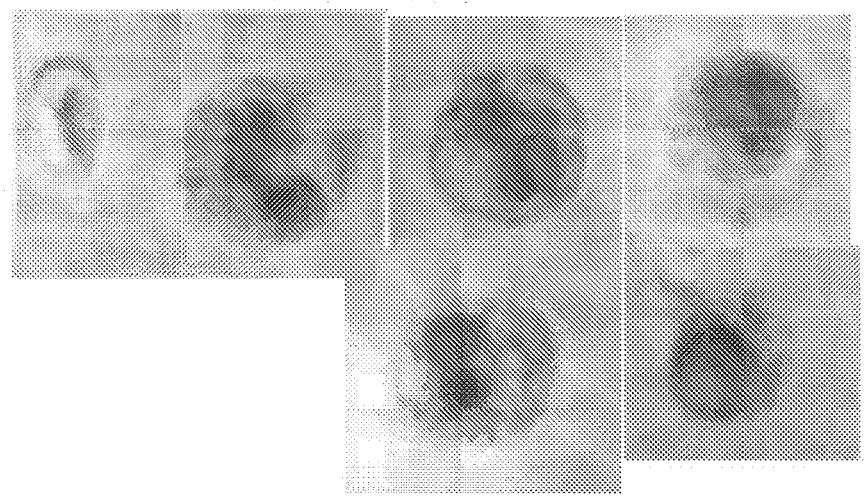
FIG. 4O shows a comparison of images obtained using PIOAL versus images obtained using a non PIOAL sheath fluid according to embodiments of the present invention.
Figure 4O:
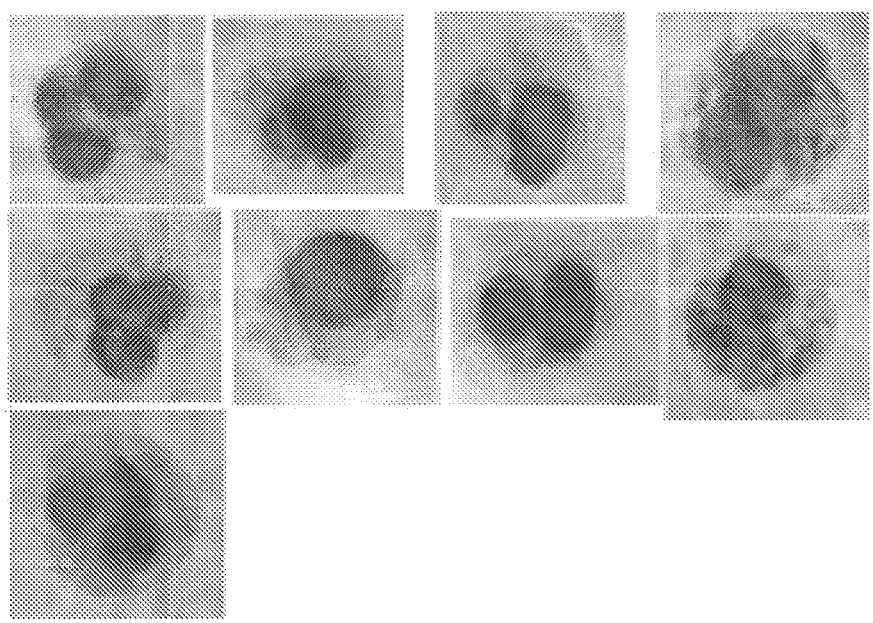

FIG. 4O shows a comparison of images obtained using PIOAL versus images obtained using a non PIOAL sheath fluid. Use of the PIOAL resulted in more in-focus cellular contents such as lobes, cytoplasm, and/or granule. In this example, a PIOAL comprising a viscosity agent (about 30% glycerol) was used to process the sample. The pH was adjusted to a pH of about 6.8 to 7.2 and the sample mixture was made isotonic by (0.9% sodium chloride). The results shown here demonstrate the efficacy of an exemplary PIOAL used on an image analyzer to align cells and intracellular organalles.

Figure 4P:
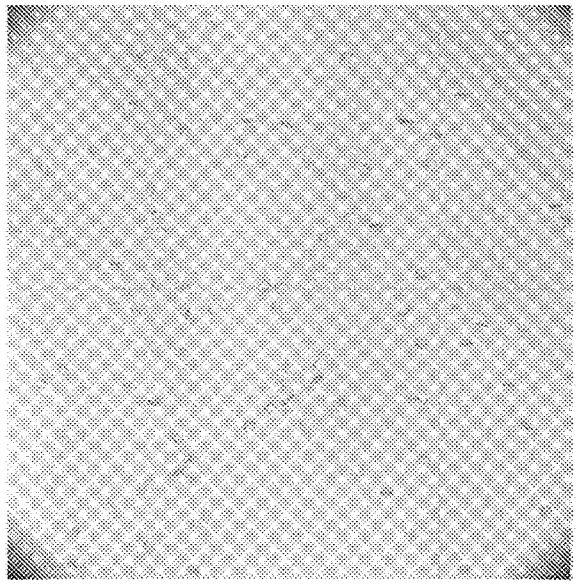
FIGS. 4P and 4Q show a comparison of images obtained using a standard sheath fluid and exemplary PIOAL fluid according to embodiments of the present invention.
Figure 4P:
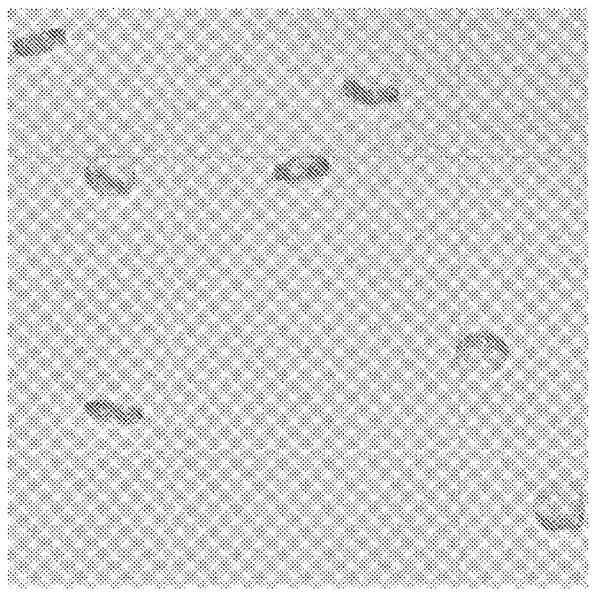
Figure 4Q:
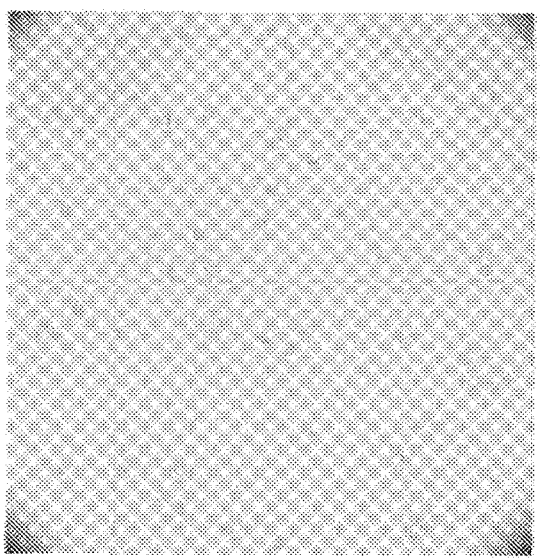
Figure 4Q:
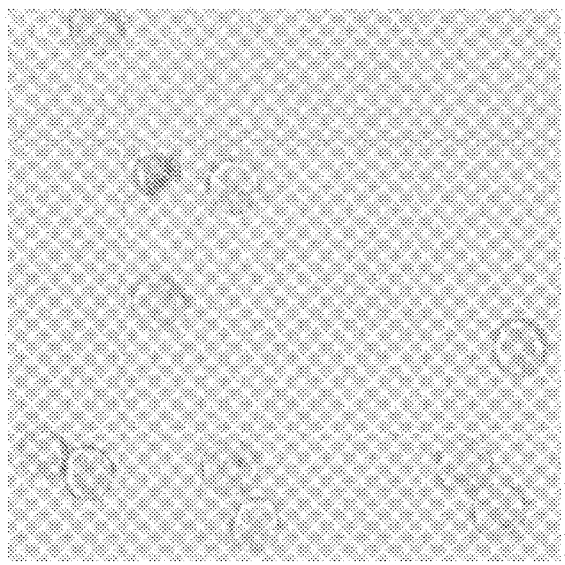

FIGS. 4P and 4Q show a comparison of images obtained using a standard sheath fluid (FIG. P upper and lower panels) versus images obtained using an exemplary PIOAL fluid (FIG. 4Q upper and lower panels). As shown here, the use of PIOAL resulted in an improved RBC alignment. The sample was analyzed using an instrument focusing protocol (on an exemplary target 44 as depicted in FIG. 1) and the target was brought into focus by a visual analyzer. The focusing system was then offset by displacement distance 52, resulting in the particles in the ribbon-shaped sample stream being in focus. The blood sample was previously diluted using a sample diluent. The sample flowed through a cannula and along a flowpath of a flowcell, thereby generating a ribbon-shaped sample stream (e.g. 2 microns in thickness) which was between two layers of PIOAL or standard sheath (in controls). The visual analyzer then generates focused images of the particles in the ribbon-shaped sample stream (e.g. at about 60 frames per second) to be used for analysis. The blood sample is obtained from a subject and processed for analysis by the blood analyzer. Images of RBCs in a flowcell are captured while the sample is processed using a standard sheath fluid or a PIOAL. Relative percentages demonstrate significant improvement in the number of aligned RBCs based on imaging data (e.g. 4P and 4Q). The result demonstrated that PIOAL was efficacious at increasing the percentage of RBC alignment while in flow in the ribbon-shaped sample stream using the focusing instrument/protocols as described herein.

It was also observed that the implementation of PIOAL results in improved alignment based on using increasing levels of glycerol (gly) in symmetric and asymmetric flowcells.

These results provide evidence for the surprising and unexpected discovery that certain PIOAL compositions have unexpected properties aligning cells and re-positioning intracellular structures when used to perform image-based particle/cell analysis.

Dynamic Range Extension

Figure 5:
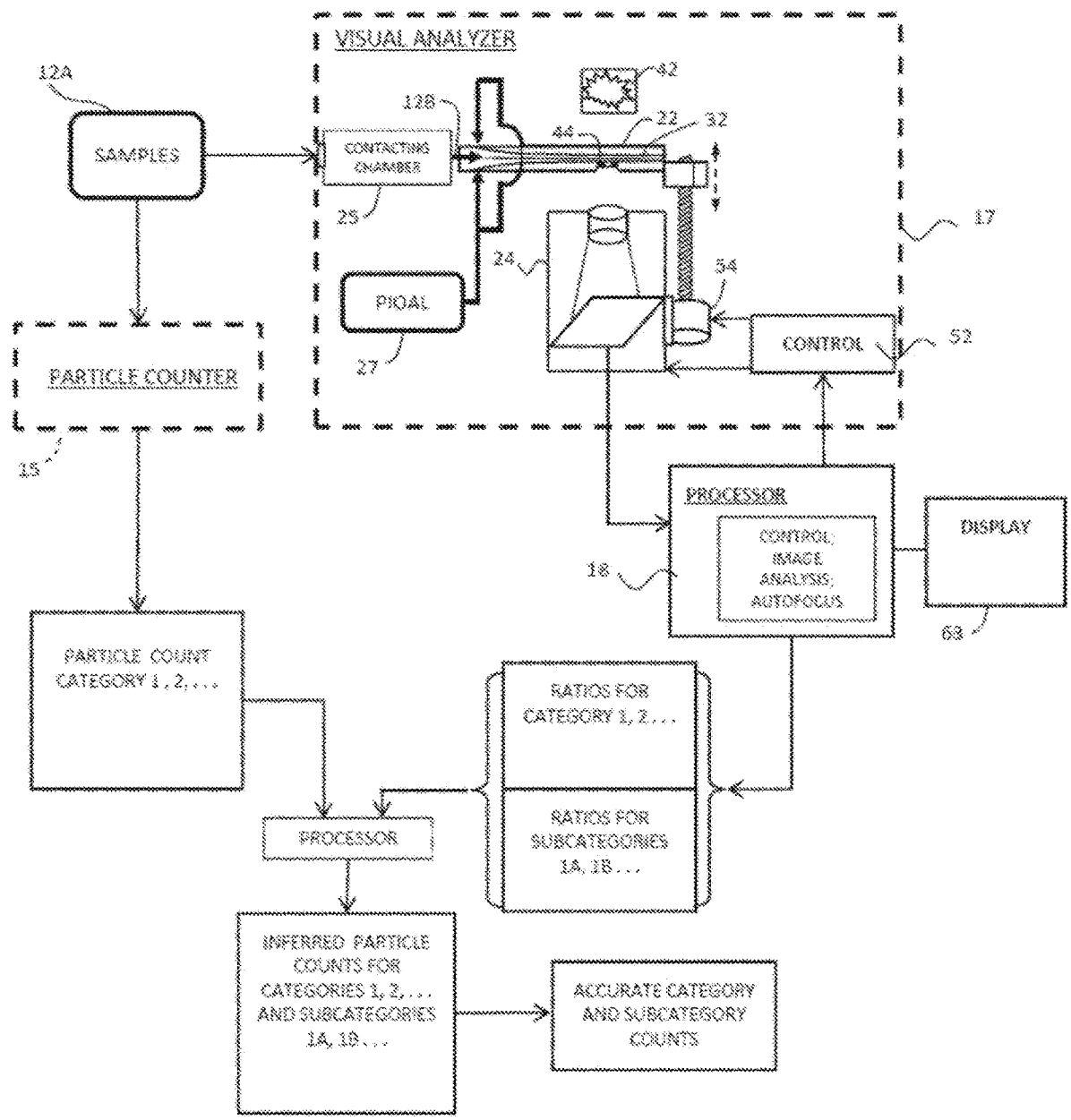
FIG. 5 is a block diagram showing additional aspects of systems and methods for achieving dynamic or detection range extension for particle analysis in blood samples, according to embodiments of the present invention.

FIG. 5 is a block diagram showing additional aspects of systems and methods for achieving dynamic or detection range extension for particle analysis in blood samples, according to embodiments of the present invention. As depicted here, at least one digital processor 18 is coupled to operate the motor drive 54 and to analyze the digitized image from the photosensor array as collected at different focus positions relative to the target autofocus pattern 44. The processor 18 is configured to determine a focus position of the autofocus pattern 44, i.e., to autofocus on the target autofocus pattern 44 and thus establish an optimal distance between the high optical resolution imaging device 24 and the autofocus pattern 44. This can be accomplished by image processing steps such as applying an algorithm to assess the level of contrast in the image at a first distance, which can apply to the entire image or at least at an edge of the autofocus pattern 44. The processor moves the motor 54 to another position and assesses the contrast at that position or edge, and after two or more iterations determines an optimal distance that maximizes the accuracy of focus on the autofocus pattern 44 (or would optimize the accuracy of focus if moved to that position). The processor relies on the fixed spacing between the autofocus target autofocus pattern 44 and the ribbon-shaped sample stream, the processor 18 then controls the motor 54 to move the high optical resolution imaging device 24 to the correct distance to focus on the ribbon-shaped sample stream 32. More particularly, the processor operates the motor to displace the distance between the high optical resolution imaging device and the ribbon-shaped sample stream 32 by the displacement distance 52 (see FIG. 1) by which the ribbon-shaped sample stream is displaced from the target autofocus pattern 44. In this way, the high optical resolution imaging device is focused on the ribbon-shaped sample stream.

According to some embodiments, visual analyzer 17 is an exemplary analyzer 17 of FIG. 1. Visual analyzer 17 can comprise at least one flowcell 22 and at least one imaging device 24 such as a high optical resolution imaging device having an imaging sensor such as a digital camera. Visual analyzer 17 can also comprise a sample injector 29. Sample injector 29 is configured to provide sample 12 into the at least one flowcell 22. Flowcell 22 defines an internal PIOAL flow path that narrows, for example, symmetrically in the flow direction. Flowcell 22 is configured to direct a flow 32 of the sample through a viewing zone in the flowcell 22.

FIG. 5 illustrates the autofocus and other aspect of digital imaging as described. Such techniques can be employed in conjunction with blood cell apparatus that are not based on imaging or perhaps are less image related than the embodiments described, such as Coulter blood cell counters, also known as flow cytometers. Such counters are known for detecting and counting blood cells and particles in fluids, but usually not by imaging. In a counter of that type, a flowcell is arranged to carry a flow of particles enveloped in a fluid. The flowcell narrows to force particles in the flow path into single file. A pair of electrodes or other detectors spanning the flow path produce a count by detection of a pulsed change in electrical impedance, or obstruction of a light path between a light source and photo-detector when cells pass.

Flow cytometers are advantageous because a large number of cells or other particles can be counted, much larger than the number of cells that can be imaged practically in a visual counter. But flow cytometers are not as effective in distinguishing between cells by type, or enabling distinctions between normal and abnormal cells, or distinguishing grouped cells such as platelet clumps, from discrete blood cells. By operating an analyzer, for example, the visual analyzer, as described, through a statistically significant number of image frames of a ribbon-shaped sample stream, a distribution or proportionate ratio of blood cell types can be measured. The proportionate ratios determined from a visual analyzer, or a function thereof, are applied to blood cell counts, and the larger numbers of blood cells counted by the cytometer, albeit with less discrimination or no discrimination as to cell type, to provide an accurate total blood count that exploits the peculiar advantages of both types of analyzers.

According to some embodiments, particle counts can be inferred by applying an algorithm, for example, an algorithm based on a proportionate ratio of particle counts. FIG. 5 illustrates an exemplary apparatus adapted to blood analysis. In some embodiments the particle counter 15 and the visual analyzer 17 may be connected in series other than in parallel. The particle counter 15, may be, for example, a Coulter blood cell counter, which detects and counts blood cells and particles in fluids. In a counter of that type, a flow path (not shown) is arranged to carry a flow of particles enveloped in a fluid. The flow path narrows to force articles in the flow path into single file. A pair of electrodes or other detectors spanning the flow path produce a count by detection of a pulsed change in electrical impedance, or obstruction of a light path between a light source and photo-detector when cells pass. Particle counter 15 is configured to count a large number of cells or other particles. But particle counter 15 might not be able to distinguish between members in subcategories of cells, and/or to distinguish between normal and abnormal cells, or to distinguish grouped cells such as platelet clumps, from discrete blood cells.

Visual analyzer 17 can also comprise at least one contacting chamber 25 configured to provide at least one chemical comprising at least one of a diluent, a permeabilizing agent, a contrast agent effective to generate visual distinctions for particle categorization and/or subcategorization. For example, as shown with reference to FIGS. 1 and 5, the contacted sample is introduced into the flowcell through sample injector 29, and a sheath or intracellular organelle alignment reagent is introduced from injector 27. A diluent can be used for diluting the sample to a suitable concentration. A contrast agent and/or permeabilizing agent is used to generate visual distinctions for categorizing and/or subcategorizing particles. PIOAL is used to align certain type of cells or cellular structures in a direction for better imaging. In some embodiments, the at least one chemical can be applied to contact a sample first and then the treated sample is provided onto visual analyzer 17. Treatment of the sample with the at least addition of at least one chemical can be performed at room temperature. In some embodiments, such a treatment can be performed at a temperature such as 10, 15, 20, 25, 30, 35, 36, 37, 38, 38, 39, 40, 45, 46, 47, 48, 49 or 50° C. The treatment at a selected temperature can be conducted in an incubator which is separate from visual analyzer 17, or on a visual analyzer 17 which is temperature controlled.

In some embodiments, the visual analyzer may have a contrast agent injector for bringing the sample in contact with a contrast agent and/or permeabilizing agent or surfactant. In other embodiments, the sample may be contacted with contrast agent, permeabilizing agent prior to injection into the visual analyzer. In other embodiments, the visual analyzer containing a heating element for heating the sample while in contact with the contrast agent and/or permeabilizing agent, at a controlled temperature for a controlled time. The visual analyzer may also have a cooling element for cooling the sample mixture after the heating step. Exemplarly contrast agent compositions and methods which can be used for processing blood fluid samples are disclosed in copending U.S. patent application Ser. No. 14/216,339 filed Mar. 17, 2014, the content of which is incorporated herein by reference.

By operating the visual analyzer 17 as described, through a statistically significant number of image frames of a ribbon-shaped sample stream, a proportionate ratio of cells in cell categories and/or subcategories can be determined by processor 18. The proportionate ratios determined from visual analyzer 17 are applied to blood cell counts, and the larger numbers of blood cells counted by particle counter 15, albeit with less discrimination or no discrimination as to members within a cell category and/or subcategory, to provide an accurate total blood count that exploits the peculiar advantages of both particle counter 15 and visual analyzer 17.

In addition to providing accurate results, the apparatus comprising a particle counter 15 and a visual analyzer 17 offers significant advantages in improving speed of analysis. In FIG. 5, accurate results of counting different blood cells can be output through display 63. During an analysis process, an operator may interact with processor 18 through a terminal 65. Previously, up to about 25% to 30% of results were reviewed manually by making slides with contrast agent which were examined under a microscope by an operator. In comparison, an exemplary method using the apparatuses of this invention comprises a CBC on a particle counter, and categorizing and/or subcategorizing blood cells in accordance with some embodiments. By operating the apparatus as described in this disclosure, images can be reviewed on the visual analyzer and the samples will require less frequent manual review.

The motor 54 can comprise a geared stepping motor with precision somewhat smaller than the distinguishing features imaged by the high optical resolution imaging device or the digital image capture device, especially aspects of blood cells. Provided that the location of the high optical resolution imaging device 24 is adjusted to locate the position of the optical objective within the width of the ribbon-shaped sample stream, the view of the cell/particle in the ribbon-shaped sample stream is in focus. The autofocus pattern can be located at an edge of a field of view of the high optical resolution imaging device or the digital image capture device, and does not interfere with viewing for that reason.

Furthermore, when the high optical resolution imaging device is moved over the displacement distance and the autofocus pattern goes out of focus, the features that appear in focus are the blood cells as opposed to the autofocus pattern. According to some embodiments, the autofocus pattern can be defined by shapes in the field of view. The shapes are relatively thin discrete forms of a limited size, and therefore after moving by the displacement distance, the forms become substantially invisible in the digitized image when focused on the ribbon-shaped sample stream. A typical displacement distance may be, for example, 50 to 100 µm in a flowcell dimensioned for hematology (blood cell) imaging applications. In some embodiments, the autofocus feature maintains the high optical resolution imaging device within 1 µm of the optimal focus distance.

The flowcell internal contour and the PIOAL and sample flow rates can be adjusted such that the sample is formed into a ribbon shaped stream. The stream can be approximately as thin as or even thinner than the particles that are enveloped in the ribbon-shaped sample stream. White blood cells may have a diameter around 10 µm, for example. By providing a ribbon-shaped sample stream with a thickness less than 10 µm, the cells may be oriented when the ribbon-shaped sample stream is stretched by the sheath fluid, or PIOAL. Surprisingly stretching of the ribbon-shaped sample stream along a narrowing flowpath within PIOAL layers of different viscosity than the ribbon-shaped sample stream, such as higher viscosity, advantageously tends to align non-spherical particles in a plane substantially parallel to the flow direction, and apply forces on the cells, improving the in-focus contents of intracellular structures of cells. The optical axis of the high optical resolution imaging device 24 is substantially normal (perpendicular) to the plane of the ribbon-shaped sample stream. The linear velocity of the ribbon-shaped sample stream at the point of imaging may be, for example, 20-200 mm/second. In some embodiments, the linear velocity of the ribbon-shaped sample stream may be, for example, 50-150 mm/second.

The ribbon-shaped sample stream thickness can be affected by the relative viscosities and flow rates of the sample fluid and the PIOAL. The source 25 of the sample and/or the source 27 of the PIOAL, for example comprising precision displacement pumps, can be configured to provide the sample and/or the PIOAL at controllable flow rates for optimizing the dimensions of the ribbon-shaped sample stream 32, namely as a thin ribbon at least as wide as the field of view of the high optical resolution imaging device 24.

In one embodiment, the source 27 of the PIOAL is configured to provide the PIOAL at a predetermined viscosity. That viscosity may be different than the viscosity of the sample, and can be higher than the viscosity of the sample. The viscosity and density of the PIOAL, the viscosity of the sample material, the flow rate of the PIOAL and the flow rate of the sample material are coordinated to maintain the ribbon-shaped sample stream at the displacement distance from the autofocus pattern, and with predetermined dimensional characteristics, such as an advantageous ribbon-shaped sample stream thickness.

In a practical embodiment, the PIOAL has a higher linear velocity than the sample and a higher viscosity than the sample, thereby stretching the sample into the flat ribbon. The PIOAL viscosity can be up to 10 centipoise.

In the embodiment depicted in FIG. 5, the same digital processor 18 that is used to analyze the pixel digital image obtained from photosensor array is also used to control the autofocusing motor 54. However the high optical resolution imaging device 24 is not autofocused for every image captured. The autofocus process can be accomplished periodically or for example when temperature or other process changes are detected by appropriate sensors, or when image analysis detects a potential need for refocusing. It is also possible in other embodiments to have the hematology image analysis accomplished by one processor and to have a separate processor, optionally associated with its own photosensor array, arranged to handle the steps of autofocusing to a fixed target 44.

In FIG. 5, the at least one said digital processor 18 is configured to autofocus at programmed times or in programmed conditions or on user demand, and also is configured to perform image based categorization and subcategorization of the particles. Exemplary particles include cells, white blood cells, red blood cells and the like.

In one embodiment, the at least one said digital processor 18 is configured to detect an autofocus re-initiation signal. The autofocus re-initiation signal can be triggered by a detected change in temperature, a decrease in focus quality as discerned by parameters of the pixel image date, passage of time, or user-input. Advantageously, it is not necessary to recalibrate in the sense of measuring the displacement distance 52 to recalibrate. Optionally, the autofocus can be programmed to re-calibrate at certain frequencies/intervals between runs for quality control and or to maintain focus.

The displacement distance 52 varies slightly from one flowcell to another, but remains constant for a given flowcell. As a setup process when fitting out an image analyzer with a flowcell, the displacement distance is first estimated and then during calibration steps wherein the autofocus and imaging aspects are exercised, the exact displacement distance for the flowcell is determined and entered as a constant into the programming of processor 18.

Figure 6:
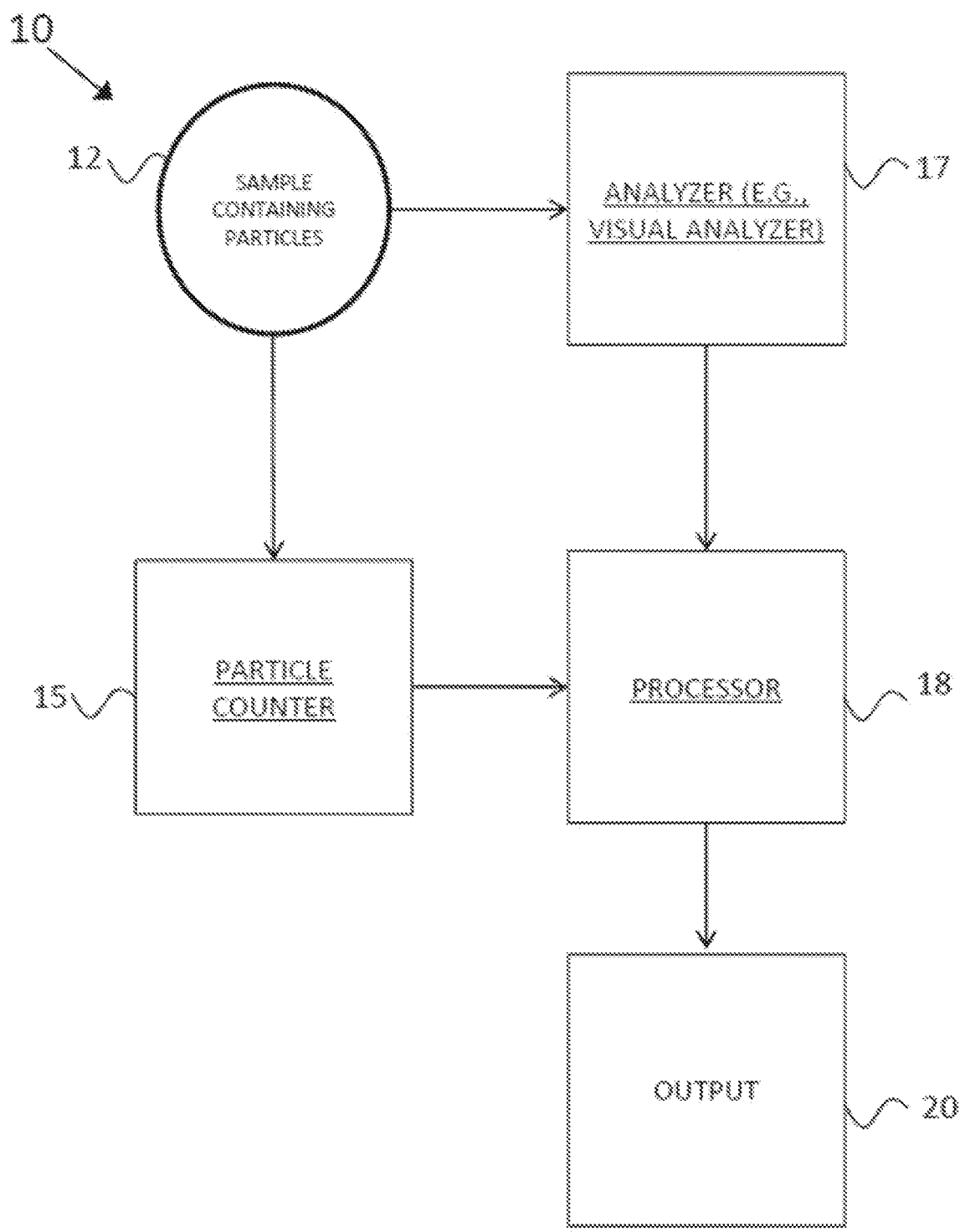
FIG. 6 shows an exemplary apparatus for analyzing a sample according to embodiments of the present invention.

Referring to FIG. 6, an exemplary apparatus 10 for analyzing a sample 12 containing particles includes a particle counter 15 having at least one detection range, an analyzer 17, and a processor 18 in accordance with some embodiments. The block diagram of FIG. 6 is for the purpose of illustration. Particle counter 15, analyzer 17, and processor 18 may or may not be connected to each other. In some embodiments the processor may be coupled to the analyzer and/or particle counter. In other embodiments the processor may be a component of the analyzer and/or particle counter.

Particle counter 15 comprises at least one channel, and is configured to provide a particle count for at least one category and/or subcategory of particles. In some embodiments, a particle counter 15 comprises at least two channels for different categories and/or subcategories of particles. In some embodiments, particles are counted through sensing electrical impedance or light scatter of the sample. An example of a suitable particle counter 15 includes but is not limited to a flow cytometer. In some embodiments, detection may take place in each of a plurality of channels responsive to different physical properties, either simultaneously or sequentially.

Analyzer 17 is configured to differentiate different categories and/or subcategories and corresponding members of each category and/or subcategory of particles. Examples of a suitable analyzer 17 include but are not limited to a visual analyzer, a digital camera, or any other pixel data analyzer which can capture pixel data, and is programmed to discriminate for attributes represented in a pixel file. Processor 18 and analyzer 17 are configured to apply an algorithm, such as determining a proportionate ratio of the counts of two categories or two corresponding subcategories of particles, and apply such a proportionate ratio to the particle count of at least one category and/or subcategory of particles obtained in at least one channel of particle counter 15. After data analysis, processor 18 provides, at output 20, an accurate measure of concentration of each category and each corresponding subcategory of particles in sample 12.

In some embodiments, in sample 12, at least a first category and/or subcategory of particles can be present at a concentration outside a detection range applicable to the first category and/or subcategory of particles while at least a second category and/or subcategory of particles is present at a concentration within a detection range applicable to the second category and/or subcategory of the particles. The concentration of the second category and/or subcategory of particles is determined on particle counter 15. A proportionate ratio of the first category and/or subcategory to the second category and/or subcategory of particles is determined on analyzer 17. The concentration of particles in the first category and/or subcategory is calculated on processor 18 at least in part by applying such a proportionate ratio to the concentration of the second category and/or subcategory of particles.

In some embodiments, a category and/or subcategory of particles detected in the at least one channel of particle counter 15 can comprise at least two classes of particles. And each class of particles may comprise a plurality of subclasses. Particle counter 15 is configured to detect a plurality of particles that meet one or more selection criteria, for example, based on a predetermined size range, and to provide a particle count thereof. The selection criteria encompass members of at least two classes of particles. Analyzer 17 and processor 18 are programmed to distinguish the members of the at least two categories and/or subcategories of particles. A distribution of each the members over at least two categories and/or subcategories are determined on processor 18. Processor 18 uses such a distribution to correct the particle count for the members of at least one of the at least two categories and/or subcategories obtained on particle counter 15.

More particularly, apparatus 10 can be used for identifying and quantifying different blood cells including RBCS, WBCs, PLTs, and other blood cells, fetal cells, or bacterial cells, viral particles, parasites, cysts, including parasitic cysts, crystals, or fragments thereof or other cell fragments in a sample.

Figure 6A:
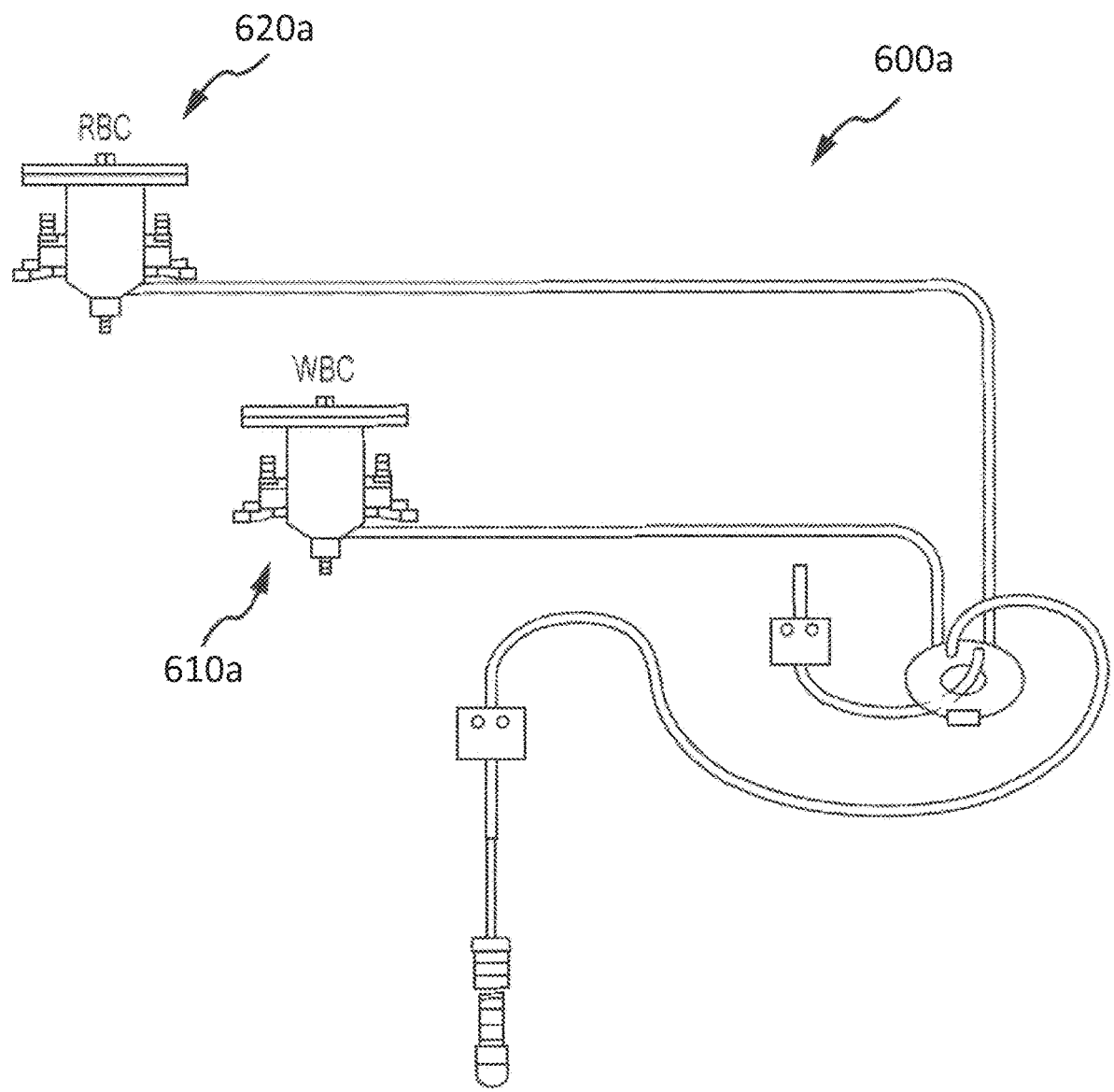
FIG. 6A depicts aspects of an exemplary counter or counting module according to embodiments of the present invention.

FIG. 6A depicts aspects of an exemplary counter or counting module 600a, according to embodiments of the present invention. Such counters can operate to control or carry out various mechanical functions as well as electronic and photometric measurement functions for WBC, RBC and PLT cell counting and hemoglobin measurements. Exemplary counters can be used to prepare the samples for CBC analysis, and to generate CBC parameter measurements via aperture bath assemblies (e.g. WBC bath 610a and RBC bath 620a). According to some embodiments, the counter 15 of FIG. 6 can be represented by counter 600a of FIG. 6A. Similarly, according to some embodiments, the counter 15 of FIG. 5 can be represented by counter 600a of FIG. 6A. According to some embodiments, the counter 722 of FIG. 7 can be represented by counter 600a of FIG. 6A.

Cellular elements of the blood (e.g. erythrocytes, leukocytes, and platelets) can be counted using electrical impedance methods. For example, an aspirated whole blood sample can be divided into two aliquots and mixed with an isotonic diluent. The first dilution can be delivered to the RBC aperture bath 620a, and the second can be delivered to the WBC aperture bath 610a. In the RBC chamber, both RBCs and platelets can be counted and discriminated by electrical impedance as the cells pass through sensing apertures. For example, particles between 2 and 20 fL can be counted as platelets, and those greater than 36 fL can be counted as RBCs. For the WBC chamber processing, an RBC-lysing reagent can be added to the WBC dilution aliquot to lyse RBCs and release hemoglobin, and then WBCs can be counted by impedance in sensing apertures of the WBC bath. In some instances, the baths may include multiple apertures. Hence, for example, a blood cell count used in a blood cell enumeration technique may be obtained using an RBC triple aperture bath.

An exemplary CBC sample preparation technique may include two processes, sample acquisition and sample delivery. Sample acquisition may occur when 165 uL of patient sample is aspirated and directed to a Blood Sampling Valve (BSV). The BSV can operate to direct specific volumes of the patient sample with the processing reagents for delivery to the two triple-aperture baths. The patient sample and the processing reagents can be delivered to the bottom of aperture baths at an angle that, with a round design, allow the sample and reagents to thoroughly mix without mixing bubbles. The sample can then be prepared for measurement and analysis. According to some embodiments, in the WBC bath, 6.0 mL (±1.0%) of diluent and 28 uL of sample can be combined with 1.08 mL (+1.0%) of DxH cell lyse for a final dilution of 1:251. According to some embodiments, in the RBC bath, 10 mL (±1.0%) of diluent and 1.6 uL, of sample can be combined for a final dilution of 1:6250. After the patient sample and reagents are mixed, vacuum and aperture current can be applied to the apertures for the measurements of cell count and cell volume. The RBC and PLT counts can also include the application of sweep flow to prevent recirculation of cells near the aperture. In certain embodiments, data acquisition for the RBC and PLT can be up to a maximum of 20 seconds and for the WBC a maximum of 10 seconds. In certain embodiments, all analog pulses generated by the aperture assemblies can be amplified by a preamp card and then sent to a CBC signal conditioner analyzer card for analog-to-digital conversion and parameter extraction. According to some embodiments, a system can be used to measure multiple parameters for each cellular event, and a digital parameter extraction process can be used to provide digital measurements such as time, volume (pulse attributes including amplitude and pulse width), count and count rate, and wait time. Such measurements can be used for pulse editing, coincidence correction, count voting, generation of histograms for WBC, RBC and PLT, histogram voting, pattern analysis, and interference correction, and the like.

Figure 6B:
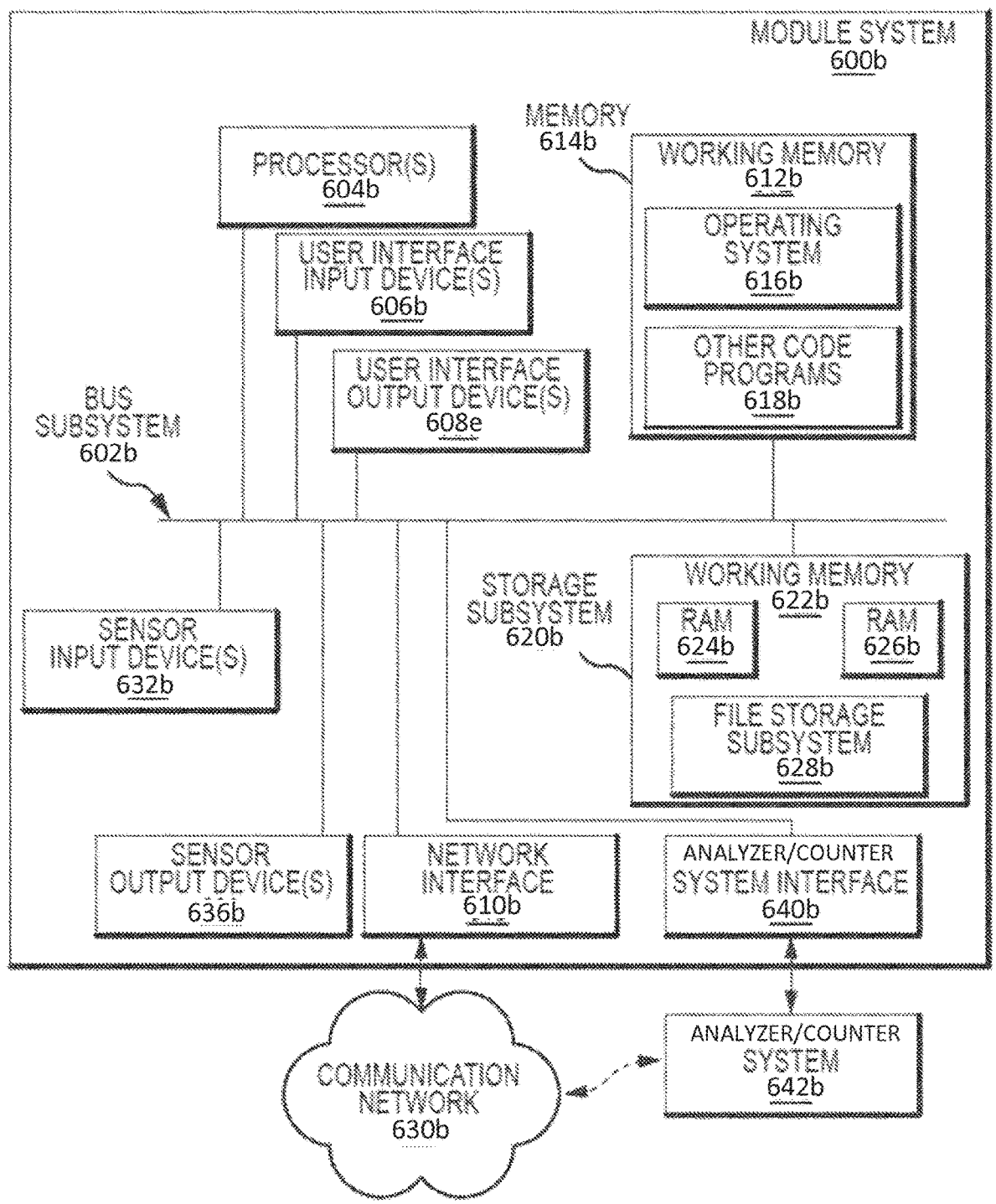
FIG. 6B depicts aspects of a module system according to embodiments of the present invention.

FIG. 6B is a simplified block diagram of an exemplary module system that broadly illustrates how individual system elements for a module system 600b may be implemented in a separated or more integrated manner. Module system 600b may be part of or in connectivity with a particle analysis system for imaging particles in a blood sample fluid, according to embodiments of the present invention. Module system 600b is well suited for producing data or instructions related to dynamic range extension techniques, receiving input related to dynamic range extension techniques, and/or processing information or data related to dynamic range extension techniques, as described elsewhere herein. In some instances, module system 600b includes hardware elements that are electrically coupled via a bus subsystem 602b, including one or more processors 604b, one or more input devices 606b such as user interface input devices, and/or one or more output devices 608b such as user interface output devices. In some instances, system 600b includes a network interface 610b, and/or an analyzer/counter system interface 640b that can receive signals from and/or transmit signals to an analyzer/counter system 642b. In some instances, an analyzer/counter system 642b can include an analyzer 17 and/or a particle counter 15 as depicted in FIG. 6. In some instances, system 600b includes software elements, for example shown here as being currently located within a working memory 612b of a memory 614b, an operating system 616b, and/or other code 618b, such as a program configured to implement one or more aspects of the techniques disclosed herein.

In some embodiments, module system 600b may include a storage subsystem 620b that can store the basic programming and data constructs that provide the functionality of the various techniques disclosed herein. For example, software modules implementing the functionality of method aspects, as described herein, may be stored in storage subsystem 620b. These software modules may be executed by the one or more processors 604b. In a distributed environment, the software modules may be stored on a plurality of computer systems and executed by processors of the plurality of computer systems. Storage subsystem 620b can include memory subsystem 622b and file storage subsystem 628b. Memory subsystem 622b may include a number of memories including a main random access memory (RAM) 626b for storage of instructions and data during program execution and a read only memory (ROM) 624b in which fixed instructions are stored. File storage subsystem 628b can provide persistent (non-volatile) storage for program and data files, and may include tangible storage media which may optionally embody sample, patient, treatment, assessment, or other data. File storage subsystem 628b may include a hard disk drive, a floppy disk drive along with associated removable media, a Compact Digital Read Only Memory (CD-ROM) drive, an optical drive, DVD, CD-R, CD RW, solid-state removable memory, other removable media cartridges or disks, and the like. One or more of the drives may be located at remote locations on other connected computers at other sites coupled to module system 600b. In some instances, systems may include a computer-readable storage medium or other tangible storage medium that stores one or more sequences of instructions which, when executed by one or more processors, can cause the one or more processors to perform any aspect of the techniques or methods disclosed herein. One or more modules implementing the functionality of the techniques disclosed herein may be stored by file storage subsystem 628b. In some embodiments, the software or code will provide protocol to allow the module system 600b to communicate with communication network 630b. Optionally, such communications may include dial-up or internet connection communications.

It is appreciated that system 600b can be configured to carry out various aspects of methods of the present invention. For example, processor component or module 604b can be a microprocessor control module configured to receive signals or data from a sensor input device or module 632b, from a user interface input device or module 606b, and/or from an analyzer/counter system 642b, optionally via an analyzer/counter system interface 640b and/or a network interface 610b and a communication network 630b. In some instances, sensor input device(s) may include or be part of a particle analysis system that is equipped to obtain images of blood fluid samples. In some instances, user interface input device(s) 606b and/or network interface 610b may be configured to receive image parameter signals generated by a particle analysis system that is equipped to obtain image parameters. In some instances, analyzer/counter system 642b may include or be part of a particle analysis system that is equipped to obtain image parameters and/or counting parameters related to blood fluid samples.

Processor component or module 604b can also be configured to transmit particle analysis parameter signals or image parameter signals, optionally processed according to any of the techniques disclosed herein, to sensor output device or module 636b, to user interface output device or module 608b, to network interface device or module 610b, to analyzer/counter system interface 640b, or any combination thereof. Each of the devices or modules according to embodiments of the present invention can include one or more software modules on a computer readable medium that is processed by a processor, or hardware modules, or any combination thereof. Any of a variety of commonly used platforms, such as Windows, MacIntosh, and Unix, along with any of a variety of commonly used programming languages, may be used to implement embodiments of the present invention.

User interface input devices 606b may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices 606b may also download a computer executable code from a tangible storage media or from communication network 630b, the code embodying any of the methods or aspects thereof disclosed herein. It will be appreciated that terminal software may be updated from time to time and downloaded to the terminal as appropriate. In general, use of the term "input device" is intended to include a variety of conventional and proprietary devices and ways to input information into module system 600b.

User interface output devices 606b may include, for example, a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from module system 600b to a user.

Bus subsystem 602b provides a mechanism for letting the various components and subsystems of module system 600b communicate with each other as intended or desired. The various subsystems and components of module system 600b need not be at the same physical location but may be distributed at various locations within a distributed network. Although bus subsystem 602b is shown schematically as a single bus, alternate embodiments of the bus subsystem may utilize multiple busses.

Network interface 610b can provide an interface to an outside network 630b or other devices. Outside communication network 630b can be configured to effect communications as needed or desired with other parties. It can thus receive an electronic packet from module system 600b and transmit any information as needed or desired back to module system 600b. As depicted here, communication network 630b and/or analyzer/counter system interface 642b may transmit information to or receive information from an analyzer/counter system 642b that is equipped to obtain images or image parameters and/or counting parameters corresponding to blood fluid samples.

In addition to providing such infrastructure communications links internal to the system, the communications network system 630b may also provide a connection to other networks such as the interne and may comprise a wired, wireless, modem, and/or other type of interfacing connection.

It will be apparent to the skilled artisan that substantial variations may be used in accordance with specific requirements. For example, customized hardware might also be used and/or particular elements might be implemented in hardware, software (including portable software, such as applets), or both. Further, connection to other computing devices such as network input/output devices may be employed. Module terminal system 600*b* itself can be of varying types including a computer terminal, a personal computer, a portable computer, a workstation, a network computer, or any other data processing system. Due to the ever-changing nature of computers and networks, the description of module system 600*b* depicted in FIG. 6B is intended only as a specific example for purposes of illustrating one or more embodiments of the present invention. Many other configurations of module system 600*b* are possible having more or less components than the module system depicted in FIG. 6B. Any of the modules or components of module system 600*b*, or any combinations of such modules or components, can be coupled with, or integrated into, or otherwise configured to be in connectivity with, any of the particle analysis and/or imaging system embodiments disclosed herein. Relatedly, any of the hardware and software components discussed above can be integrated with or configured to interface with other medical assessment or treatment systems used at other locations.

In some embodiments, the module system 600*b* can be configured to receive one or more image parameters of a blood fluid sample at an input module. Image parameter data can be transmitted to an assessment module where diagnostic or other results can be predicted or determined based on analysis of the image data. Image or diagnostic data can be output to a system user via an output module. In some cases, the module system 600*b* can determine diagnostic results for a blood fluid sample, for example by using a diagnostic module. The diagnostic information can be output to a system user via an output module. Optionally, certain aspects of the diagnosis can be determined by an output device, and transmitted to a diagnosis system or a sub-device of a diagnosis system. Any of a variety of data related to the blood fluid samples or patients from whom samples are obtained can be input into the module system, including age, weight, sex, treatment history, medical history, and the like. Parameters of treatment regimens or diagnostic evaluations can be determined based on such data.

Relatedly, in some instances a system includes a processor configured to receive the image data as input. Optionally, a processor, storage medium, or both, may be incorporated within a hematology or particle analysis machine. In some instances, the hematology machine may generate image data or other information for input into the processor. In some instances, a processor, a storage medium, or both, can be incorporated within a computer, and the computer can be in communication with a hematology machine. In some instances, a processor, a storage medium, or both, can be incorporated within a computer, and the computer can be in remote communication with a hematology machine via a network.

Figure 7:
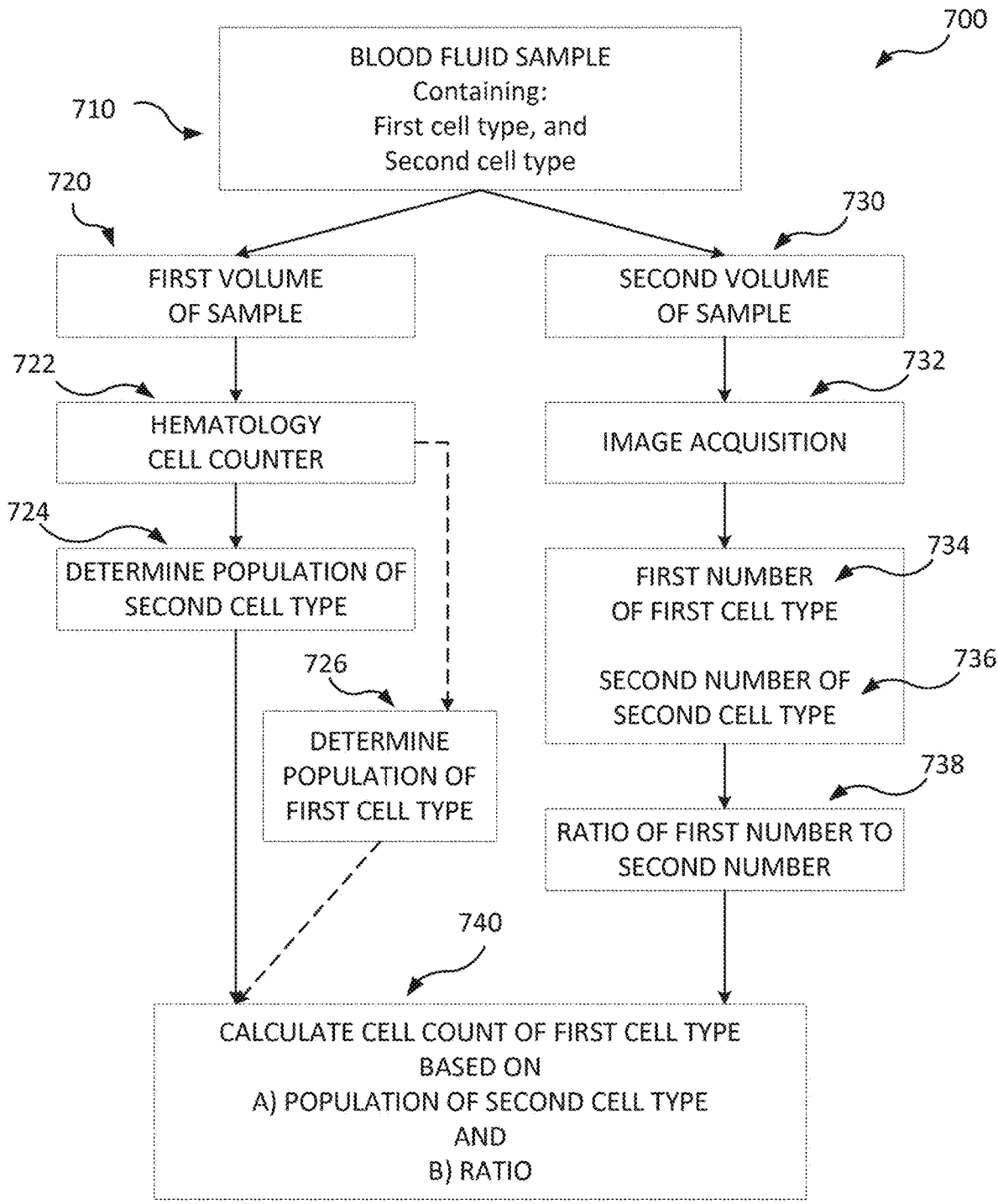
FIG. 7 depicts aspects of systems and methods for measuring a quantity of a first cell type in a blood fluid sample according to embodiments of the present invention.

FIG. 7 depicts aspects of systems and methods for measuring a quantity of a first cell type in a blood fluid sample, where the sample also includes a second cell type, according to embodiments of the present invention. As shown here, the method 700 can include obtaining a first volume of sample 720 and a second volume of sample 730 from the blood fluid sample 710. As indicated at step 724, the method may include determining a population of the second cell type in the first volume 720 of the sample by flowing the first volume through a hematology cell counter 722. Often, cell counter 722 is suitable for accurately counting cells when there is a sufficient amount of an electrically distinguishable type of cell in the sample, and not when the cell type amount exceeds a certain limit or threshold. Cell counters may be used to count red blood cells or the total number of other components (e.g. large components) in a blood sample in a short amount of time. In some cases, cell counters may encounter challenges when discriminating between white blood cells and other components (e.g. large components) in blood, or which there may be several different species, but with a relatively small number each.

Further, method 700 may include acquiring images of a first number of the first type cells and a second number of the second cell types, as indicated by step 732, by injecting the second volume 730 of the sample into a sheath fluid flowing within a flowcell so as to provide a sample stream having a thickness and a width greater than the thickness, the acquired images being acquired along an image path traversing the thickness of the sample stream. In some cases, the image acquisition 732 can be performed using an analyzer 17 as depicted in FIG. 5 and/or FIG. 6. In some cases, analyzers can efficiently discriminate between white blood cells, giant platelets, and other large components in blood fluid sample. However, there may be challenges when using such analyzers to obtain a complete particle count in a sample. Further, in some instances it may not be desirable to use the analyzer to obtain certain counts (e.g. a count of all red blood cells) because such counting procedures may also involve performing a characterization of the particles as well, in addition to obtaining the count. According to some embodiments, the analyzer is used to obtain images for only a percentage or portion of the sample which is processed through the analyzer.

As depicted in FIG. 7, the method 700 may include determining a ratio of the first number of the first cell type 734 to the second number of the second cell type 736 using the acquired images, as indicated at step 738. Methods also include calculating a cell quantity measure of the first cell type in the sample using the ratio 738 and the population of the second cell type 724, as indicated at step 740.

According to some embodiments, the cell quantity measure calculated at step 740 is a cell concentration for the first cell type in the blood fluid sample 710. In some cases, the cell quantity measure calculated at step 740 is a cell count for the first cell type in the blood fluid sample 710. In some cases, the cell counter 722 has a first accuracy associated with counting of the first cell type and a second accuracy associated with counting the second cell type, where the second accuracy is superior to or higher than the first accuracy. In some cases, (see, e.g. FIGS. 10A and 10B) the hematology cell counter 722 has a desired accuracy range, and the desired accuracy range extends between a minimum population of cells in the first volume 720 and a maximum population of cells in the first volume 720, where the population of the second cell type in the volume determined at step 724 is within the desired accuracy range, and where the cell quantity measure of the first cell type of the sample calculated at step 740 is outside the desired accuracy range.

As further depicted in FIG. 7, (and with continued reference to FIGS. 10A and 10B) methods may optionally include determining a population of the first cell type 726 in the first volume of the sample as a result of flowing the first volume through the hematology cell counter 722. The determined population of the first cell type 726 in the first volume may be above or below a desired accuracy range for the first cell type, and may also be different from the cell quantity measure of the first cell type as calculated in step 740. In some cases, (e.g. FIG. 10A), the determined population of the first cell type 726 is zero. In some cases, (e.g. FIG. 10B), the determined population of the first cell type 726 is greater than zero.

According to some embodiments of the present invention, the hematology cell counter 722 can include a sensor mechanism that detects a change in electrical impedance in response to a second type cell flowing through the cell counter. According to some embodiments, the hematology cell counter 722 includes a sensor mechanism that detects an obstruction of a light path in response to a second type cell flowing through the cell counter.

In some cases, the hematology cell counter 722 has a minimum detectable concentration limit and a maximum detectable concentration limit for the first cell type, and a minimum detectable concentration limit and a maximum detectable concentration limit for the second cell type. The determined population of the second cell type 724 can be based on a detected concentration parameter for the second cell type that is above the minimum limit and below the maximum limit for the second cell type. The first cell type can be present at a concentration that is either below the minimum limit or above the maximum limit for the first cell type.

In some cases, the hematology cell counter 722 has a minimum detectable volume limit and a maximum detectable volume limit for the first cell type, and a minimum detectable volume limit and a maximum detectable volume limit for the second cell type. The determined population of the second cell type 724 can be based on a detected volume parameter for the second cell type that is above the minimum limit and below the maximum limit for the second cell type. The first cell type can be present at a volume parameter that is either below the minimum limit or above the maximum limit for the first cell type.

In some cases, the hematology cell counter 722 has a minimum detectable size limit and a maximum detectable size limit for the first cell type, and a minimum detectable size limit and a maximum detectable volume size for the second cell type. The determined population of the second cell type 724 can be based on a detected size parameter for the second cell type that is above the minimum limit and below the maximum limit for the second cell type. The first cell type can be present at a size parameter that is either below the minimum limit or above the maximum limit for the first cell type.

According to some embodiments of the present invention, (refer FIGS. 13b, c), the determination of the population of the second cell type 724 in the first volume of the sample includes grouping together cells of the first cell type and cells of the second cell type. In some cases, methods may also include calculating a cell quantity measure of the second cell type in the sample using the ratio and the population of the second cell type. In some cases (e.g. as depicted in FIG. 10D), the determination of the population of the second cell type 724 in the first volume of the sample includes grouping together cells of the first cell type and cells of the second cell type, and determining a population of the first cell type 726 in the first volume of the sample as a result of flowing the first volume through the hematology cell counter 722. The cell quantity measure of the first cell type in the sample as calculated in step 740 can use the ratio 738, the population of the second cell type 724, and the population of the first cell type 726.

Figure 8:
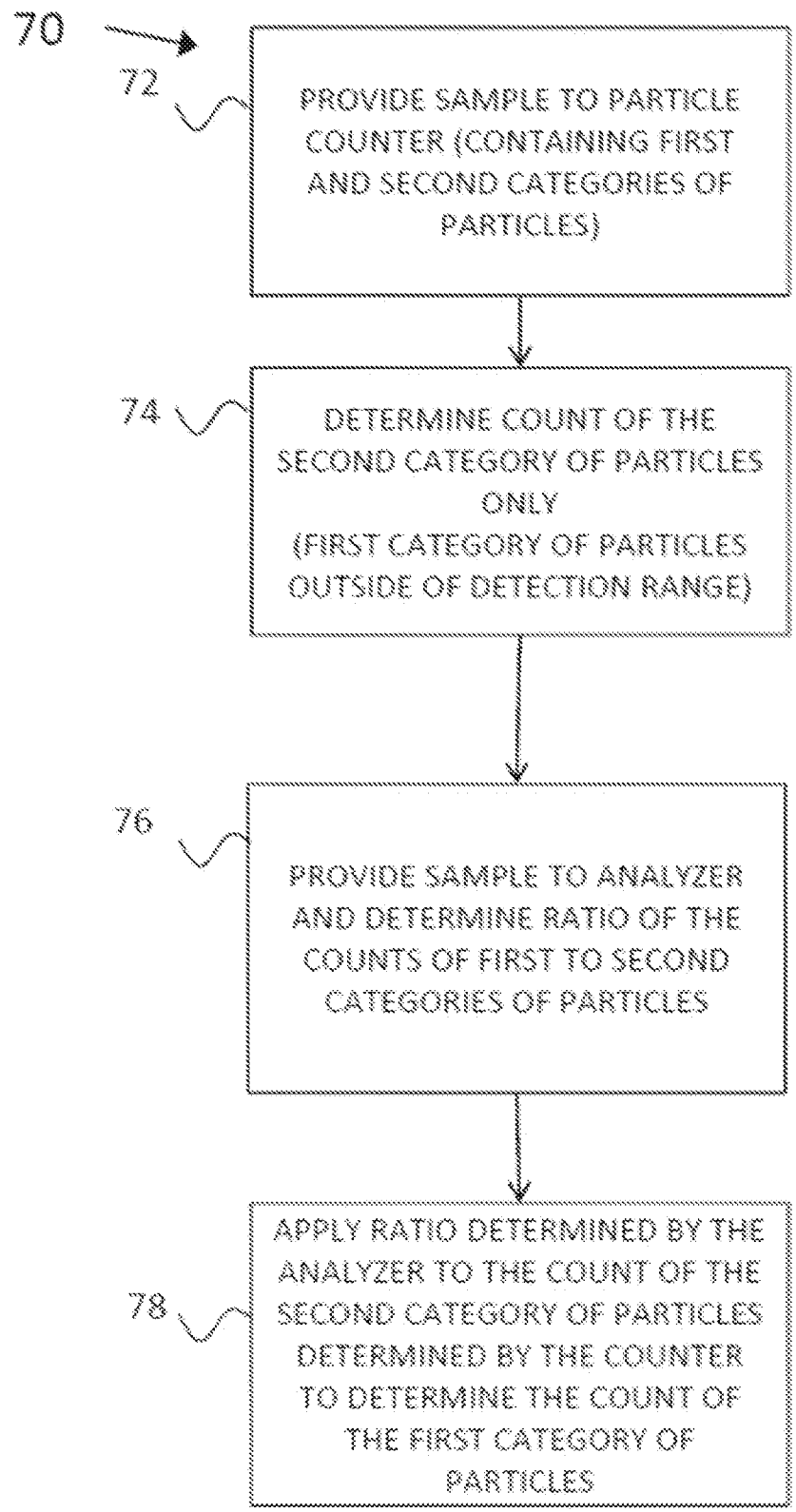
FIG. 8 shows a method for analyzing a sample containing particles according to embodiments of the present invention.
Figure 10A:
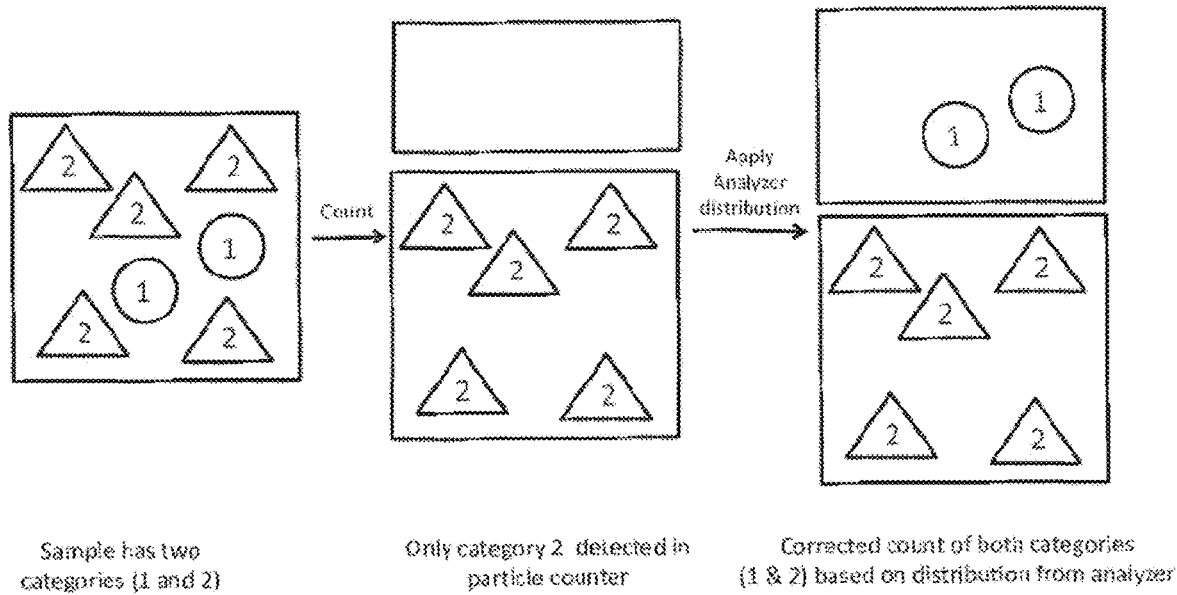
FIGS. 10A, 10B, 10C, and 10D show detection of categories of particles according to embodiments of the present invention.
Figure 10B:
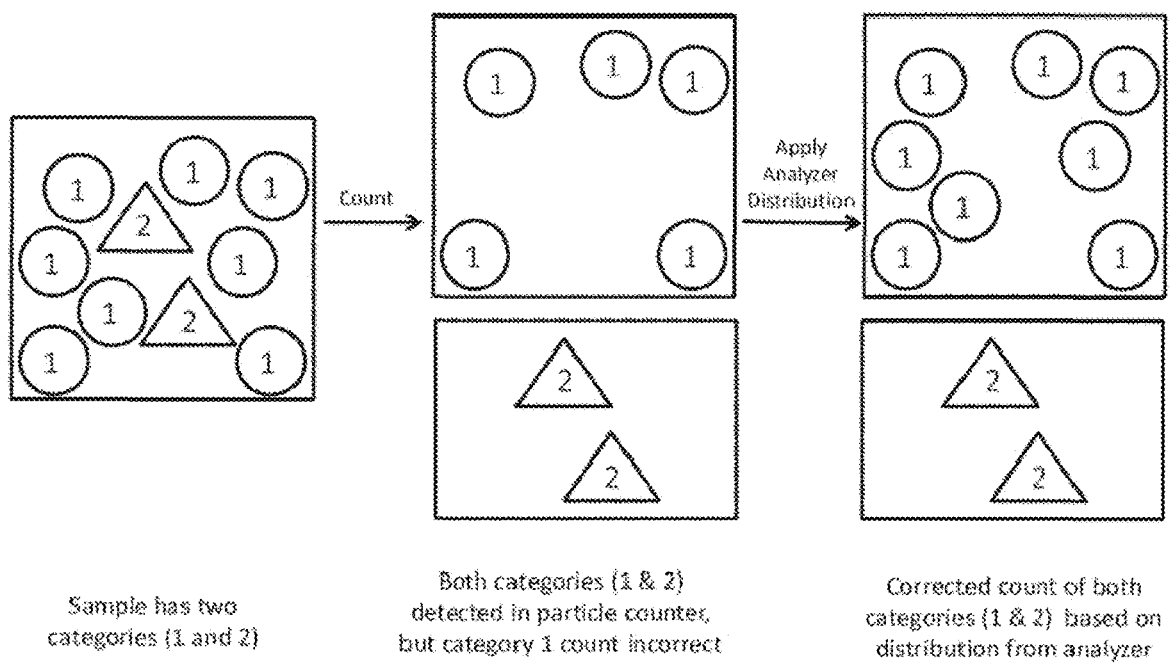

In other aspects, for example as depicted in FIG. 8 and/or FIGS. 10A and 10B, a method is provided for analyzing a sample containing particles. In such a method, a sample is provided onto a particle counter having detection limits, as indicated at step 72 in the method 70 of FIG. 8. At least a first category and/or subcategory of particles can be present in the sample at a concentration outside a detection range applicable to the first category and/or subcategory of particles, and at least a second category and/or subcategory of particles is present in the sample within a detection range applicable to the second category and/or subcategory of particles. The concentration of the second category and/or subcategory of particles in the sample is determined on the particle counter, as indicated at step 74. The sample is also provided onto an analyzer to determine a proportionate ratio of the first category and/or subcategory of particles to the second category and/or subcategory of particles, as indicated at step 76. The concentration of particles in the first category and/or subcategory can be then calculated at least in part by applying the proportionate ratio to the concentration of the second category and/or subcategory of particles, as indicated step 78. FIG. 10A shows detection of particles in a sample below the detection range, and FIG. 10B shows detection of particles present in a sample above the detection range.

FIG. 8 therefore illustrates an exemplary method 70 of determining the concentration of the first category of particles, which is present in a sample at a concentration outside a detection range on a particle counter, in accordance with some embodiments. In step 72, referring also to FIGS. 6 and 8, a sample 12 is provided onto a particle counter 15, which has at least one detection range. Sample 12 includes particles, which may be dispersed in a fluid. In some embodiments, the first category of particles is present in the sample at a concentration above an upper limit of a detection range applicable to the first category of particles. The second category of particles is present in the sample within a detection range applicable to the second category of particles. For example, the first category and/or subcategory of particles can include WBCs. The second category of particles can include platelets.

In some embodiments, the first category of particles is present in the sample at a concentration below a lower limit of a detectable range applicable to the first category of particles. The second category of particles is present in the sample within a detection range applicable to the second category of particles. For example, the first category of particles comprises platelets. The second category of particles comprises white blood cells.

In step 74 of FIG. 8, the concentration of the second category of particles in sample 12 is determined on particle counter 15. The particle counter can comprise at least one channel. The second category of particles is measured in one of the channels in some embodiments. The particle counter can comprise at least two channels in some embodiments. The first category of particles, if the concentration is within a detection range applicable to the first category of particles, can be counted in another channel.

In step 76 of FIG. 8, sample 12 is provided onto an analyzer, such as a visual analyzer 17 (e.g. as depicted in FIG. 5 or 6), to determine a proportionate ratio of the first category of particles to the second category of particles. In some embodiments, visual analyzer 17 comprises a flowcell 22 connected to an imaging device as described above. The proportionate ratio of the first category of particles to the second category of particles can be determined according to method described herein. For example, at least one chemical including at least one of a diluent, a permeabilizing agent, and a contrast agent may be introduced to the sample. Exemplary chemicals, compositions, contrast agents, and related compositions which can be used for processing blood fluid samples are discussed in copending U.S. patent application Ser. No. 14/216,811 filed Mar. 17, 2014, the content of which is incorporated herein by reference. The contrast agent can be effective to generate visual distinctions that differentiate the first categories and/or subcategories and the second categories and/or subcategories of particles. The prepared sample 12B depicted in FIG. 5 can be applied to the at least one flowcell 22 in some embodiments. Images of particles of prepared sample 12B are captured. An image analysis is performed by the analyzer which can be a visual analyzer 17 and/or processor 18. A proportionate ratio of the first category of particles to the second category of particles is then determined by analyzing the plurality of images of the ribbon-shaped sample stream.

In step 78 of FIG. 8, the concentration of particles in the first category can be then calculated by processor 18 (e.g. as depicted in FIG. 6), at least in part by applying the proportionate ratio to the concentration of the second category of particles.

Figure 9:
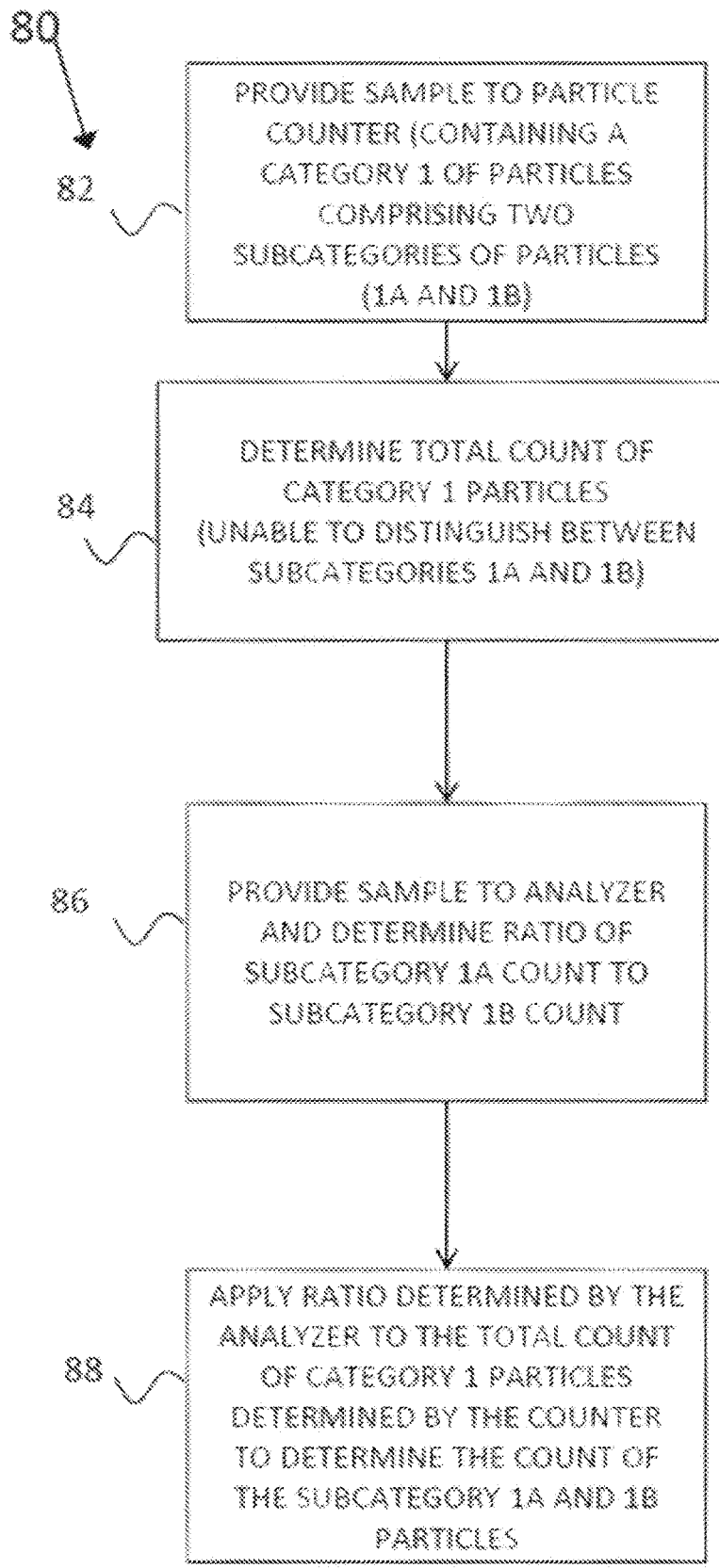
FIG. 9 illustrates an exemplary method of determining the concentration of two subcategories of particles according to embodiments of the present invention.

The present disclosure also provides methods for analyzing a sample containing particles. FIG. 9 illustrates an exemplary method 80 of determining the concentration of two subcategories of particles, which particles cannot be distinguished by the particle counter, in accordance with some embodiments. In step 82, a sample (e.g. sample 12 of FIG. 6) is provided onto a particle counter (e.g. particle counter 15 of FIG. 6), which has a detection criteria which are met by at least two categories or subcategories of particles which are desired to be distinguished. The results from the particle counter encompass these categories or subcategories within a single count in step 84 of FIG. 9.

In step 86, the sample is provided onto the analyzer (such as a visual analyzer) to determine a proportionate ratio of the first category or subcategory of particles to the second category or subcategory of particles. In some embodiments, for example as depicted in FIGS. 5 and/or 6, a visual analyzer 17 includes a flowcell 22 connected to an imaging device.

The proportionate ratio of the first category or subcategory of particles to the second category or subcategory of particles can be determined according to methods described herein. At least one chemical comprising at least one of a diluent, a permeabilizing agent, and a contrast agent is introduced to sample. The contrast agent is effective to generate visual distinctions for particle categorization and subcategorization that differentiate the first category or subcategory from the second category or subcategory of particles. As depicted in FIG. 5, the prepared sample 12B can be applied to the at least one flowcell 22 in some embodiments. Images of particles of prepared sample 12B are captured. An image analysis is performed by the visual analyzer and/or processor 18. A proportionate ratio of the at least first subcategory of particles to the second subcategory of particles is then determined by analyzing the plurality of images.

In step 88 of FIG. 9, the concentration of particles in the first category or subcategory can be then calculated by processor 18, as depicted in FIG. 5 or 6, at least in part by applying the proportionate ratio to the single count (e.g. step 84 of FIG. 9) obtained from the particle counter.

In some embodiments, the first category and/or subcategory of particles is present in the sample at a concentration above an upper limit of a detection range applicable to the first category and/or subcategory of particles. The second category and/or subcategory of particles is present in the sample within the detection range applicable to the second category and/or subcategory of particles. For example, the first category of particles comprises white blood cells. The second category of particles comprises platelets. As illustrated in FIG. 10B, the particle count from the analyzer of this disclosure can be used to correct inaccurate particle counts associated with at least one detection range used by the particle counter, such as particle concentration, volume and/or size. By operating the apparatus as described in the present disclosure, particles present in amounts above the upper limit of the detection range can be detected and measured accurately.

In some embodiments, the first category and/or subcategory of particles is present in the sample below a lower limit of a detectable range of some parameter, for example concentration, applicable to the first category and/or subcategory of particles, as illustrated in FIG. 10A. The second category and/or subcategory of particles is present in the sample within the detection range applicable to the second category and/or subcategory of particles. As illustrated in FIG. 10A, the proportionate ratio of particle counts in the two categories and/or subcategories from the analyzer of this disclosure can be used to correct inaccurate counts from the particle counter for at least one category and/or subcategory. By operating the apparatus as described in the present disclosure, particles present below the detection range limit, which are not detected by the particle counter, can be measured accurately.

As shown in FIG. 10A, the particle counter provides a particle count for category 2. The analyzer provides a proportionate ratio of particle counts for categories 1 and 2. By multiplying the proportionate ratio times the particle count for category 2, the process arrives at the particle count for category 1. The first category and/or subcategory of particles may comprise, for example, platelets. The second category and/or subcategory of particles comprise white blood cells. According to some embodiments, the dynamic or detection range extensions systems and method disclosed herein can be used to obtain accurate platelet counts when the number of platelets contained in the sample is low.

In some embodiments, the analyzer includes an imaging device and a flowcell connected to the imaging device to determine a proportionate ratio of the first category and/or subcategory of particles to the second category and/or subcategory of particles. At least one of a diluent, a permeabilizing agent, a contrast agent is introduced to the sample. The at least one chemical is effective to generate visual distinctions that differentiate the first and the second categories and/or subcategories of particles. In a step of determining such a proportionate ratio, the sample is applied to the at least one flowcell present in some embodiments. A plurality of images of particles of the sample are captured to provide a statistically significant estimation of a count or proportionate ratio. A proportionate ratio of the at least first category and/or subcategory of particles to the second category and/or subcategory of particles is then determined by counting the particles in each of the first and second categories and/or subcategories of particles.

In another aspect, as depicted in FIG. 9 and/or FIG. 10D, a method 80 for analyzing a sample containing particles is provided to correct the particle count obtained on a particle counter. For example, the results from the analyzer, for example, the relative count, of this disclosure can be used to obtain accurate particle counts of categories and/or subcategories of particles which cannot be differentiated by the detection criterion or criteria used by the particle counter alone.

Figure 10C:
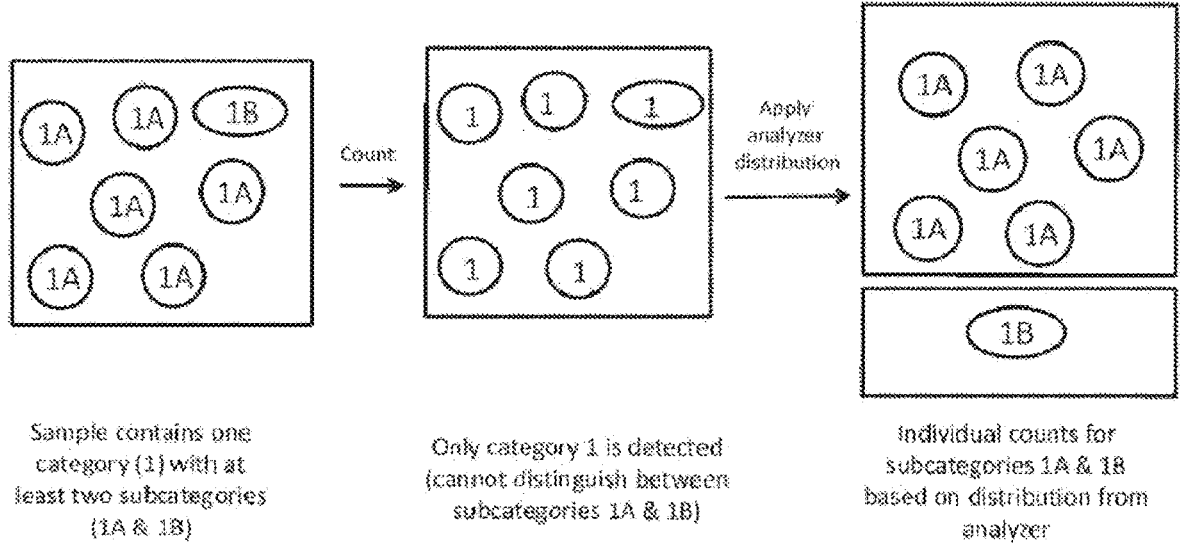
Figure 10D:
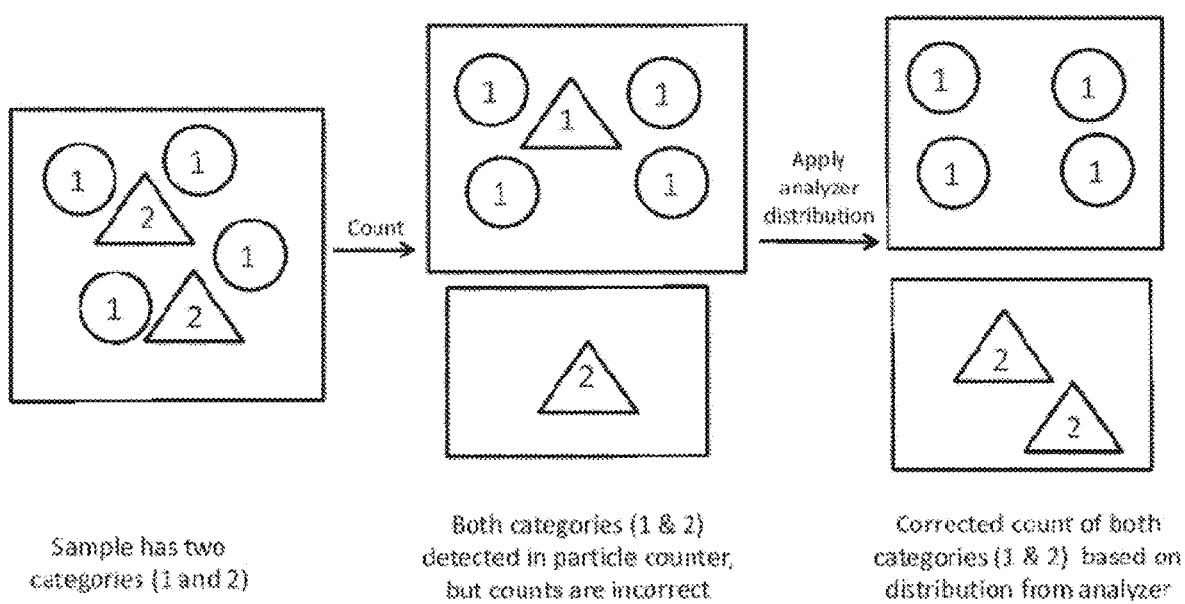

In another embodiment shown in FIG. 10C, the counter may provide a substantially accurate count for a plurality of particles. The plurality of particles encompasses members of at least two subcategories but the count does not distinguish between the subcategories. A distribution of each of the members of the at least two subcategories can be determined on an analyzer. The distribution of the subcategories is the proportionate ratio of the counts of the respective subcategories to the total. A processor is programmed to distinguish the members of the at least two subcategories. By using the distribution from the analyzer and the total particle count from the particle counter, for example as depicted in FIG. 10C, the particle count for the members of at least one of the at least two subcategories can then be determined by the processor by using the distribution of each of the members.

According to some embodiments, as depicted in FIG. 10D, the sample may have two categories of particles present. In this context, categories may be construed to include the possibility of multiple categories and/or multiple subcategories. By operating the apparatus as described in this disclosure, correction can be made to the count of particles where at least some members from at least one additional category of particles are incorrectly categorized or subcategorized, by the particle counter, as members of a first category of particles. In such a method, the count for a plurality of particles can be determined using a predetermined range, for example, size and/or volume range, to provide particle counts thereof on a particle counter. The predetermined range groups together the members of a first category of particles and at least some members of at least a second category of particles in the particle count. Those particles in the one or more categories or subcategories which are incorrectly counted as another category of particle in one channel of the apparatus can be measured separately and accurately using the analyzer configured to distinguish a distribution of the particles over the first category of particles and the at least a second category of particles in the sample. The distribution of the categories and/or subcategories is the proportionate ratio of the counts of the respective categories and/or subcategories to the total. The processor then uses the distribution to calculate the particle count for the members of the first category and the at least a second category and/or subcategory of particles. In this embodiments, as illustrated in FIG. 10D, the apparatus and methods of this disclosure and the count of particles in each category and/or subcategory can be corrected.

As shown in FIG. 10D, the particle counter may provide a substantially accurate total count comprising two categories. This count may include presumed counts for categories 1 and 2. However, the presumed count is inaccurate in that the particle counter has misclassified at least one member of category 2 with category 1. The analyzer provides a distribution of particle counts based on a smaller sample than used in the particle counter, for categories 1 and 2, but the analyzer produces an accurate distribution. The processor uses this information to arrive at an accurate count for both categories. This same process can be used for samples containing more than two categories and/or subcategories of particles.

For example, members of different particle categories or subcategories with similar size or morphology may not be accurately categorized or subcategorized by the particle counter. For example, "giant" PLTs, PLT aggregates, clumps, multiple platelets and nucleated RBCS may be mistakenly counted as WBCs, resulting in a WBC count higher than that actually exists in the sample. As another example, microcytic red cells, cell fragments, artifacts, and even electronic noise may be mistakenly counted as platelets, resulting in an inaccurately high count of PLTs.

In some embodiments, the analyzer is a visual analyzer comprising an imaging device and a flowcell. As an example, at least one chemical comprising at least one of a diluent, a permeabilizing agent, a contrast agent is introduced to the sample. The at least one chemical is effective to generate visual distinctions that differentiate the first category and/or subcategory and the second category and/or subcategory of particles. In a step of determining such a distribution, the sample is applied to the at least one flowcell present in some embodiments.

In a step of determining a distribution of each of the members of at least two categories and/or subcategories of particles, at least a part of the sample is applied into the at least one flowcell. The at least one chemical is effective to generate visual distinctions that differentiate the members of the categories and/or subcategories of particles. A plurality of imaging of particles of the sample is captured. A plurality of images of particles of the sample is captured to provide a statistically significant estimation of a count or proportionate ratio. A proportionate ratio of the at least first category and/or subcategory of particles to the second category and/or subcategory of particles is then determined by counting the particles in each of the first and second categories and/or subcategories of particles.

A proportionate ratio of the members of each of two or more subcategories of particles within a category and/or subcategory of particles, and/or a proportionate ratio of the members of a first category and/or subcategory of particles to the members of at least one other category and/or subcategory of particles can be determined, based on the plurality of images of particles of the sample. A count or concentration value for each category and/or subcategory of particles can then be calculated, estimated, inferred and/or derived. As an example, the concentration of subcategories of particles can be determined based on the proportionate ratio of each subcategory of particles from the analyzer, and the count of the total number of particles in the category from the particle counter. In some embodiments, the members of the at least two subcategories comprises at least one type of particles selected from a group consisting of subcategories of white blood cells, platelets, and red blood cells.

Accordingly, in some embodiments, the method further comprises determining a proportionate ratio of the count of particles in one category and/or subcategory of particles present at a concentration outside a detection range applicable to the one category of particles of the particle counter versus the count of particles in a second category and/or subcategory of particles that is within a detection range applicable to the second category and/or subcategory of particles, based on the plurality of images of particles of the sample from the analyzer and/or processor. The concentration in the sample of the category and/or subcategory of particles outside the detection range of the particle counter can be then determined, by applying the proportionate ratio to the particle count obtained on the particle counter. For example, in some embodiments, the first category and/or subcategory of particles is present in the sample at a concentration above an upper limit of the detection range limit applicable to the first category and/or subcategory of particles. The second category and/or subcategory of particles is present in the sample within the detection range of the particle counter (below an upper limit and above the lower limit of the detection range) applicable to the second category and/or subcategory of particles. As another example, where the detection criterion or criteria used by the particle counter miscategorizes particles by grouping particles of a first category and/or subcategory with particles of at least a second category and/or subcategory, the particle count for the first and second categories and/or subcategories can be corrected from proportionate ratios of the particles determined from the plurality of images of the particles of the sample from the visual analyzer and/or processor.

The detection range of measurement may be limited on a particle counter 15 alone in FIG. 6. For example, the upper detection limit for WBCs might be less than 100,000 to 200,000 per μL on a particle counter 15. The lower detection limit for PLTs might be higher than 10,000 per μL. By using the apparatus described herein, the effective detection range of measurement can be extended, for example, the upper detection limit for WBCs can be extended up to about 300,000, 350,000, 400,000, 410,000, 420,000, 430,000, 440,000, 450,000, 460,000, 470,000, 480,000, 490,000, 500,000, 510,000, 520,000, 530,000, 540,000, 550,000, 560,000, 570,000, 580,000, 590,000, 600,000, 610,000, 620,000, 630,000, 640,000, 650,000, 660,000, 670,000, 680,000, 690,000, 700,000, 710,000, 720,000, 730,000, 740,000, 750,000, 760,000, 770,000, 780,000, 790,000, 800,000, 810,000, 820,000, 830,000, 840,000, 850,000, 860,000, 870,000, 880,000, 890,000, 900,000, 910,000, 920,000, 930,000, 940,000, 950,000, 960,000, 970,000, 980,000, 990,000, or 1,000,000, 1,000,000, 1,010,000, 1,020,000, 1,030,000, 1,040,000, 1,050,000, 1,060,000, 1,070,000, 1,080,000, 1,090,000, 1,100,000, 1,110,000, 1,120,000, 1,130,000, 1,140,000, 1,150,000, 1,160,000, 1,170,000, 1,180,000, or about 1,190,000, cells per μL, or any range between any two of those values, in some embodiments. The lower detection limit for PLTs can be extended down to 10,000, 9,500, 9,000, 8,500, 8,000, 7,500, 7,000, 6,500, 6,000, 5,500, 5,000, 4,500, 4,000, 3,500, 3,000, 2,500, 2,000, 1,500 or 1,000, or 500, 400, 300, 200, or 100 cells per μL in some embodiments.

The analyzer preferably comprises a visual analyzer 17 operable to determine a proportionate ratio of the first category and/or subcategory of particles to the second category and/or subcategory of particles. In this embodiment, the proportionate ratio as described above can be determined by analyzing the plurality of images of particles in the sample taken on visual analyzer 17.

Visual analyzer 17 can be configured to introduce to the sample at least one chemical comprising at least one of a diluent, a permeabilizing agent, and/or a contrast agent to generate visual distinctions for particle categorization and subcategorization. Such visual distinctions differentiate the members of the at least two categories. Images of particles of the sample are captured. Visual analyzer 17 and the processor 18 are configured to determine a proportionate ratio of each category or subcategory of particles, by discriminating among the images of particles of the sample. The concentration of each category or sub-category of particles is then calculated. For example, accurate results of WBCs, giant PLTs and NRBCs can be determined. On a particle counter, due to similar size or morphology, giant PLTs and NRBc are counted as WBCs. By operating the apparatus as described, particle count or concentration of giant PLTs and nRBCs can be reported accurately.

In some embodiments, the sample can comprise particles whose size is outside a detection size range of particle counter 15. Visual analyzer 17 and processor 18 are configured to detect the particles and determine a proportionate ratio of the particles outside a detection size range to particles within the detection size range of the particle counter 15, based on the images of particles of the sample. The concentration of the category and sub-category of particles outside the detection size range of the particle counter 15 can be then calculated.

Generally, methods for analyzing a sample containing particles are provided to correct the particle count obtained on a particle counter. An exemplary method can be used for differentiating different categories of particles, including the corresponding subcategories, falling into the same category and/or subcategory of particles on the particle counter 15, for example as depicted in FIGS. 5 and 6. The method can be used to correct particle counts obtained in particle counter 15. In some embodiments, for example, the first category and/or subcategory of particles comprises one or more types of abnormal blood cells, immature blood cells, clumped blood cells, or abnormally sized blood cells. The second category and/or subcategory of particles comprise white blood cells. By operating the apparatus as described herein, the particles in subcategories can be distinguished by the analyzer, and counts of categories and/or subcategories of particles obtained from the particle counter can be corrected.

A sample or portion thereof is provided onto particle counter 15 to detect particles and provide particle counts based on one or more selection criteria that may encompass sub-categories of at least two categories of particles. For example, the purported WBC category from the particle counter may also contain a small amount of giant PLTs and NRBCs. That category from the particle counter can further comprise subcategories of white blood cells that cannot be distinguished by the particle counter. Another portion of the sample may also be analyzed on the visual analyzer, as described below, to resolve these miscategorizations and/or subcategorize the undistinguished WBC subcategories.

A distribution of each of the at leak two subcategories or categories can be determined on analyzer 17 as depicted in FIG. 5. Such a distribution can be presented in a numerical ratio, proportionate ratio and/or other function of the relative counts. In some embodiments, such a distribution can be determined according to methods disclosed herein on a visual analyzer 17 comprising a flowcell 22 and an imaging device 24. As described, sample 12A, which may be a portion of a sample, is applied to the at least one flowcell 22. At least one chemical comprising at least one of a diluent, a permeabilizing agent, a contrast agent is introduced to sample 12A. The at least one chemical comprising at least one of a diluent, a permeabilizing agent, and/or a contrast agent is effective to generate visual distinctions that differentiate the at least two categories of particles, and differentiate the at least two subcategories of the at least one category of particles. A plurality of images of particles of sample 12B is captured. An image analysis is performed on visual analyzer 17 and/or processor 18.

In some embodiments, processor 18 is programmed to distinguish the members of the at least two categories and/or subcategories. A proportionate ratio of the count of particles in each of the at least two subcategories or categories of particles can be determined, based on the plurality of images of particles of the sample. The particle count for the subcategories of at least one of the at least two categories obtained from the particle counter 15 can then be corrected on processor 18 by using the distribution of each of the sub-categories. The concentration of each subcategory of particles can be calculated on processor 18, based on the proportionate ratio of each subcategory of particles and the particle count of the category of particles obtained from the particle counter.

Methods disclosed herein also can be used for differentiating one or more types of particles outside a detection range on particle counter 15, in accordance with some embodiments. For example, these particles can be blood cells or other fragments, which are too large or too small to be detected on particle counter 15. On visual analyzer 17 a proportionate ratio of the counts of one type of particle outside a detection range on the particle counter to another type of particle within the detection range of the particle counter can be determined based on the plurality of images of particles of the sample. The concentration of the type of particles outside the detection range in the sample then can be determined, by applying at least in part the proportionate ratio to the particle count obtained on the particle counter 15.

Hence, embodiments of the present invention encompass hybrid systems and methods, for example which combine electronic cell counting and photographic cell imaging techniques, for example to analyze cells that might be difficult to distinguish electrically, or to analyze cells present in amounts that make it difficult to obtain an accurate electronic count thereof.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

All patents, patent publications, patent applications, journal articles, books, technical references, and the like discussed in the instant disclosure are incorporated herein by reference in their entirety for all purposes.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention. Accordingly, the present invention is not limited to the embodiments described above or depicted in the drawings, and various embodiments and modifications can be made without departing from the scope of the claims below.

What is claimed is:

1. A method for measuring a quantity of a first cell type in a blood fluid sample, the sample including a second cell type, the method comprising:
   determining a population of the second cell type in a first volume of the sample comprising flowing the first volume through a hematology cell counter;
   acquiring images of a first number of the first cell type and a second number of the second cell type by injecting a second volume of the sample into a sheath fluid flowing within a flowcell so as to provide a sample stream having a thickness and a width greater than the thickness, the acquired images being acquired along an image path traversing the thickness of the sample stream;
   determining a ratio of the first number of the first cell type to the second number of the second cell type using the acquired images; and
   calculating a cell quantity measure of the first cell type in the sample using the ratio and the population of the second cell type;
   wherein the first cell type is different than the second cell type.

2. The method of claim 1, wherein the cell quantity measure comprises a cell concentration for the first cell type in the blood fluid sample.

3. The method of claim 1, wherein the cell quantity measure comprises a cell count for the first cell type in the blood fluid sample.

4. The method of claim 1, wherein the calculating of the cell quantity measure of the first cell type in the sample comprises calculating the cell quantity measure of the first cell type in the sample such that the cell quantity measure of the first cell type is more accurate than a population of the first cell type in the sample determined by flowing the sample though the hematology cell counter.

5. The method of claim 1, further comprising determining a population of the first cell type in the first volume of the sample as a result of flowing the first volume through the hematology cell counter, wherein the determined population of the first cell type in the first volume is above or below a desired accuracy range for the first cell type, and is different from the calculated cell quantity measure of the first cell type.

6. The method of claim 5, wherein the determined population of the first cell type is zero.

7. The method of claim 5, wherein the determined population of the first cell type is greater than zero.

8. The method of claim 5, further comprising calculating a cell quantity measure of the second cell type in the sample using the ratio and the population of the second cell type.

9. The method of claim 1, wherein the determining of the population of the second cell type comprises detecting a change in electrical impedance in response to a second cell type flowing through the cell counter.

10. The method of claim 1, wherein the determining of the population of the second cell type comprises detecting an obstruction of a light path in response to a second cell type flowing through the cell counter.

11. The method of claim 1, wherein the determining of the population of the second cell type in the first volume comprises detecting a concentration parameter for the second cell type with the hematology cell counter, wherein the calculating of the cell quantity measure of the first cell type in the sample comprises calculating the cell quantity measure of the first cell type in the sample such that the cell quantity measure of the first cell type is more accurate than a population of the first cell type in the sample determined by flowing the sample through the hematology cell counter.

12. The method of claim 1, wherein the determining of the population of the second cell type in the first volume comprises detecting a volume parameter for the second cell type with the hematology cell counter, wherein the calculated cell quantity measure of the first cell type in the sample is more accurate than a population of the first cell type in the sample determined by flowing the sample through the hematology cell counter.

13. The method of claim 1, wherein the determining of the population of the second cell type in the first volume comprises detecting a size parameter for the second cell type with the hematology cell counter, wherein the calculated cell quantity measure of the first cell type in the sample is more accurate than a population of the first cell type in the sample determined by flowing the sample through the hematology cell counter.

14. The method of claim 1, wherein the determination of the population of the second cell type in the first volume of the sample comprises grouping together cells of the first cell type and cells of the second cell type.

15. The method of claim 1, wherein the determination of the population of the second cell type in the first volume of the sample comprises grouping together cells of the first cell type and cells of the second cell type, wherein the method further comprises determining a population of the first cell type in the first volume of the sample as a result of flowing the first volume through the hematology cell counter, and wherein the calculation of the cell quantity measure of the first cell type in the sample uses the ratio, the population of the second cell type, and the population of the first cell type.

* * * * *